(12) United States Patent
Janik et al.

(10) Patent No.: US 8,560,083 B2
(45) Date of Patent: Oct. 15, 2013

(54) FOLDABLE, IMPLANTABLE ELECTRODE ASSEMBLY

(75) Inventors: John J. Janik, Hudsonville, MI (US); Douglas Staunton, Kalamazoo, MI (US); Robert A. Brindley, Delton, MI (US); Timothy J. Bozung, Scotts, MI (US)

(73) Assignee: Stryker Corporation, Kalamazoo, MI (US)

( * ) Notice: Subject to any disclaimer, the term of this patent is extended or adjusted under 35 U.S.C. 154(b) by 202 days.

(21) Appl. No.: 12/873,397

(22) Filed: Sep. 1, 2010

(65) Prior Publication Data
US 2011/0077660 A1 Mar. 31, 2011

Related U.S. Application Data

(63) Continuation of application No. PCT/US2009/033769, filed on Feb. 11, 2009.

(60) Provisional application No. 61/034,367, filed on Mar. 6, 2008, provisional application No. 61/139,395, filed on Dec. 19, 2008.

(51) Int. Cl.
*A61N 1/05* (2006.01)

(52) U.S. Cl.
USPC .................................................. 607/116

(58) Field of Classification Search
USPC ................................................. 607/116–118
See application file for complete search history.

(56) References Cited

U.S. PATENT DOCUMENTS

| | | | |
|---|---|---|---|
| 6,415,187 | B1 | 7/2002 | Kuzma et al. |
| 2004/0186543 | A1 | 9/2004 | King et al. |

FOREIGN PATENT DOCUMENTS

| | | |
|---|---|---|
| WO | 2008/080073 | 7/2008 |
| WO | 2009/155084 | 12/2009 |

OTHER PUBLICATIONS

European Patent Office, "ISA Search Report and Written Opinion" for PCT App. No. PCT/US2009/033769.

*Primary Examiner* — Carl H Layno
*Assistant Examiner* — Paula J Stice

(57) ABSTRACT

An electrode array assembly with a frame that is foldable or bendable on which electrodes are disposed. The frame includes laterally spaced apart bridges. Tabs extend laterally outwardly from the bridges Electrodes are disposed on the tabs. Beams, also part of the frame, extend between the laterally adjacent bridges. The frame can be folded around the beams so as to cause the laterally spaced bridges to at least partially overlap. When the beams are so bent, the electrode carrying tabs extend beyond the bent beams.

23 Claims, 45 Drawing Sheets

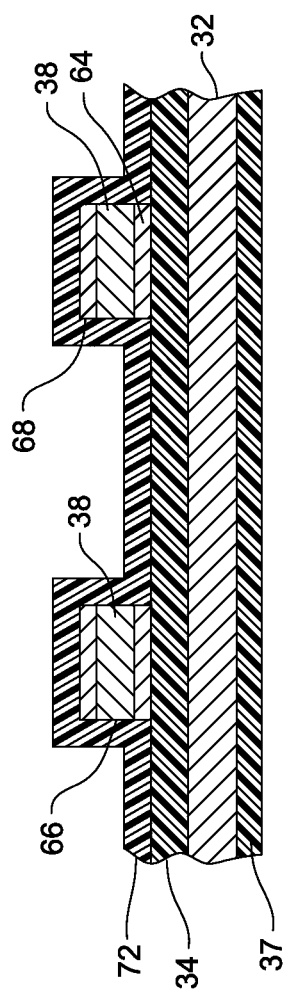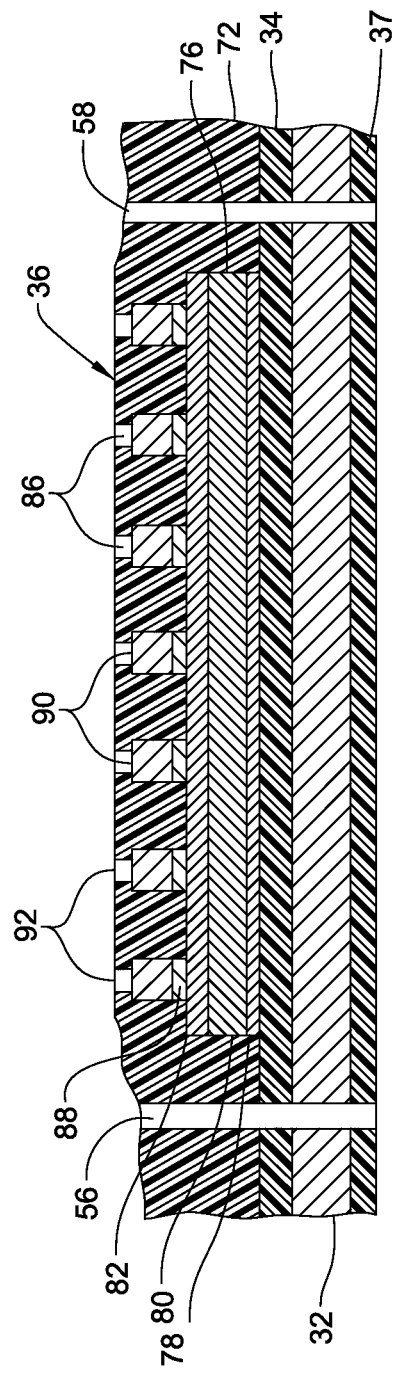

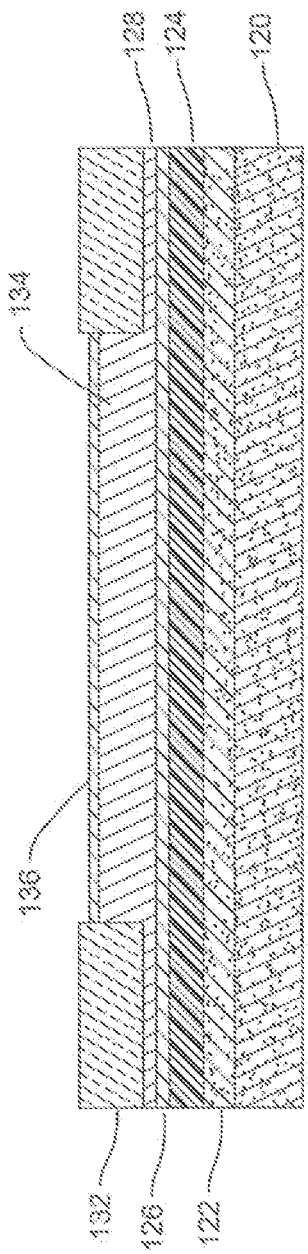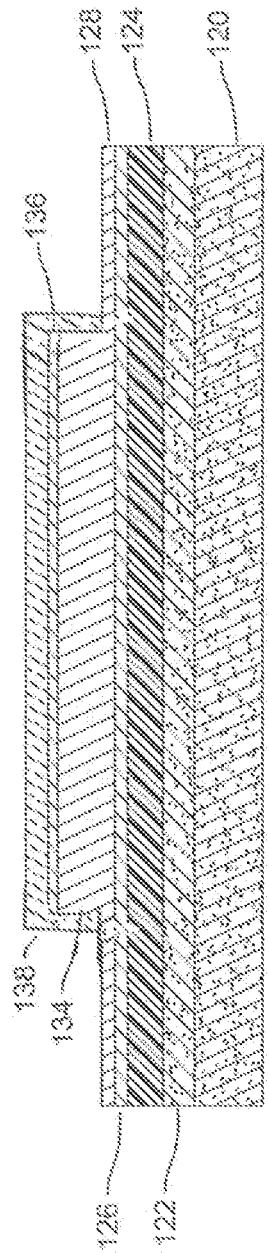

| | 292a | 292b | 292c | 292d | 292e | 292f | 292g | 292h |
|---|---|---|---|---|---|---|---|---|
| FIG. 47A | | | | | | | | |
| FIG. 47B | | +10 | | | | | -10 | |
| FIG. 47C | -5 | +10 | -5 | | | +5 | -10 | +5 |
| FIG. 47D | +5 | +5 | +10 | | | -10 | +5 | +5 |
| FIG. 47E | +4 | +4 | | | | +2 | -12 | +2 |

FOLDABLE, IMPLANTABLE ELECTRODE ASSEMBLY

RELATIONSHIPS TO EARLIER FIELD APPLICATIONS

This application is a continuation of PCT Pat. App. No. PCT/US2009/033769 filed 11 Feb. 2009. PCT Pat. App. No. PCT/US2009/0033769 is a nonprovisional application that claims priority from U.S. Pat. Apps. No. 61/034,367 filed 6 Mar. 2008 and No. 61/139,395 filed 19 Dec. 2008. The contents of the application from which this application claims priority are now explicitly incorporated herein by reference.

FIELD OF THE INVENTION

This invention relates generally to an electrode array, with multiple electrodes, that can be minimally invasively implanted adjacent target tissue within a patient and a tool for implanting the electrode array.

BACKGROUND OF THE INVENTION

There are a number of medical conditions for which it has been found that an effective therapy involves driving current through a section of the tissue of a patient. Often, the current is driven between the electrodes of an electrode array implanted in the patient. Generally, the electrode array includes a non-conductive frame on which typically two or more electrodes are disposed. Once the electrode array is implanted, current is driven from at least one of the electrodes, through the adjacent tissue, to at least one of the other electrodes. The current flow through the tissue influences the tissue to accomplish a desired therapeutic result. For example, an electrode array positioned adjacent the heart may flow currents to stimulate the appropriate contraction and expansion of the heart muscles. There is an increasing interest in implanting electrode arrays adjacent neurological tissue so that the resultant current flow induces a desired neurological or physical effect. In one known application, the current driven between the electrodes of such an array reduces the extent to which chronic pain signals are sent to the brain. This type of therapy is sometimes referred to as neuromodulation for pain management. Alternatively, the current flow stimulates a feeling of stomach fullness as part of an appetite suppression/weight management therapy. In another application, the current is flowed to tissue or nerves associated with the bladder or the anal sphincter to assist in control of incontinence. Electrodes may be implanted in a paralysis victim to provide muscle control and/or a sense of feeling.

Often, the current driven between the electrodes is sourced from a pulse generator also implanted in the patient, known as an implantable pulse generator (IPG).

Once the electrode array of the above assembly is implanted, current can be driven between selective sets of electrodes. By convention, one electrode is often referred to as the anode and the complementary electrode the cathode. In practice, since the current is typically a biphasic current; at one instant during the operation of the electrode array a particular electrode may function as an anode and, in the next instant a cathode.

The term "cathode" is typically associated with the electrode that, during the first phase of a biphasic pulse serves as a current source. The term "anode" is typically associated with the electrode that, during the first phase of a biphasic pulse serves as a current sink.

There are a number of different protocols for driving current between the electrodes of an array. One protocol is monopolar stimulation. During monopolar stimulation, current is driven from/to one or a plurality of electrodes on an electrode array to/from the case of the implanted pulse generator. The IPG thus functions as the complementary electrode to/from which the current is driven. Given the large surface area of the case, and it's relatively large distance away from the implanted electrode/electrodes, the current flowing through the tissue adjacent the case is very weak. Consequently, this current essentially has no effect on this tissue.

Alternatively, the array may be operated in a bipolar mode. In the bipolar mode, two of the electrodes on the array serve as the complementary electrodes between which the current is driven. When current is driven between three electrodes, the array is considered to be operating in a tripolar mode. Typically, when current is driven in the tripolar mode, there is a center electrode and two outer electrodes. At any given instant, the charge of the two outer electrodes is of a first polarity while the charge of the center electrode is of a second, opposite polarity.

When an array is operating in either the bipolar or tripolar mode, the current flow between the electrodes is, in comparison to monopolar stimulation, more focused. This allows more selective targeting of the tissue through which the current is to be flowed.

In bipolar or tripolar systems, the case of the IPG often functions as a neutral or reference electrode. Cathodal and anodal pulses are, respectively of negative and positive potential relative to the IPG case.

It is further understood that, regardless of whether the array is operated in the monopolar, bipolar or tripolar mode the array is operated so that charge balancing occurs. This means that the electrodes are operated so that, at any given instant, the current sourced by some of the electrodes is the same current that is sunk by the complementary electrodes. This charge balancing substantially eliminates the flow of leakage current through tissue away from the target tissue to the IPG case. Charge balancing therefore reduces the potentially adverse effects of such leakage current.

Further, it is known to operate the electrode array assembly so that the charge around each electrode is balanced on a pulse-by-pulse basis. This charge balancing around each electrode is performed to prevent a net direct current from being applied to the tissue adjacent the array and the electrodes themselves. This direct current has been known to damage both electrodes as well as the tissue adjacent the electrodes.

This balance can be performed either passively or actively. Passive balancing is achieved by placing a capacitor in series with the electrode to store/draw residual polarized charge local to the tissue-electrode interface away from the tissue. The capacitor effectively prevents the passage of a net direct current. However, to ensure this balancing, the capacitor must be given sufficient time to discharge. During this discharge period, there may be sufficient current flow that either the electrode or underlying tissue could be damaged.

Active charging balancing is achieved by applying biphasic stimulation pulses to an electrode. In this method, the charges sourced during the opposed phases of the pulse must be equal to each other to achieve total charge balance on the face of the electrode.

In the active charge balancing processes, the initial phase of the biphasic stimulation process is referred to as the lead phase. The second phase is referred to as the balancing phase. Often the magnitude of the current flow during the balancing phase is less than that of current flow during the lead phase.

Sometimes, the magnitude of the current flow during the balancing phase is so low, it does not trigger a response in the tissue through which the current is flowed. The current flowed during the balancing phase thus serves only to achieve the desired individual electrode charge balancing.

Many electrode arrays have more than three electrodes. Once an array is implanted, the current is initially driven between different sets of electrodes. The goal of this experimentation is to find the current path through the tissue that results in the most benefit and/or least adverse side effects to the patient. This can result in the array operating in a state in which one or more electrodes neither serve as current sources or current sinks.

Many electrode assemblies used in pain management therapy procedures and other therapies are shaped like flexible, elongated rods. This type of electrode assembly has a diameter typically no greater than 2 mm. At least for pain management applications, the electrode assembly is so sized so it can be positioned in the epidural space within a vertebral column, the space between the ligamentum flavum and the spinal cord dura. More particularly the electrode assembly is positioned in this space on or near the spinal cord dura. The electrode assembly is sufficiently miniaturized so it can be introduced through a cannula or needle-like delivery device. This eliminates the need to invasively cut through the paraspinal muscles, interspinus ligament, ligamentum flavum and expose portions of the lamina to gain access to the epidural space to position the electrode. The electrode assembly itself includes a number of longitudinally spaced apart electrodes. Once the electrode assembly is positioned adjacent the dura, current pulses are applied between selected sets of electrodes. These current pulses flow, in part, through the spinal cord. The electrode current flow patterns are experimented with until the individual reports, instead of pain, a more tolerable tingling sensation. This tingling sensation is known as paresthesia.

The above therapy offers some relief to many individuals suffering from chronic pain. One disadvantage of these assemblies is that their construction provides a relatively low spatial resolution of spinal cord stimulation. If the current pulses cannot be directed through the sections of the dorsal column that are most closely associated with the neurons through which the pain signals are being transmitted, the application of the signal may not result in appreciable masking of the pain signals. One of the few ways to compensate for this imprecise targeting is to over stimulate the dorsal column nerves. This may result in some nerves being subjected to needless stimulation. Moreover, the potential fields generated between individual electrodes tend to drive currents radially. The emission of a fraction of this current away from the spinal cord is needless expenditure of electrical energy. This can be a significant drawback in an implanted device in which the available power is limited. Also, owing to the rounded and flexible shape of this type of electrode assembly, it can shift position along the spinal cord. Should this event occur, the current pulses directed between the individual electrodes may no longer be of any use for inhibiting the transmission of pain signals.

There have been attempts to overcome some of the above limitations by providing implantable electrode systems that include electrode arrays that are paddle-shaped. The electrodes integral with a paddle shaped electrode array are typically spaced closer together than the electrodes of a rod type electrode array assembly. Further, the electrodes of a paddle-type electrode array are typically positioned towards the surface of the dura. To implant this type of assembly, it is necessary to invasively cut through the para-spinal muscles, interspinus ligament, ligamentum flavum and portions of the lamina. This implantation requires a relatively invasive surgical procedure.

SUMMARY OF THE INVENTION

This invention is directed to a new and useful electrode array assembly adapted for implantation against or within living tissue. The electrode array assembly of this invention includes a frame on which plural spaced-apart electrodes are arranged in rows and columns. The frame can be shaped to have a curved profile. The frame of the electrode array assembly of this invention is further designed to be foldable without sustaining substantial permanent deformation. Once unfolded, the frame returns to its unfolded, curved, profile.

Owing to the arrangement of the electrodes in the row by column array, the electrodes of this invention are disposed over an area that has both length and width. When the assembly is positioned over tissue, for example, the spinal cord dura, current pulses can be directed through the underlying tissue in a number of different paths. This increases the likelihood that current will flow through and therefore activate specific nerves in the dorsal column that will appreciably modulate undesired pain signals.

The curved shape of the frame means that the electrode assembly as a whole has a curved shape. The curved shaped of the electrode assembly causes the assembly to conform relatively closely to the tissue against which it is placed. This conformance minimizes the likelihood that the assembly will move from the implanted position.

The electrode array assembly of this invention, in addition to potentially being curved, can be folded. To position the electrode array assembly of this invention into the body, against tissue, the assembly can be first folded so it fits into the lumen of an introducer cannula or introducer needle. The tip of the introducer cannula/needle is positioned adjacent the location where the electrode assembly is to be located. Once the cannula/needle is so positioned, the electrode array assembly is ejected. Upon ejection from the cannula/needle, the electrode array assembly unfolds to take its defined shape against the tissue against which it is to be positioned.

It should be appreciated that the electrode array assembly of this invention has numerous electrodes that are disposed over a relatively large surface area. Once deployed, the current can be sourced from a first set of electrodes and sunk to a second set of electrodes. Switching between which electrodes the current is flowed, invariably shifts through which tissue the current is flowed. The practitioner can, by experimentation, adjust through which electrodes the current is flowed as well as the magnitude of current flow, to determine which an intra-tissue current flow results in the most desirable therapeutic benefits and/or tolerable side effects. Once this current flow path is established, the electrode array assembly of this invention can be set so the electrodes continually source and sink current that results in this optimal intra-tissue current flow.

BRIEF DESCRIPTION OF THE DRAWINGS

FIG. 3 is a cross sectional view of the electrode array taken along a portion of the substrate at which two conductive traces are present;

FIG. 4 is a cross sectional view of one of the electrodes of the electrode array assembly;

FIGS. 5-17 are a sequence of cross sectional views depicting how a substrate containing the electrodes of this assembly are fabricated on a wafer;

FIG. 47A is a key for FIGS. 47B through 47E indicating which of set of eight electrodes are, at a given instant, employed as source or sink electrodes;

FIGS. 47B through 47E are diagrammatic representations of how different sets of electrodes forming the array of this invention are simultaneously actuated to serve as source or sink electrodes;

DETAILED DESCRIPTION

I. Electrode Array Assembly

Figure 1:
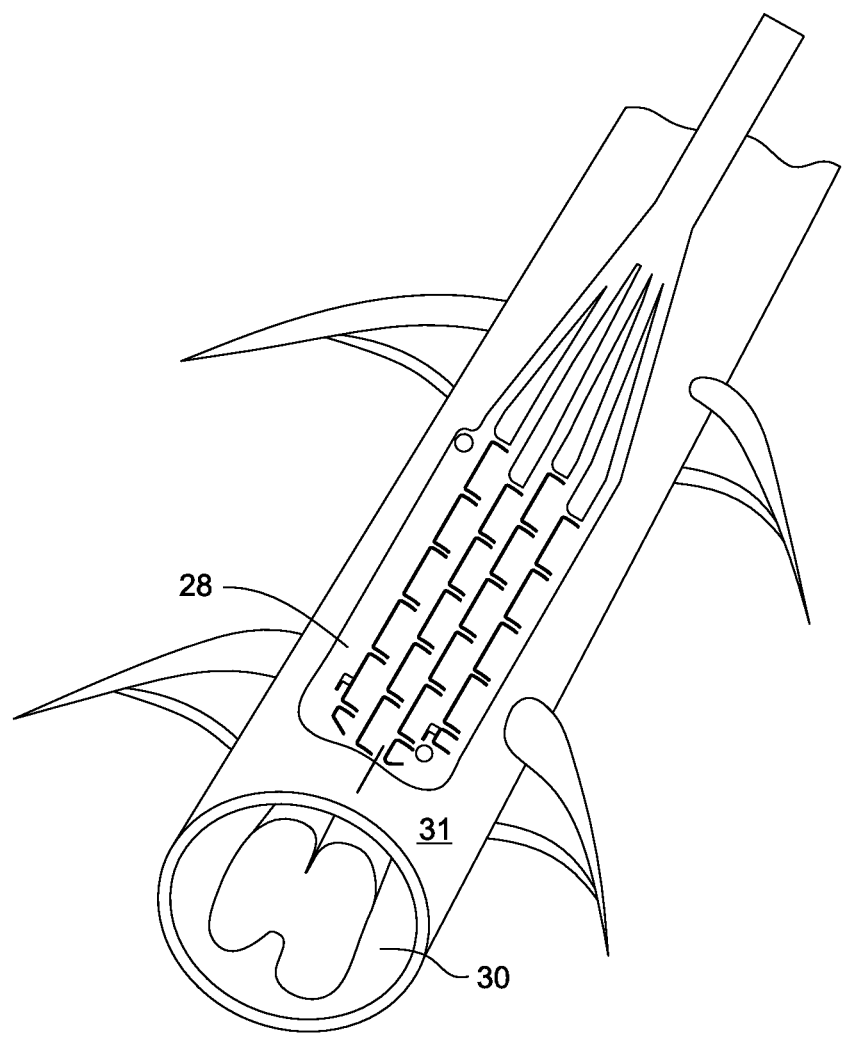
FIG. 1 is a perspective view of an electrode array assembly of this invention disposed against the dura surrounding the spinal cord.
Figure 2:
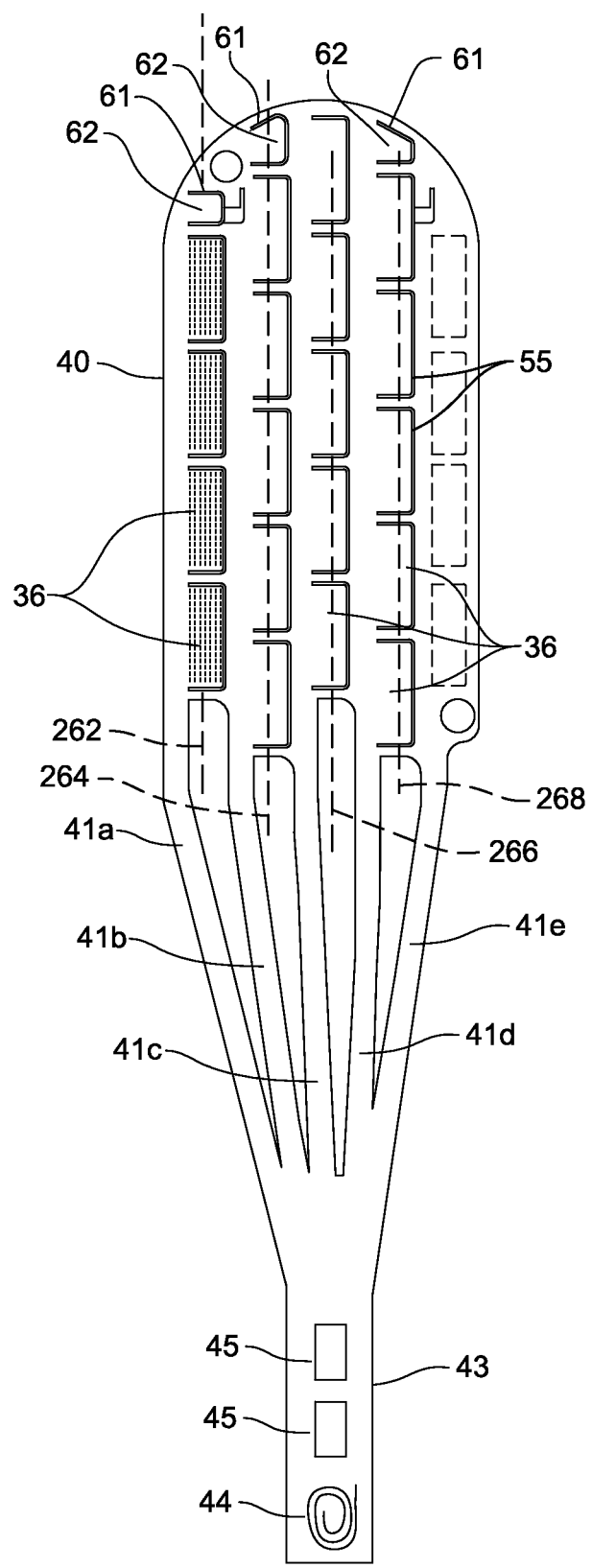
FIG. 2 is a plan view of the electrode array assembly of this invention looking at the surface of the assembly on which the electrodes are disposed.

FIG. 1 is a perspective view of an electrode array assembly 28 of this invention disposed over a dura 31 that surrounds a spinal cord 30. As best seen in FIGS. 2-4, electrode array assembly 28 includes a frame 32, seen in FIGS. 3 and 4. Frame 32 is formed from a thin section of superelastic material that can be both formed and folded into non-linear shapes. Frame 32 supports a non-conductive substrate 34. Substrate 34 generally covers the whole of the surface of the frame 32. A number of spaced apart electrodes 36 are disposed on the substrate 34.

Figure 2A:
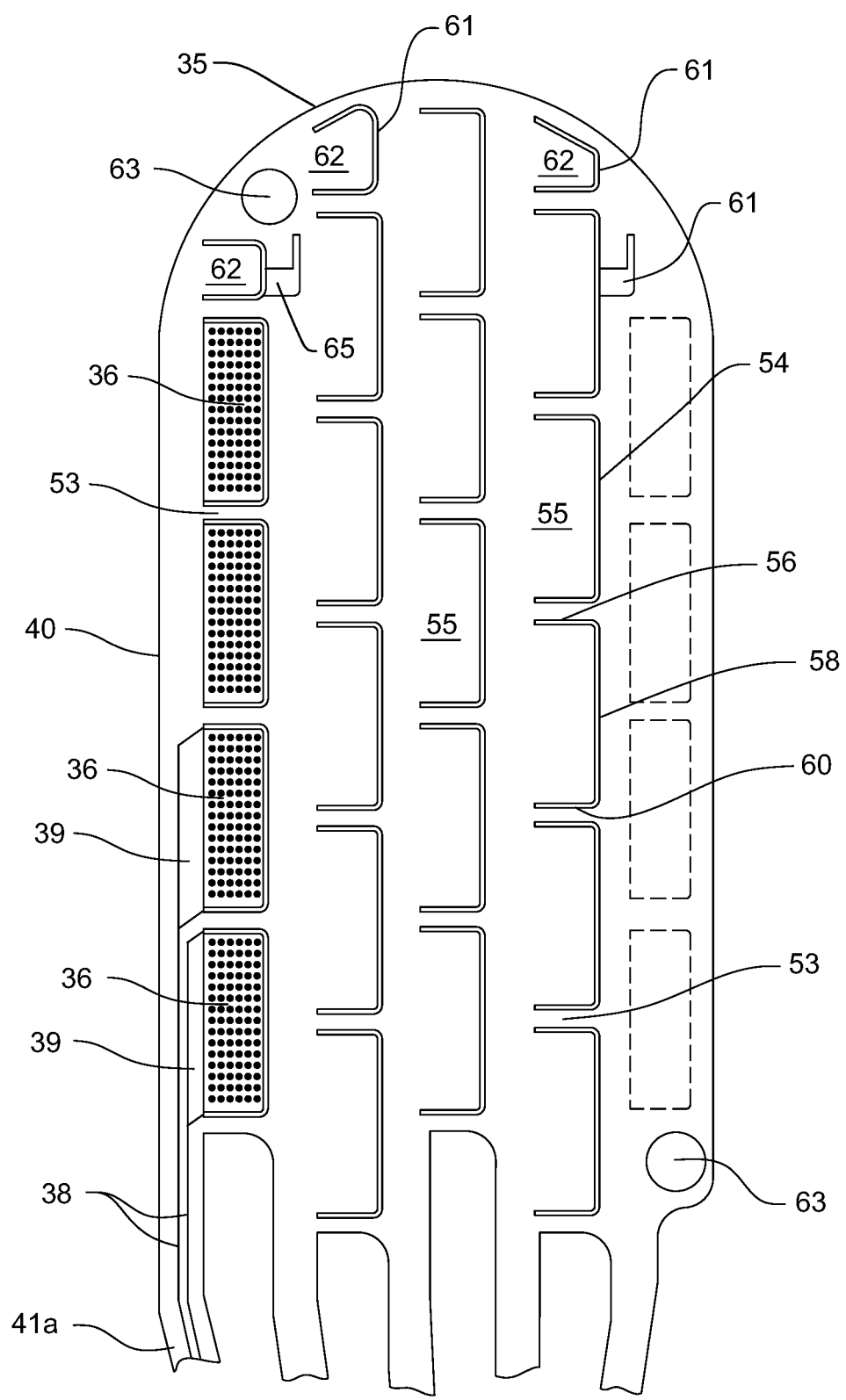
FIG. 2A is an enlarged view of a section of the electrode array assembly seen in FIG. 2.

In the illustrated version of the invention, each electrode 36 is the shape of a rectangle with rounded corners. In FIG. 2A, for ease of illustration only four electrodes, the electrodes in the first column of electrodes (the column on the left side of the drawing) are illustrated. Also, the positions of the electrodes in the fifth column of electrodes (the column on the right side of the drawing), are illustrated as dashed rectangles.

In some versions of the invention, it is contemplated that each electrode 36 has a length of between 250 and 6000 microns and more typically between 1000 and 3000 microns. Each electrode 36 has a width between 100 and 2000 microns and typically between 500 to 1500 microns. In many versions of the invention, the minimal spacing between electrodes 36 should be at least 100 microns. In some versions of the invention, the separation between the electrodes is at least 300 microns. Electrodes 36 are arranged in plural spaced apart rows and spaced apart columns on the substrate 34.

In the illustrated version of the invention, the electrodes 36 in each column of electrodes are aligned along a common longitudinal axis. The electrodes 36 in each row of electrodes are not so aligned. Thus, the lateral axis of adjacent electrodes, the electrodes in adjacent columns, are offset from each other. In the version of the invention depicted in FIG. 2, the lateral axes of the electrode rows in the first, third and fifth columns are aligned. The lateral axes of the electrode rows in the second and fourth columns are also aligned with each other.

A conductive trace 38 extends to each electrode 36. In FIG. 2A, for ease of illustration, only the conductive traces 38 and complementary conductive fans 39 of two of the illustrated electrodes 36 are shown. In the illustrated version of the invention, the end of each conductive trace 38 closest to the electrode 36 with which the trace 38 is associated widens into a conductive fan 39. Each conductive fan 39 has a longitudinal edge contiguous with the electrode 36 with which the fan is associated.

In the illustrated version of the invention, the electrode array assembly 28 has a head 40 with a relatively wide width. Head 40 is formed to have an outwardly curved front end 35. Electrodes 36 are disposed on the assembly head 40. A number of spaced apart legs 41 extend rearwardly from the assembly head 40. In the illustrated version of the invention, the electrode array assembly has five (5) legs 41a-e. The center leg 41c is straight, at least parallel to if not aligned along the longitudinal axis of the assembly head 40. The outer legs 41a, 41b, 41d and 41e taper inwardly towards center leg 41c. Legs 41 terminate at a common foot 43 also part of the electrode array assembly 28. Foot 43, which may be longitudinally axially aligned with head 40, has a width less than the width of the head.

Disposed on the surface of the assembly foot 43 is an antenna 44 and a pair of circuits 45. In some versions of the invention, antenna 44 and circuits 45 are disposed on the same side of the frame on which electrodes 36 are located. This is not required in all versions of the invention. Conductive traces 38 are connected to at least one of the circuits 45, (connection not shown). While only partially illustrated in FIG. 2A, it should be understood that the conductive traces 38 associated with each column of electrodes 36 are disposed over the leg 41 that extends rearwardly from adjacent that column of electrodes.

Antenna 44 receives signals that both power the electrodes 36 and that contain instructions indicating through which electrodes 36 current is to be pulsed. Circuits 45 are configured to: harvest the power in the received signals; demodulate the signals to obtain the instructions contained in the signals; and establish the electrode to power supply connections specified by the instructions. A more detailed description of this type of assembly is disclosed in Applicants' Assignee's PCT Patent Application, Implantable Neuromodulation System Including Wirelessly Connected Pulse Generator And Electrode Array Assembly, PCT App. No. PCT/US2007/088580, filed 21 Dec. 2007, PCT Publication No. WO 2008/080073, the contents of which are incorporated herein by reference. In general though it should be understood that disposed on the assembly 28 is a circuit for storing the power of the received signals. A switch circuit selectively connects the individual electrodes to the anode and cathode sides of the power supply and storage circuit. Another circuit demodulates the received signals to extract the instructions. A controller asserts control signals to the switch circuit to cause it to, based on the received instructions, establish the appropriate power supply-to-electrode connections.

In some versions of the invention, circuits 45 are able to monitor the performance of the assembly. In these versions of the invention, antenna 44 is able to transmit signals back to the control module or programming unit.

Figure 35:
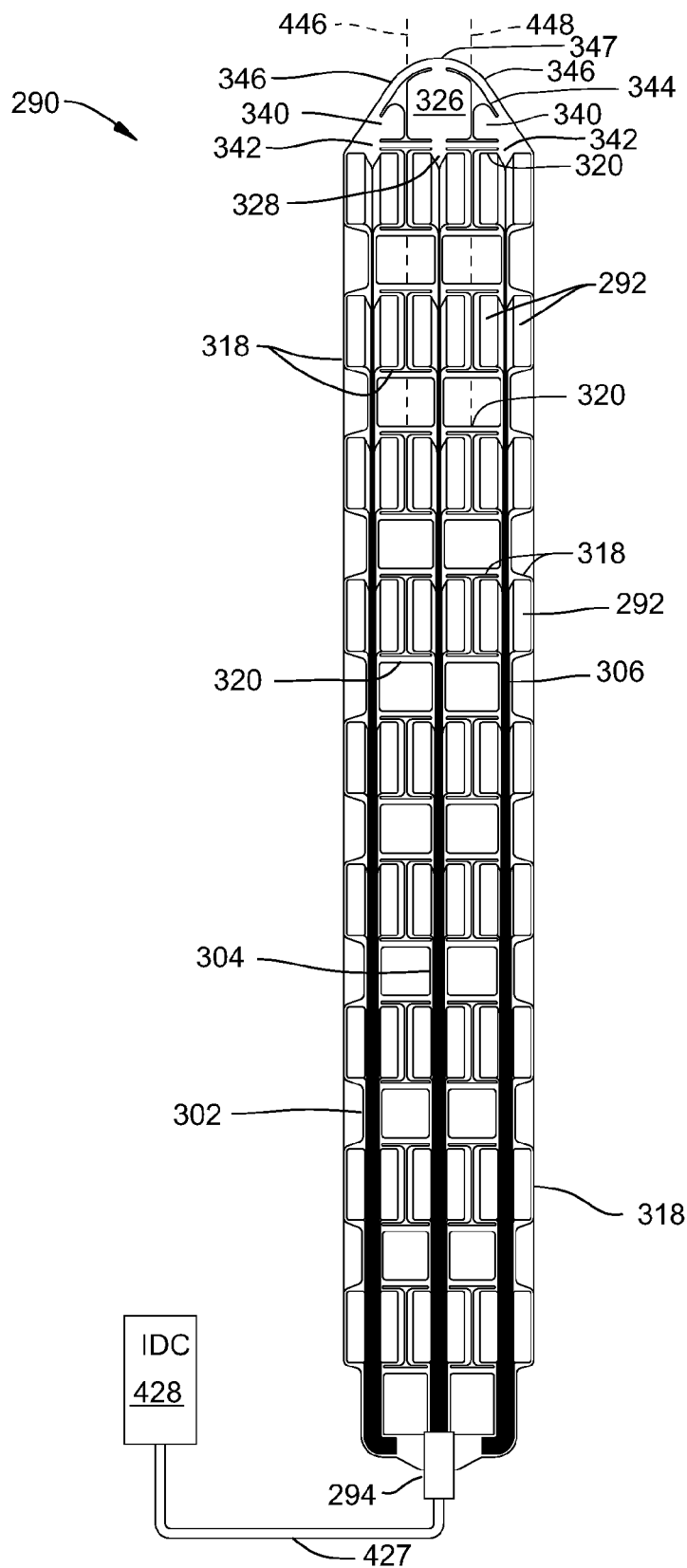
FIG. 35 is a plan view of an alternative electrode array assembly of this invention.
Figure 36:
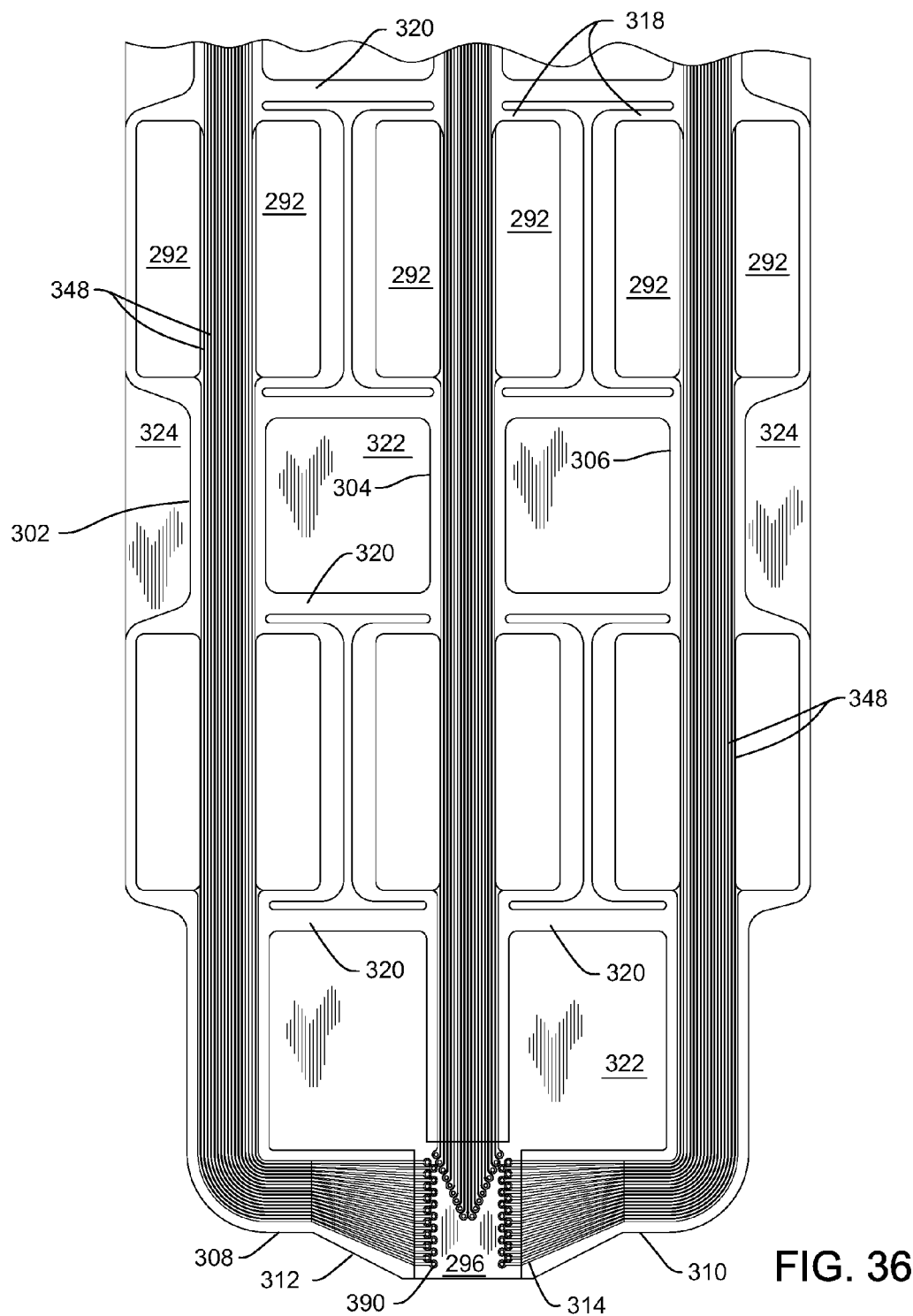
FIG. 36 is an enlarged plan view of the proximal end of the electrode array of FIG. 35 wherein the drive module is absent from the terminal pad.

Terminals 390, seen in FIG. 36 and described with respect to electrode array 290 of FIG. 35, can be used to connect conductive traces 38 to circuit components 45.

Electrode array assembly 28 is further formed to have a number of through slots 54 in the substrate 34 (one slot 54 identified in FIG. 2A). Each slot 54 is associated with and partially surrounds a separate one of the electrodes 36 in the first, second, third and fourth columns of electrodes. Slots do not surround the electrodes in the fifth column of electrodes of the assembly of FIG. 2A. Each slot 54 has three sections. There are upper and lower sections 56 and 60, respectively, located on the opposed ends of an electrode when viewed in FIG. 2A. A center section 58 connects the upper and lower sections 56 and 60 of each slot 54. Slot center sections 58 are located immediately to the side of the associate electrodes 36 opposite the sides to which conductive fans 39 extend. Each slot 54 defines a tab 55 out of a section of the electrode array assembly. In FIG. 2A the section of assembly 28 between adjacent slot upper and lower sections 56 and 60, the section of the assembly between longitudinally adjacent tabs 55, is identified as a beam 53. An electrode 36 is located on each one of the tabs 55. In the depicted version of the invention, the electrodes 36 in the fifth column of electrodes, the rightmost column in FIG. 2A, are not disposed over tabs.

Electrode array assembly 28 is further formed to have a number of supplemental slots 61. Each supplemental slot 61 generally has three sections shaped to define an auxiliary tab 62. Each auxiliary tab 62 is longitudinally aligned with the electrodes in one of the columns of slot-bordered electrodes 36. Slots 61 are located so that auxiliary tabs 62 are located immediately rearward the top curved face of the assembly head 40.

Also formed in the assembly head 40 are two circular alignment openings 63. As described below, alignment openings 63 facilitate the manufacture of the assembly 28.

Substrate 34 of the electrode array assembly 28, seen in FIGS. 3 and 4, is formed from a polyxylene polymer film, such as parylene-C which is available from Specialty Coating Systems, Inc. In some versions of the invention, substrate 34 typically has a thickness of at least 1 micron. In a number of versions of the invention, substrate 34 has a thickness between 5 and 10 microns.

Each conductive trace 38 and associated conductive fan 39 are formed from multiple layers of conductive metal. A bottom layer 64 of each conductive trace, as well the associated fan 39 is formed from chrome. Bottom layer 64 typically has a thickness of less than 280 Angstroms. Bottom trace 64 is provided because deposited chrome bonds to both polyxylene polymer and gold. Gold is the material from which the trace intermediate layer 66 is formed. Typically, intermediate layer 66 has a thickness of 5 microns or less. In more preferred versions the intermediate layer has a thickness of approximately 2 microns. The intermediate layers 66, being formed of gold, function as the low resistance conductive components of the conductive traces 38 and conductive fans 39. A top layer 68 is disposed over intermediate layer 66 and forms the topmost layer of a trace 38 and associated fan 39. Top layer 68, like bottom layer 64 is formed from chrome and has a similar thickness as the bottom layer 64. Top layer 68 is provided because the chrome of this layer, like the chrome of bottom layer 64 bonds well to the other materials from which the assembly of this invention is formed.

A non-conductive outer shell 72 is disposed over the surfaces of the substrate that support the conductive traces 38 and conductive fans 39. In one version of the invention, shell 72 consists of a second layer of polyxylene polymer parylene-C film. Shell 72 typically has a thickness of at least 1 micron. In a number of versions of the invention, shell 72 has a thickness of between 5 to 10 microns. Shell 72 insulates and protects the conductive traces 38 and conductive fans 39 and also covers the surfaces of substrate 34 that are trace, conductive fan and electrode free. As discussed below, sections of the shell 72 also cover portions of the electrodes 36.

Each electrode 36 may include a conductive base pad 76 from which a number of conductive buttons 86 project. In one version of the invention, base pad 76 includes the same three layers of material that comprise the conductive traces 38 and conductive fans 39. There is a chrome bottom layer 78; a gold intermediate layer 80 and chrome top layer 82. As discussed below, the layers forming the electrode base pad 76 are formed simultaneously with the layers forming the conductive traces 38 and conductive fans 39. Accordingly, base pad layers 78, 80 and 82 have the same thickness as trace/branch layers 64, 66 and 68, respectively.

Each conductive button 86 typically has a circular cross sectional profile when viewed from above. The diameter of the button is typically at least 10 microns. In many versions of the invention, the cross-sectional diameter of the button 86 is between and 20 and 40 microns. Conductive buttons 86 are typically not visible to the eye without magnification. For purposes of illustration only, dots represent the buttons 86 on one column of electrodes in the assemblies depicted in FIGS. 2 and 2A. This is for illustration only. Throughout the rest of the drawings, conductive buttons 86 are depicted as much larger in size than they are in actuality. This is to make the buttons 86 visible for purposes of illustration.

Each button 86 has a pedestal 88 that is disposed directly over the adjacent base pad top layer 82. Each pedestal 88 is formed from titanium and has a thickness of at least 100 Angstroms. In many versions of the invention, pedestal 88 has a thickness of around 300 Angstroms. A head 90 formed from iridium is disposed above each pedestal 88 and is the topmost component of the button 86. The head 90 has a thickness of at least 100 Angstroms and is more often at least 1000 Angstroms thick. In some versions of the invention button head 90 has a thickness of around 1500 Angstroms.

Non-conductive shell 72 is also disposed over the electrodes 36. More particularly the film forming the shell 72 is disposed over the outer surfaces of the base pad top layer 82 that are button-free. Shell 72 also extends around the outer perimeter of the exposed faces of the button heads 90. Openings 92 in the shell 72 expose the faces of the button heads 90 inward from their outer perimeters.

Frame 32 is formed from a superelastic material, that is, a material that, once formed, returns to the formed shape after being subjected to appreciable deformation. In one version of the invention frame 32 is metal, more particularly a nickel-titanium alloy. One such alloy is Nitinol. Frame 32 has a minimal thickness of 10 microns. In many versions of the invention, frame 32 has a thickness of at least 10 microns. In some versions of the invention, frame 32 has a thickness of at least 25 microns. When electrode array assembly 28 is curved, the curvature of the frame along its lateral axis, the axis that is curved, can be as little as 0.5 cm. In many constructions of the assembly 28, the frame has a curvature of between 3 to 5 cm. Larger curvatures are also possible.

II. Method of Assembly

Figure 5:
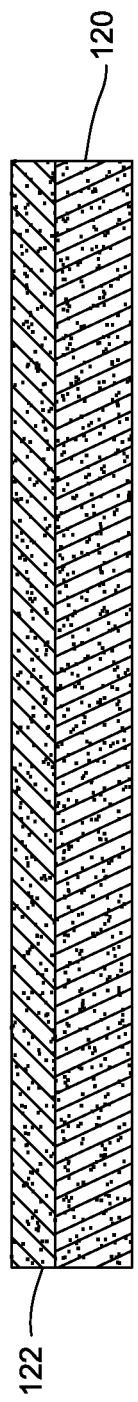

The process steps by which the electrodes 36, conductive traces 38 and conductive fans 39 of assembly 28 are formed are now discussed by initial reference to FIG. 5. Initially a silicon oxide layer 122 having thickness of approximately 2 microns is formed over the exposed surface of a silicon wafer 120. While not further described, it should be understand that after each step of depositing a layer of material that forms the electrode array assembly 28, the thickness of the layer of material is verified and the exposed surface is cleaned. As is discussed below, silicon oxide layer 122 functions as a sacrificial layer for the partially fabricated assembly 28.

Figure 6:
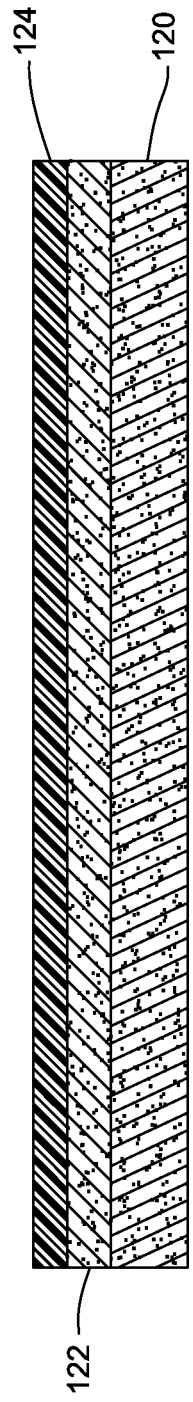

A layer 124 of parylene-C is deposited over the silicon oxide layer 122, FIG. 6. In one method of fabricating assembly 28, parylene-C layer 124 is applied by vapor deposition. Paralyne-C layer 124 as discussed below, eventually becomes part of the substrate 34 over the frame 32. During the subsequent manufacturing steps in which the electrodes 36, conductive traces 38 and conductive fans 39 are formed, parylene-C layer 124 functions as the substrate on which these components are formed.

Figure 7:
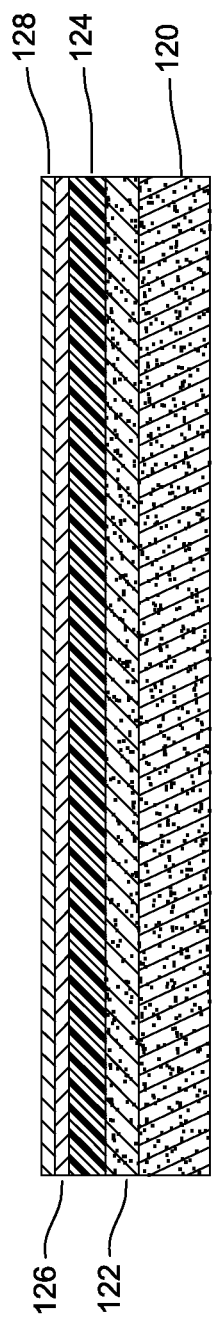

A thin layer of chrome, layer 126 in FIG. 7 is then disposed over parylene-C layer 124. Chrome layer 126 subsequently forms both the conductive trace and conductive fan bottom layers 64 and the electrode base pad bottom layers 78. Immediately after chrome layer 126 is applied to parylene-C layer 124, a small layer 128 of gold is applied over the chrome layer 126. Gold layer 128 has a thickness of approximately 500 Angstroms. Gold layer 128 functions as a seed layer of gold for the subsequent layer 134 that forms the primary conductive components of the assembly 28. Chrome layer 126 and gold layer 128 are applied via an evaporation or a sputtering process.

Figure 8:
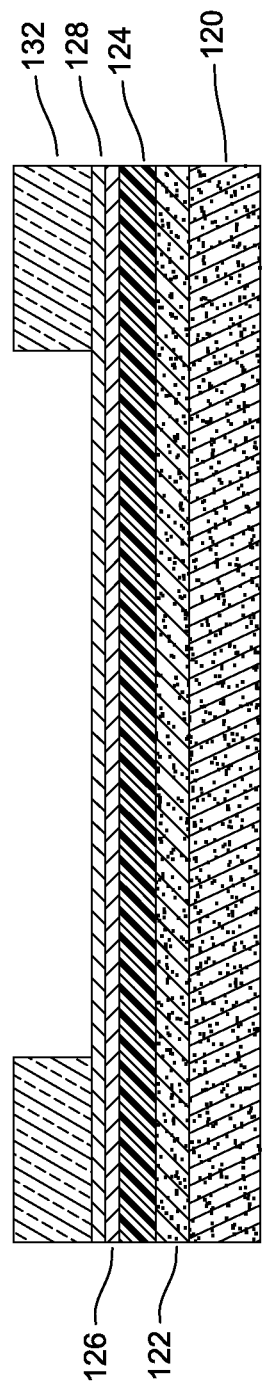

Once gold layer 128 is applied to the wafer, a photo resist mask 132 is applied to the surfaces that do not support electrodes 36, conductive traces 38 or conductive fans 39. FIG. 8 represents the application of mask 132 along a cross sectional slice of the wafer 120 at which an electrode 36 is being fabricated. Mask 132 should have a height of typically more than 3 microns and more often approximately 4 microns.

Once mask 132 is applied, gold, identified as layer 134, is applied over the exposed surfaces of gold layer 128, FIG. 9. Since the material forming layers 128 and 134 are identical in FIG. 9, and the subsequent Figures, where these layers overlap only layer 134 is called out. An electroplating process is used to apply gold layer 134 so that it has the thickness necessary to function as both the intermediate layers 66 of the conductive traces 38 and conductive fan 39 and the intermediate layers 80 of the electrode base pads 76.

In the electroplating process in which gold is applied to the wafer 120, the potential is applied to gold layer 128 that extends over the whole of the workpiece. This ensures that the gold forming layer 134 uniformly adheres to all of the exposed and spaced apart mask free surfaces of the workpiece where intermediate layers 66 and 80 are to be formed.

Once gold layer 134 is applied to the workpiece, a layer of chrome 136 is applied to the exposed surface of gold layer 134. Chrome layer 136 becomes the top layers 68 of the conductive traces 38 and conductive fans 39 and the top layers 80 of the electrode base pads 76. Chrome layer 136 is applied by evaporation or sputtering.

While not seen in the Figures, it should be understood that some of the gold and chrome released to form, respectively, layer 134 and layer 136 coats the outer surface of mask 132.

After chrome layer 136 is applied, mask 132 is removed, (post-removal view not shown.) As represented by FIG. 10, a photo resist mask 138 is then applied over chrome layer 136, as well as the underlying gold layer 134 and chrome layer 126. Mask 138 is also applied to the sides of gold layer 134 and chrome layer 136.

Figure 11:
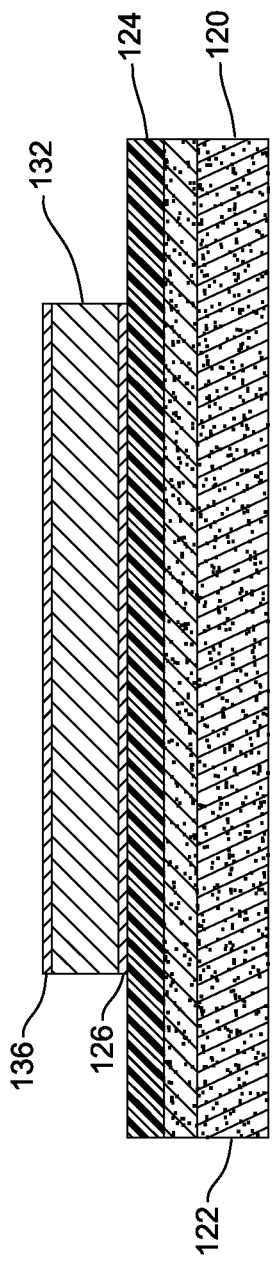

Once mask 138 is applied, the unprotected portions of gold layer 128 as well as the portions of chrome layer 126 that underlie the unprotected portions of gold layer 128 are removed. In some versions of the method of fabricating assembly 28 this is performed by a wet etch process. As a consequence of the removal of the unprotected portions of layers 126 and 128, as depicted in FIG. 11, what remains on the parylene-C layer 124 is the protected portions of chrome layer 126, the overlying gold layer 134 and the top most chrome layer 136. These chrome-gold-chrome sets of layers become the conductive traces 38, the conductive fans 39 and the electrode base pads 76. These chrome-gold-chrome sets of layers also form the below-described bond pads (not illustrated).

As mentioned above mask 138 covers the sides of gold layer 134. This is done to avoid undercutting the layered chrome/gold/chrome. Therefore, it may be necessary to apply a relatively thick layer of mask adjacent these side surfaces to minimize the likelihood of such undercuts developing. Accordingly, a very small etch protect step comprising a small tail of gold layer 128 and underlying gold layer 126 does remain after the removal of mask 138. Given the relatively small size of this step, it is not illustrated in FIG. 11 and the subsequent drawings.

Figure 12:
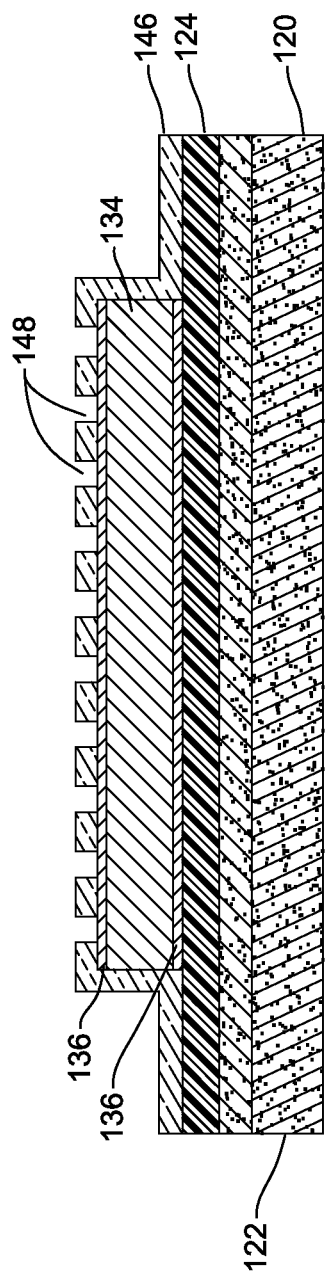

Fabrication of electrode array assembly 28 continues with the forming of the conductive buttons 86 of the electrodes 36. The fabrication of buttons 86 starts with the application of a photo resist mask 146, shown in FIG. 12, over substantially the whole of the workpiece. Mask 146 has a thickness greater than that of the conductive buttons 86 that are formed subsequent to the application of the mask 146. While mask 146 covers most of the wafer 120, there are openings 148 in the mask 146 over the exposed surfaces of the sections of chrome layer 136 that form the electrode bond pads 76.

Figure 13:
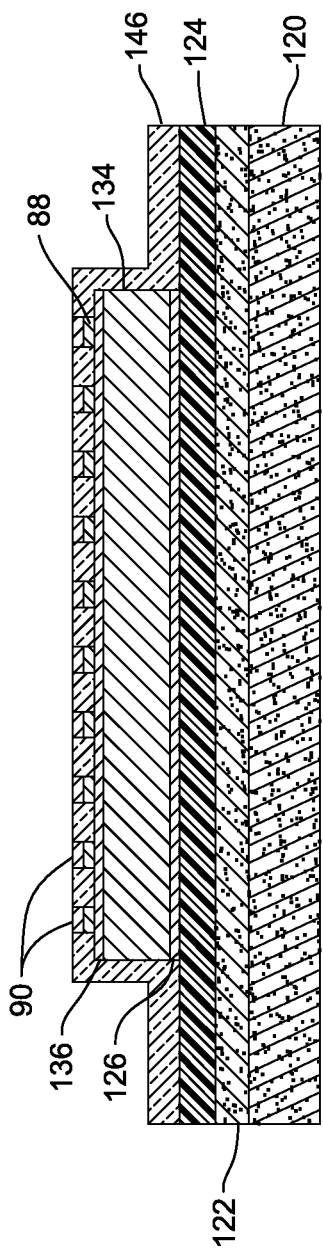

Once mask 146 is formed, first titanium and then iridium are applied to the workpiece so these metals are deposited into the mask openings 148, FIG. 13. The titanium is deposited onto the exposed sections of chrome layer 136 so as to form the button pedestals 88. Once the titanium is deposited, iridium is deposited in mask openings 148 to form button heads 90. In some methods of this invention, the titanium and iridium are deposited in separate sputtering steps. Not shown in FIG. 13 are the titanium and iridium deposited over mask 146.

Figure 14:
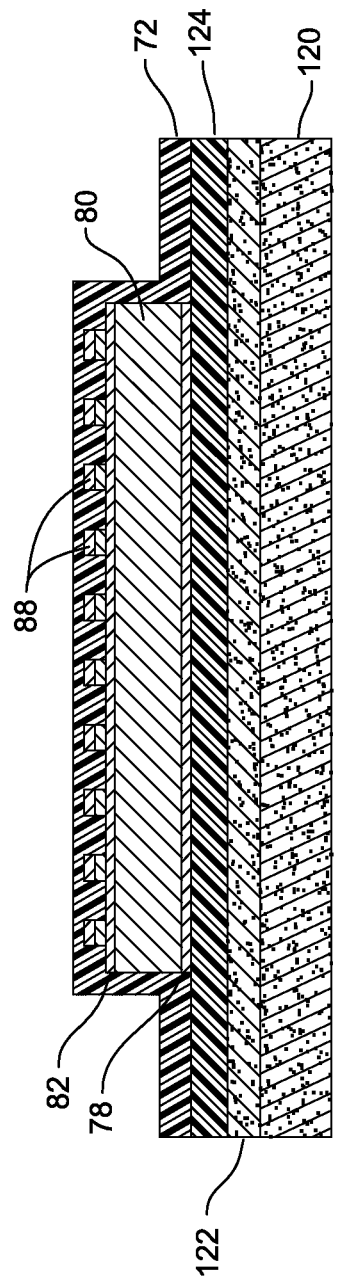

Once the electrode buttons 86 are formed, mask 146 and the metals covering the mask are removed, (post removal view not shown). Parylene-C is then deposited over the whole of the wafer, including the conductive buttons 86 as seen in FIG. 14. This layer of parylene-C forms assembly outer shell 72. The parylene-C forming outer shell 72 is also disposed over the exposed sections of the chrome that forms the electrode base pad top layer 82 over which the buttons are not present. The parylene-C also covers the exposed sections of the wafer over which the electrode array assembly or plural assemblies are not being fabricated.

Once the outer shell 72 is formed on the wafer, portions of the shell are selectively etched to define openings 92 over electrode buttons 86. In one method of assembly of this invention, this process starts with the application of a photo resist mask over the outer shell 72, (mask not illustrated). This mask is formed to define openings. Each opening is centered over a separate electrode button 86. More particularly, the openings are formed such that each opening in the mask subtends an area less than the face area of the button 86 with which the opening is associated.

Figure 15:
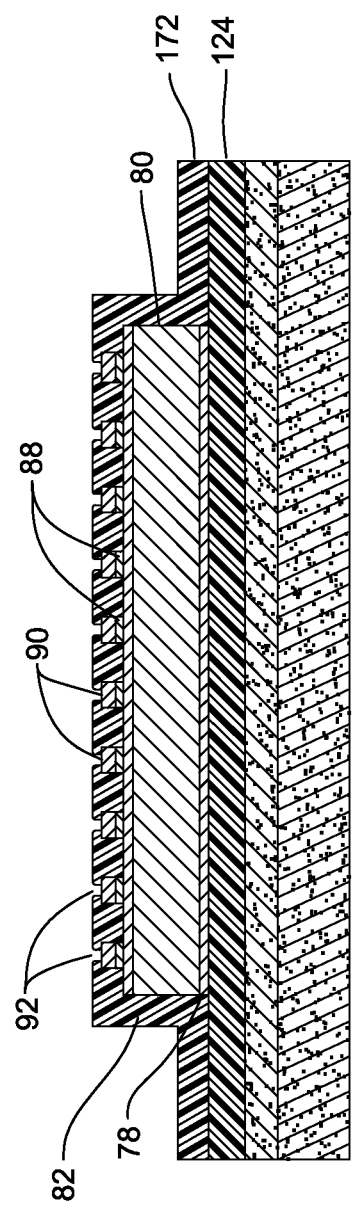

The parylene-C forming the outer shell 72 is then selectively removed. In one version of the invention, an oxygen plasma is employed to selectively remove the exposed sections of parylene. As a consequence, as seen in FIG. 15, outer shell 72 is perforated with the openings 92 through which the iridium heads 90 of the electrode buttons 86 are exposed. Often the electrode array assembly 28 is fabricated so that each opening 92 has an outer diameter that is at least 2 microns less than the diameter of the associated conductive button 86. In some preferred versions of the invention, each opening 92 has a diameter that is at least 5 microns less than the diameter of the associated conductive button 86.

Thus, at the end of this process step, the parylene-C of the outer shell 72 is present both around and over the top perimeters of the conductive buttons 86. Outer shell 72, in addition to insulating the conductive components of assembly 28, also holds the conductive buttons 86 of electrodes 36 in position.

Also, while not illustrated, the outer chrome layer of the layers forming bond pads (not illustrated) may be removed. This may be done for the ease of later bonding either wires or contact pads of components 45 to the bond pads.

Figure 16:
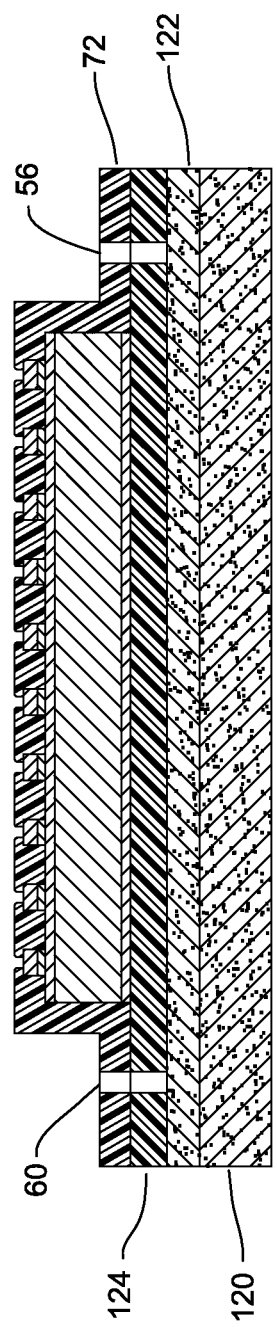

The wafer 120 on which the partially assembled electrode array assembly is formed is then processed to define slots 54 and 61 and openings 63. Also, excess parylene-C is removed from wafer 120 in this sequence of steps to define the perimeter of the assembly. While not illustrated, small dots that form perforations may also be formed in the assembly. These dots allow for the flow through of wet etchant to the sacrificial silicon oxide layer 122 in the below-discussed release process. Specifically, a photo resist is deposited over the whole of the assembly, the outer shell 72 and the exposed surfaces of the electrode buttons 86. The photo resist layer is then selectively removed in the locations where the slots 54 and other openings are formed. An oxygen plasma process is then used to remove both the exposed portions of the outer shell 74 as well as the underling layer 124 of parylene-C. This process removes material down to, but not including, the silicon oxide layer 122. As seen in FIG. 16, this process results in the removal of the parylene sufficient to form openings such as the slots, (slot sections 56 and 60 illustrated.)

While not illustrated, it should be understood that this step is used to remove the parylene surrounding the substrate sub-assembly. Presently approximately 25 substrate sub-assemblies can be formed simultaneously on a single 100 mm diameter wafer 120.

Figure 17:
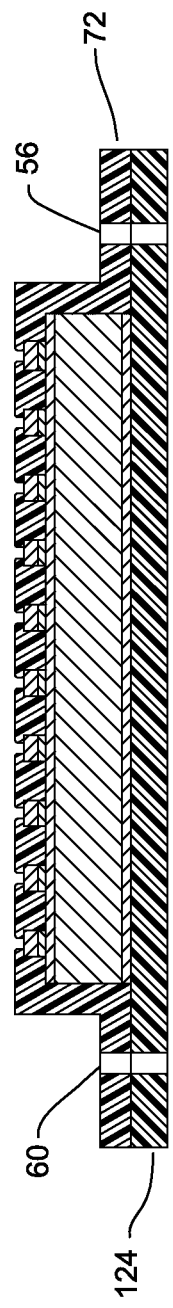

The partially assembled array, the components on the bottom layer of parylene-C, now substrate 34, is then removed from wafer 120. Specifically, a wet etch process is used to remove the sub-assembly from the silicon oxide layer 122. This leaves the electrodes 36, conductors 38 and conductive traces 39 disposed above parylene-C 124 as seen in FIG. 17. Alternative release methods could be employed. One such process is a xenon etch process.

Figure 18:
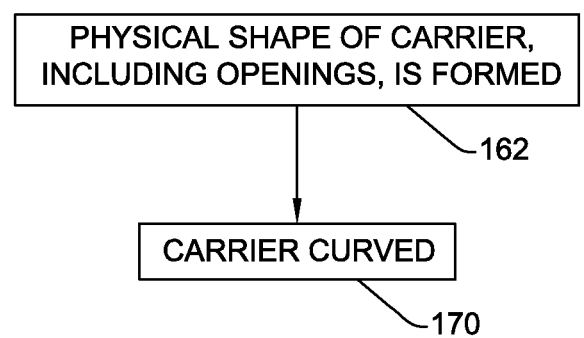
FIG. 18 is a flow chart of the initial process steps executed to form the frame.

FIG. 18 is a flow chart of the initial process steps used to form the assembly frame 32. Initially, in step 162, the physical features of the frame are formed. Thus in step 162 the frame is provided its shape, the top, bottom and side edges.

Figure 19:
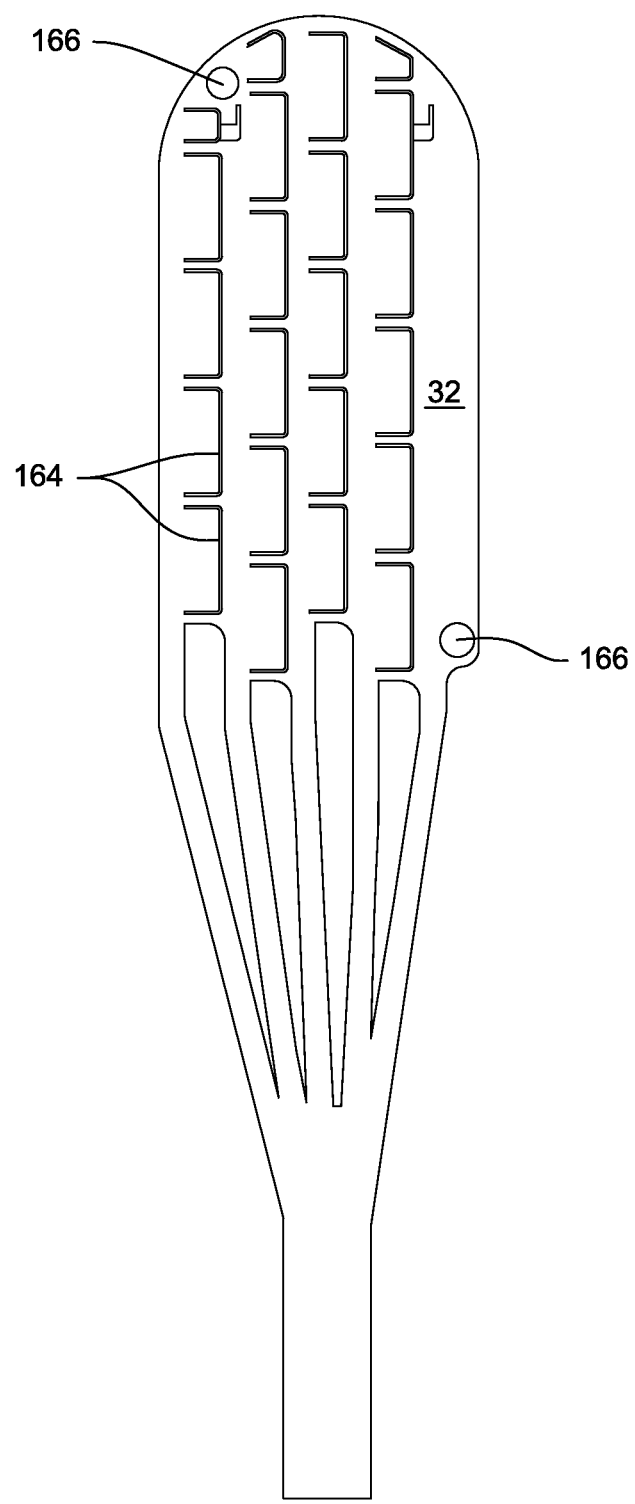
FIG. 19 is a plan view of frame

Also in step 162 openings 164, which, as seen in FIG. 19, are disposed within the outer perimeter of frame 32 are formed. As described below, openings 164 become part of the assembly slots 54. Also formed in step 162 are frame alignment openings 166. These openings 166 become sections of the assembly alignment openings 63. While not called out in FIG. 19, also formed in the frame in step 162 are the openings that form sections of slots 61 and the supplemental openings 65 (FIG. 2A) adjacent slots 61. Frame 32 may be so formed by an etching process, micromachining or a laser cutting process.

In a step 170, frame 32 is heat set to have the desired curvature.

Figure 20:
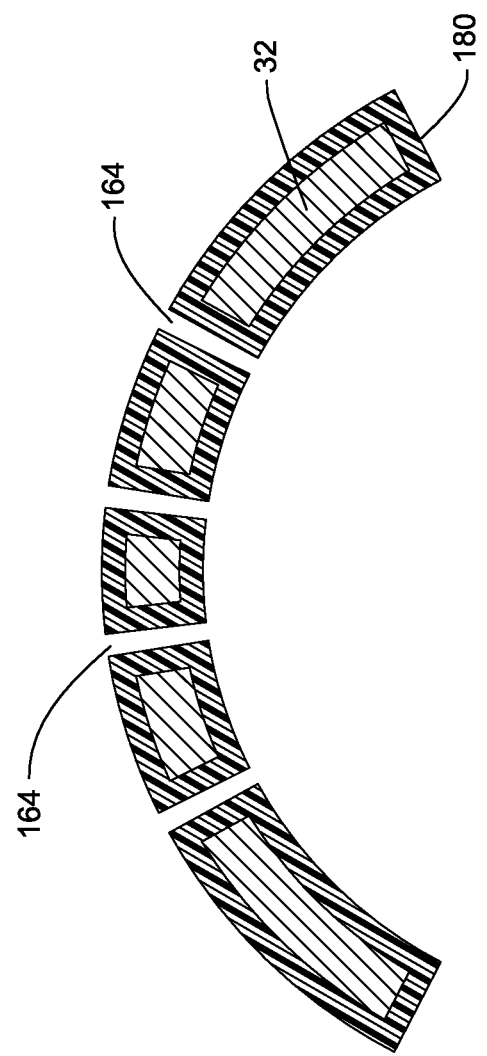
FIG. 20 is a cross sectional view of the curved and coated frame.

Once the frame is formed and curved, the substrate-electrode sub-assembly is bonded to it. This process starts with the application of a layer 180 of parylene-C to the outer surfaces of the frame. This particular layer of parylene has a thickness of approximately 5 microns. As depicted in FIG. 20, at a minimum, parylene-C layer is applied to the inner curved surface of the frame 32, the surface to which the electrodes 36 and associated components are subsequently bonded. In some versions of the invention, one or more sub-steps are used to apply parylene-C layer to the inner and outer curved surfaces and exposed edges of the frame 32.

A vapor deposition process is used to coat the parylene layer over the frame 32. In this process, vaporized parylene conforms to the surface of the frame. Accordingly, the parylene-C does not form a thin film over openings 164 and the other openings formed in the frame. (In the cross sectional view of FIG. 20, only frame openings 164 are shown.)

The substrate assembly and frame 32 are then placed in registration for the bonding process. In one method of practicing this step, the substrate-and-electrode assembly is inverted, so that the bottom parylene-C layer is the topmost layer. The subassembly is placed on an alignment jig 182 seen in FIG. 21. More specifically, the subassembly is placed on a lower frame plate 184 previously positioned over the top surface of the alignment plate 184. Lower frame plate 184 is formed from aluminum and has a thickness of approximately 12 mm.

A pair of alignment pins 186 extend upwardly from the surface of the alignment jig 182. Pins 186 are removably seated in bores 188 (one shown) in the alignment jig. The lower frame plate 184 is provided with through holes 190 (one shown) that allow the plate to be seated over pins 186. The substrate-and-electrode sub assembly is seated on the lower frame plate 184 so that pins 186 extend through the openings in the substrate that form sections of the alignment openings 63.

Frame 32 is then positioned over the substrate-and-electrode assembly so that the inner curved surface of the frame faces the exposed parylene-C layer 124. More particularly, in this step the frame is fitted to the alignment jig 182 so that the pins 186 extend through the frame alignment openings 166. Due to the positioning of the alignment openings, when the frame 32 is so positioned, the frame bends from its curved shape into a planar shape. Also, the electrodes 36 disposed over tabs 55 go into registration over the tabs with which they are associated. It should be understood that, at this time, parylene-C layer 180 integral with frame 32 abuts parylene-C layer 124 of the substrate-and-electrode assembly. Dashed line 187 represents the border between these two layers 124 and 180. Not identified is the separation between the parylene-C forming layer 124 and the parylene-C forming shell 72.

Figure 21:
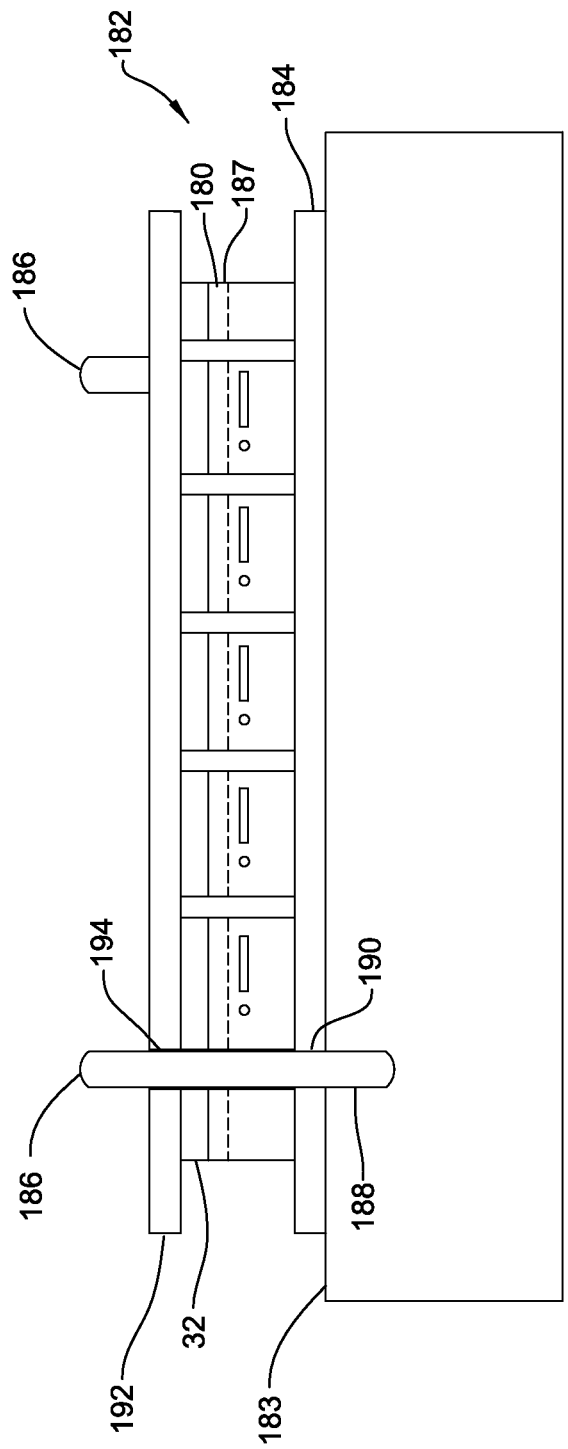
FIG. 21 depicts how the frame and substrate of this invention are positioned in an aligning jig.

Also not seen in FIG. 21 is the section of parylene-C layer 180 on the side of frame 32 opposite the side on which the electrodes 36 are formed. Post manufacture, this parylene-C layer 180 can be considered to be insulating layer 37 on the underside of frame 32 as seen in FIGS. 3 and 4.

An upper frame plate 192 is then disposed over the outer surface of the outer surface of the frame 32. Frame plate 192 is formed from a rigid, thermally conductive material such as aluminum. Openings 194 (one shown) are formed in frame plate 192. When the upper carrier plate 192 is seated on the alignment jig 182, pins 186 align to plate openings 192.

Figure 22:
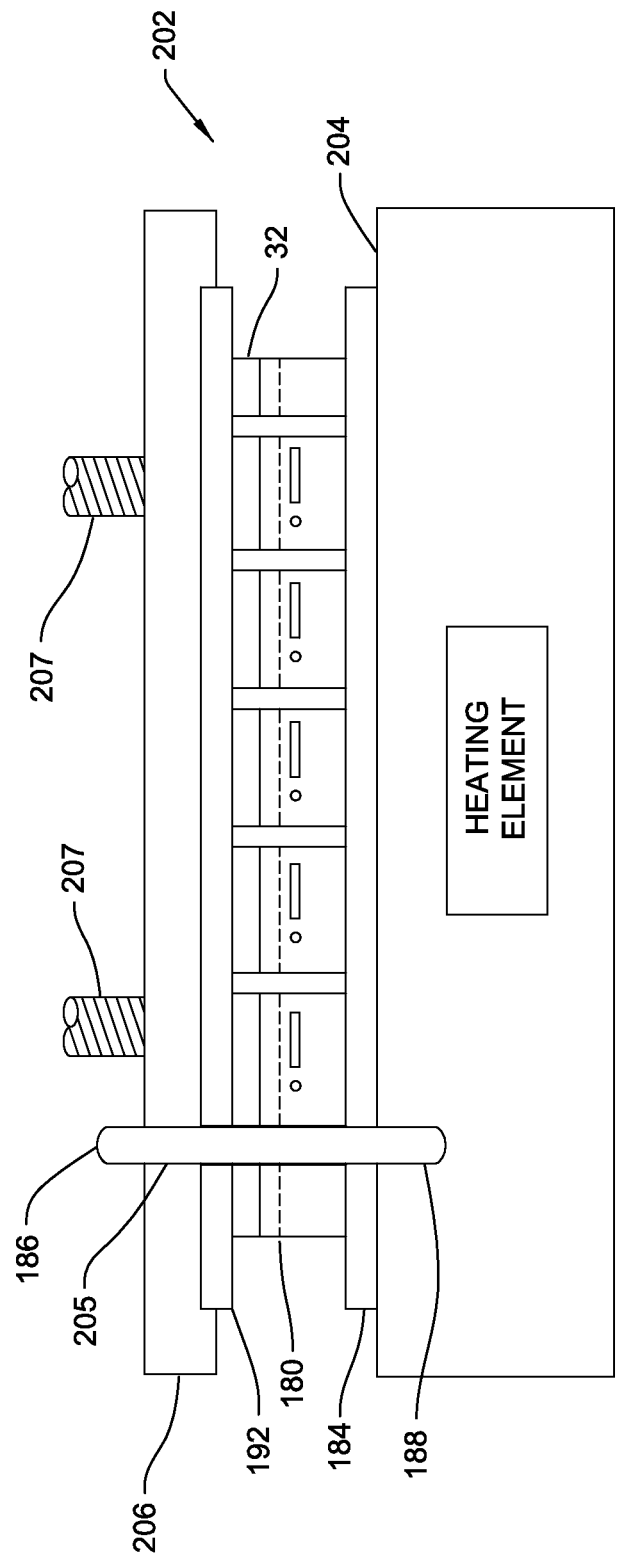
FIG. 22 depicts how the frame and substrate of this invention are positioned in a press assembly.

The lower carrier plate-substrate and electrodes-carrier-upper carrier plate assembly is then placed in a press unit 202, FIG. 22. During the transport process, pins 186 are part of this assembly and are used to hold the substrate-and-electrode assembly and the frame 32 in registration.

Press unit 202 includes a static platen 204 and an opposed moving platen 206. Closed end bores 188 extend from the exposed face of the static platen. Moving platen 206 is provided with through holes 205, (one shown) for receiving pins 186. Threaded drive rods 207 represent the mechanism integral with press unit 202 that move the moving platen 204 towards and away from the static platen. For reasons that are apparent below, the press unit 202 is disposed in a vacuum chamber.

The assembly holding the substrate and frame is positioned so that the exposed surface of the lower carrier plate 184 is seated against the static plate and the exposed surface of the upper carrier plate 192 is adjacent the moving plate 206. After the assembly is so positioned, the moving plate 206 is urged against the assembly so that a sufficient force is exerted to eliminate lateral slippage of the substrate-and-electrode sub-assembly relative to the frame 32. Pins 186 may then be removed from the press.

Figure 23:
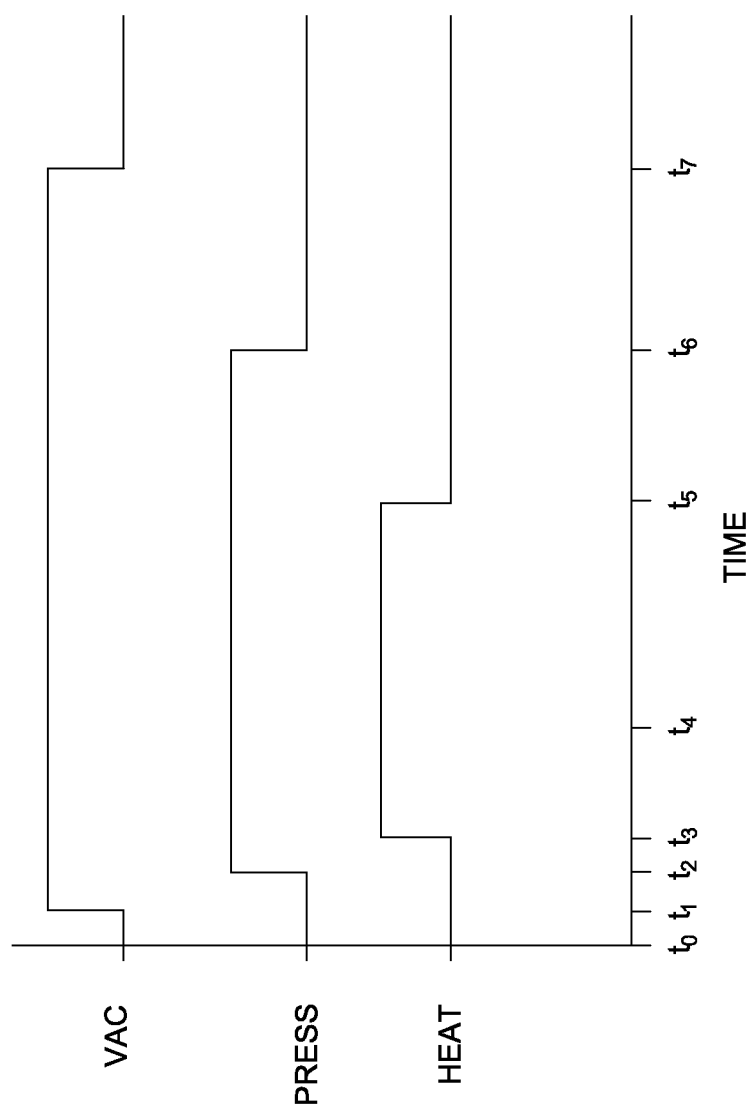
FIG. 23 is time line representing the stages of the press sequence.

The actual bonding process is now described by reference to the timing diagram of FIG. 23. Initially, the chamber housing press unit 202 with the stacked substrate and electrodes-frame is closed, time $t_0$. At time $t_1$, a suction is drawn on the chamber to form a vacuum down to at least 10 micro torr. In some methods of this invention, the suction is drawn to 5 micro torr or less. The suction is drawn to reduce the content of oxygen in the chamber. This reduces the likelihood that, in the later heating step, the parylene-C will oxidize. This oxidation, if allowed to occur, could place fracture-inducing stresses on the parylene or otherwise degrade the properties of the parylene. Force is then applied to the moving platen 206 so that this platen urges frame parylene-C layer 180 against substrate parylene-C layer 124, time $t_2$. In this process sufficient force is applied against the substrate and electrodes-frame assembly to create approximately 4-12 MPa of pressure between the two adjacent parylene layers.

After the pressure has been applied, at time $t_3$, the assembly is also heated to a temperature slightly above the glass transition temperature for the parylene-C but below the melting point. This temperature is between 150 and 320° C. This heating is performed by actuating a heating element 208 disposed in the static platen 204, time $t_3$.

It has been found that in one version of practicing this invention, it takes approximately 15 minutes once heating element 208 is actuated, for the temperature of the parylene-C layers 124 and 180 to rise to above the parylene-C glass transition temperature, the transition from time $t_3$ to time $t_4$. The actual time varies with the equipment used to perform the process. Once the parylene-C layers are in this state, the pressure causes these layers to form a uniform bond along the surfaces where they abut. As a consequence of the bonding of these parylene-C layers 124 and 180, the layers form the substrate 34 of the assembly 28. It has been found that, for a continuous bond between the parylene layers to form that can withstand shear without delaminating, the heat should be applied for approximately 30 minutes, time $t_5$. At this time, heating element 208 is deactivated.

As a consequence of the deactivation of heating element 208, the electrode array assembly cools to ambient temperature. The rate at which the assembly cools is regulated. This rate may be controlled by cycling the heating element (step not shown.) Alternatively, the insulation surrounding the enclosure in which the fixture is located is selected to have a thermal conductivity that limits the rate at which heat leaves the fixture.

The assembly is cooled at a relatively slow rate due to its geometry. Specifically, owing to the presence of the metal forming the electrodes 36, the conductive traces 38, and the conductive fans 39, during the step of applying pressure, the top platen 206 is not in contact with the whole of the top surface of the assembly. Thus, when the pressure is applied to the parylene-C, it is applied unevenly. This uneven application of pressure subjects the surface of the parylene to uneven stresses. After the heating of the assembly is terminated, the metal forming the electrodes 36, the conductive traces 38 and the conductive fans 39 cools more rapidly than the adjacent parylene. This differential cooling causes differential contraction of the elements of the assembly. Differential contraction causes mechanical stresses at the interfaces between these elements. To compensate for these differential contractions, the assembly is allowed to slowly cool. The slow cooling allow the parylene to slowly creep. These mechanical stresses can be mitigated, in part, if the rate of cooling is slowed to allow the parylene to creep. The creeping of the parylene results in the relaxation of these stresses.

When the temperature drops to 140° C. or below, time $t_6$, the pressure placed on the assembly 28 is backed off. The simultaneous release of pressure on the assembly while the parylene is allowed to creep further reduces the total stress on the assembly. This reduction in stress reduces the fracturing of the parylene that could otherwise occur.

After the pressure on the assembly 28 is backed off, the assembly remains under vacuum as its temperature continues to drop. When the temperature drops to approximately 80° C., time $t_7$, the assembly is ready for removal from the chamber in which it is fabricated. Immediately prior to this removal, the suction draw is terminated.

Figure 24:
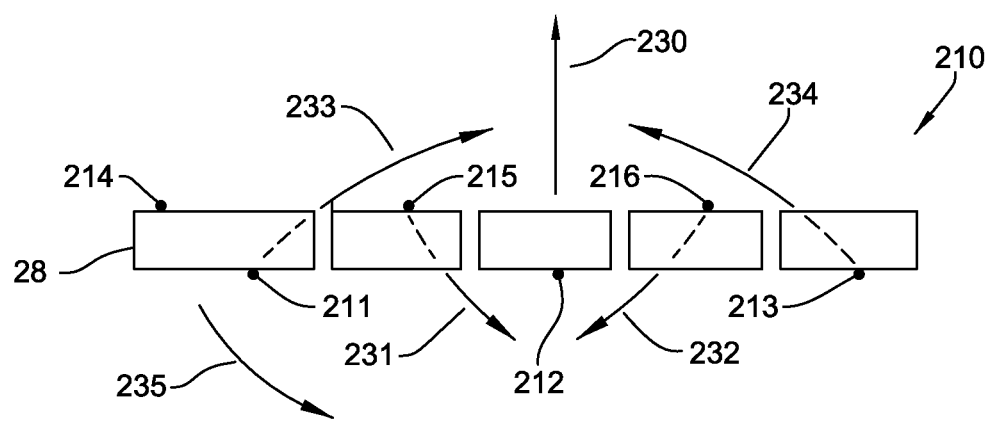
FIG. 24 depicts how the electrode array assembly is positioned between the wires of a folding loom and how the loom wires are displaced to fold the assembly.

Once electrode array assembly 28 is fabricated, other components such as antenna 44 and circuits 45 may be added to the assembly. Electrode array assembly 28 is then folded. In one method of this invention, the electrode array assembly is disposed in a folding loom 220, FIG. 24, that includes seven spaced parallel apart wires 211-216. Assembly 28 is sandwiched between lower wires 211, 212 and 213 and upper wires 214, 215, and 216. As a consequence of the placement of the electrode array assembly 28 in the folding loom 210, the assembly flexes outwardly from its curved shape to a planar shape.

As will become apparent below, the diameter of wires 211-216 establishes the radii of the folds of the electrode array assembly 28. The minimum radii of these folds need to be above the radius at which such folding imposes strains above the elastic limit for the material being folded. The critical material for some versions of this invention is the Nitinol forming the frame 32. Nitinol typically has an elastic limit of 10% strain. For an assembly having a Nitinol frame of 50 microns thickness, wires 211-217 should therefore have a minimum radius of 0.3 mm.

Also, the metals forming the electrodes 36, the conductive traces 38 and conductive fans 39 may be difficult to fold without being subjected to fracture inducing stresses. Accordingly, it is preferred that the assembly be fabricated so that the metals forming the electrodes 36, the conductive traces 38 and conductive fans 39 not be located over regions of the assembly that are subjected to the now being described folding process.

In addition to being sandwiched between the sets of wires 211-213 and 214-216, the electrode array assembly 28 is aligned so each column of electrodes 36 is generally positioned over or under one of the loom wires. Thus, loom wires 211, 212 and 213 are, respectively, disposed below the first, third and fifth columns of electrodes 36 of the assembly of FIG. 2. Loom wire 214 is disposed over the surface of the assembly opposite the surface against which wires 211-213 are disposed between loom wire 211 and the adjacent side edge of the assembly. Loom wires 215 and 216 are disposed on the same surface of the assembly over which loom wire 214 is disposed. Loom wires 215 and 216 are disposed, respectively, over the second and fourth columns of electrodes 36. While not required, in some methods of practicing this invention, the electrode array assembly 28 is positioned relative to the folding loom 210 so that the longitudinal axis of each column of electrodes is approximately, if not precisely, aligned with the associated loom wire 211, 212, 213, 215 or 216.

Once the electrode array assembly is positioned in the folding loom 210, the loom is actuated. In this process the loom wires 211-216 are simultaneously moved so as to fold the electrode assembly. Specifically, loom wire 212, the loom wire below the assembly 28 associated with the third column of electrodes is moved upwardly, represented by straight arrow 230. Wires 215 and 216 are moved in downwardly symmetric arcuate paths, represented by, respectively, arrows 231 and 232.

The wires associated with the first and fifth columns of electrodes, respectively wires 211 and 213, are moved in symmetric paths upwardly towards the plane in which wire 224 moves, represented by, respectively curved arrows 233 and 234. Wires 214 the wires immediately above and inward the left side outer perimeter of the electrode array assembly moves downwardly and inwardly toward the plane along which wire 212 travels as represented by curved arrow 235.

Collectively, the displacement of wire 211 and, on the other side of the assembly, wires 214 and 215 bend the assembly to form the first fold represented by dashed line 262 in FIG. 2. The displacement of wire 215, and on the other side of the assembly wires 211 and 212, bend the assembly to form the second fold represented by dashed line 264. The displacement of wire 212 and on the other side of the assembly 28, wires 215 and 216, bends the assembly to form the third fold, represented by dashed line 266. The displacement of wire 216 and, on the other side of the assembly 28, wires 212 and 213, bends the assembly to establish the fourth fold, represented by dashed line 268.

The presence of slots 54 and 61 selectively weaken the electrode array assembly along specific longitudinal axes. These are the axes with which the wires 211, 121, 215 and 216 are aligned when the assembly is placed on the loom 210. Accordingly, the material on the assembly along these axes essentially become folding axes along which the electrode array assembly is folded.

Figure 25:
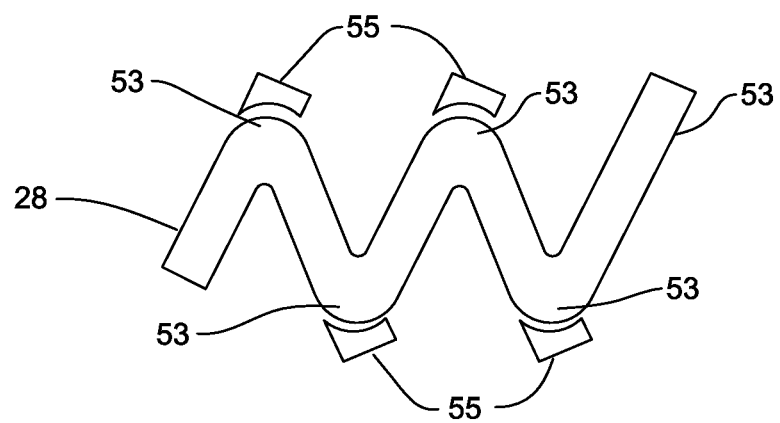
FIG. 25 depicts the folded electrode array assembly of this invention.

The actuation of folding loom 210 does not result in the whole of the electrode array assembly bending. The individual electrodes 36 are disposed on tabs 55 defined by slots 54. Accordingly, while the sections of the frame 30, the substrate 34 and outer shell 72 that form beams 53 between the tabs 55 bend, the tabs themselves do not bend. Instead each column of tabs essentially rotates, and to some extent translates around the loom wire 222, 224, 226, 230 or 232 with which the tab is aligned. Consequently, as depicted in the FIG. 25 the electrode-carrying tabs 55 and auxiliary tabs 62 do not bend to the extent the rest of the assembly 28 bends, is folded. These sections of the assembly substantially maintain their planar profile, (discounting the curvature of the assembly 28 as whole.)

Also, it should be understood that the loom 210 is constructed and the electrode array assembly is positioned so that foot 43 is not folded.

Further, while the exact method is not part of this invention, it should be understood that a part of the construction of electrode array is the formation of antenna 44 on foot 43 and the mounting of components 45 to the foot.

III. Insertion Tool

As a consequence of the assembly being folded, the assembly can be placed in the lumen of a cannula or introducer needle for percutaneous insertions. Thus, it has been found that an electrode array assembly of this invention that has width of approximately 7 mm can be folded into five sections, each of which include a column of electrodes 36 and fit in a cannula having a lumen of less than 3 mm in diameter at widest axis.

Figure 26:
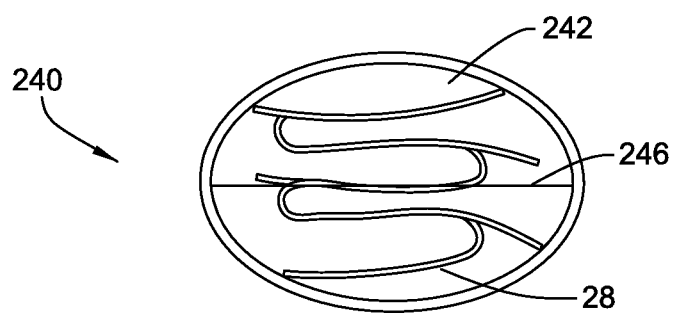
FIG. 26 illustrates how a folded electrode array assembly of this invention is disposed in a cannula.

A cannula, identified as deployment or inner cannula 240, used to insert electrode array assembly 28 against tissue internal to the body is illustrated in FIG. 26. Inner cannula 240 is formed from superelastic material that defines a lumen 242. Cannula 240 is shaped to have an elliptical or oval cross-sectional profile. Lumen 242 has the same profile as the body of the inner cannula 240. In FIG. 26 line segment 246 represents the major axis of cannula lumen 242, the widest diameter line across the lumen. Electrode array assembly 28 is fitted in the lumen so that the tabs 55 and 62 are in planes that are approximately parallel to the plane of major axis of the lumen 242.

Figure 28:
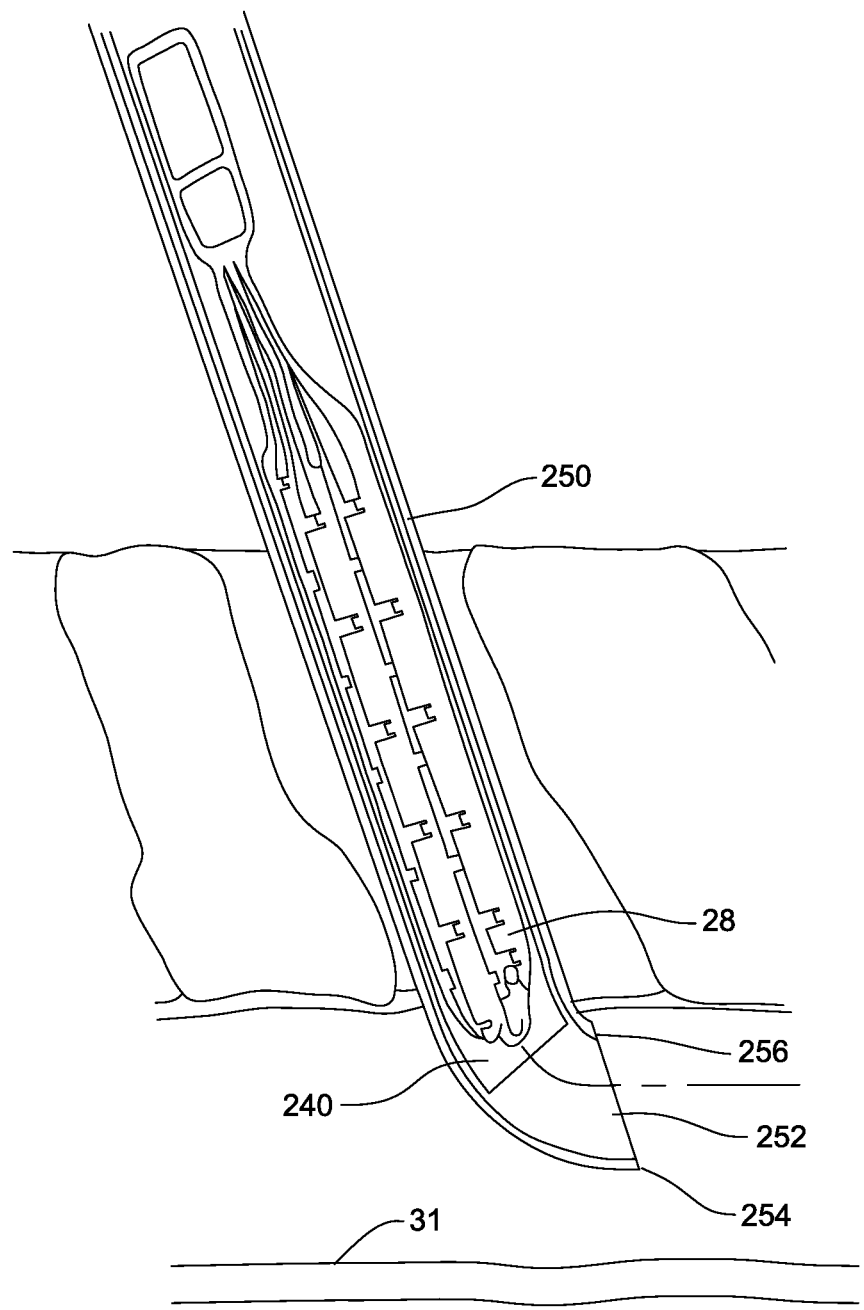
FIG. 28 is a cross sectional view of the tool and electrode array assembly of FIG. 27

To gain access to the epidural space and thereby facilitate fitting the electrode array assembly 28 against the tissue, the assembly comprising the inner cannula 240 with electrode array assembly 28 fitted therein is fitted into an access or outer cannula 250 as seen in FIG. 28. Outer cannula 250 has an anti-coring distal end opening. One such design is the Touhy-style tip. That is, the distal end opening of the cannula is not axially aligned with the longitudinal axis of the bore down the center the cannula. Instead, cannula 250 has an opening 252 that is centered around an axis that is angularly offset relative to the longitudinal axis of the lumen of the cannula. In the illustrated version of the invention these two axes are angularly offset by approximately 120°. This angle is exemplary, not limiting. The section of the distal end of the cannula around the most distal section of opening 252 is formed to have an outer edge 254 that is relatively sharp. This allows the cannula 250 to be inserted through tissue. The opposed end of the body of the cannula that defines the proximal end of opening 252 has a rounded surface 256. The presence of rounded surface 256 minimizes the extent to which the electrode array assembly 28, when being deployed is scored.

Figure 27:
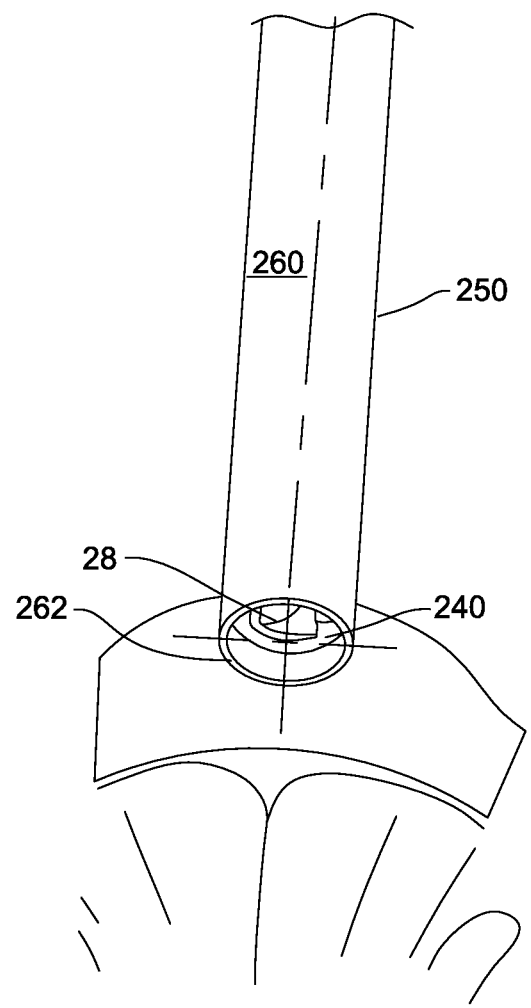
FIG. 27 depicts how the folded electrode array assembly disposed in the insertion tool comprising an inner cannula and an outer cannula.

Proximally rearward of opening 252, outer cannula 250 is shaped to have a body 260, seen in FIG. 27, with an elliptical or oval cross sectional profile at least in the section thereof in which the electrode array assembly is seated. As seen in FIG. 27 it should further be appreciated that the major axis of the lumen 251 of outer cannula body 260, like the major axis of the lumen 242 of inner cannula 240, is smaller in length than the width of the electrode array assembly 28 when the assembly is unfolded. The assembly comprising electrode array assembly 28 and inner cannula 240 is positioned in the outer cannula 250 so that, as seen in FIG. 28, in the outer cannula body 260 the major axis of the inner cannula is aligned with the major axis of the outer cannula. This process is performed before the actual insertion of the inner cannula into the patient.

Figure 29:
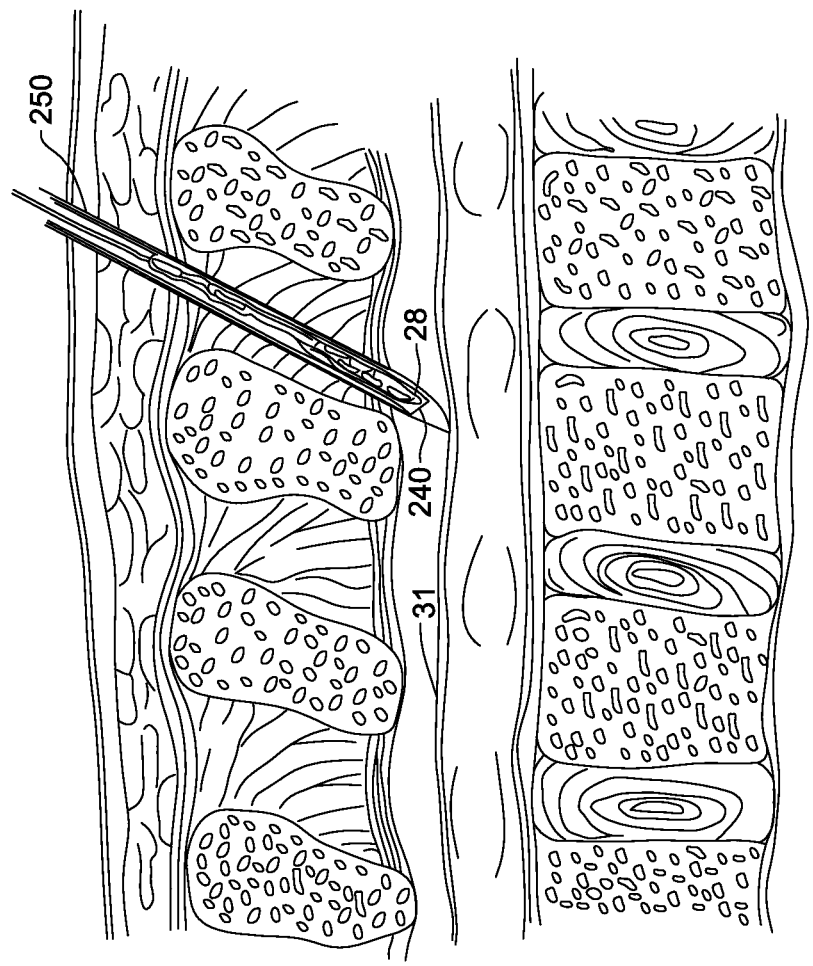
FIG. 29 is a side view illustrating the initial placement of the insertion tool, with the electrode array assembly disposed therein adjacent a section of the spinal cord dura against which the assembly is to be positioned.

Once the components are assembled together as described above, the distal end of the outer cannula 250 is inserted into the body of the patient. Cannula edge 254 functions as a knife edge that cuts through the tissue. Outer cannula 250 is positioned so that opening 252 is above the surface against which the electrode array assembly is to be positioned. In FIG. 29, the outer cannula is shown positioned sliced through interspinus ligaments between two vertebras. Outer cannula opening is in the epidural space above the surface of the dura 31 over which the electrode array assembly 28 is to be deployed.

Figure 30:
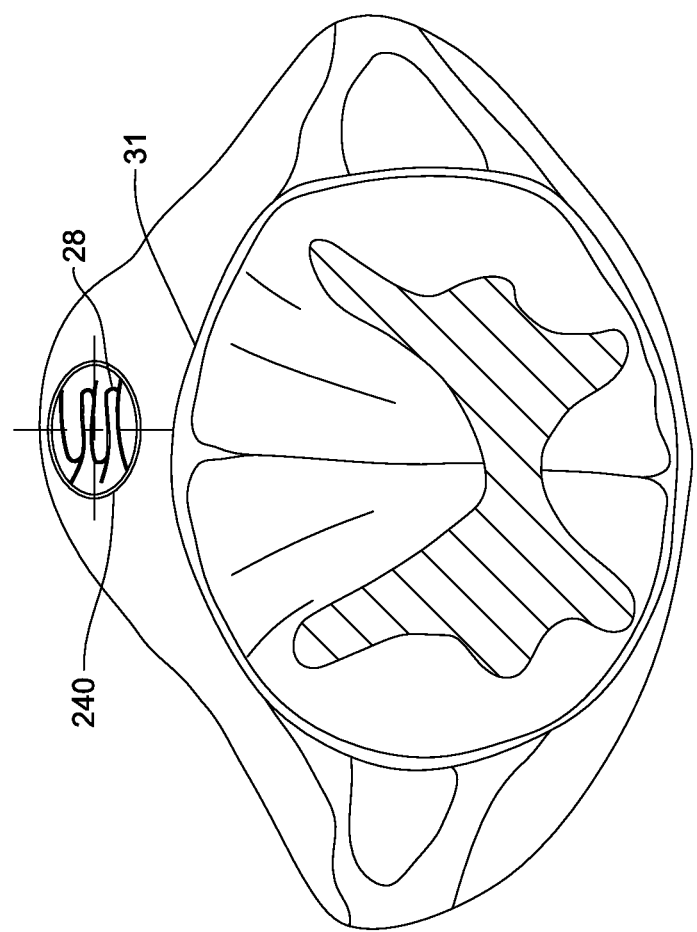
FIG. 30 is a cross sectional view of tool and electrode array assembly illustrating the orientation of the assembly relative to the surface of the dura against which the assembly is to be positioned.

When assembly 28 is in the above position, a pre-deployment position, the orientation of the assembly relative to the surface of the dura is as seen in FIG. 30. Specifically it can be seen that the individual folds of the assembly 28 are approximately parallel to the surface of the dura against which the assembly is to be deployed. If the assembly where allowed to be deployed, unfold, in this orientation, the assembly would expand in the epidural space between the dura and the inner surface of the overlying vertebra. Deployment along this plane would not result in the electrodes 36 being oriented toward the surface of the dura 31.

Figure 31:
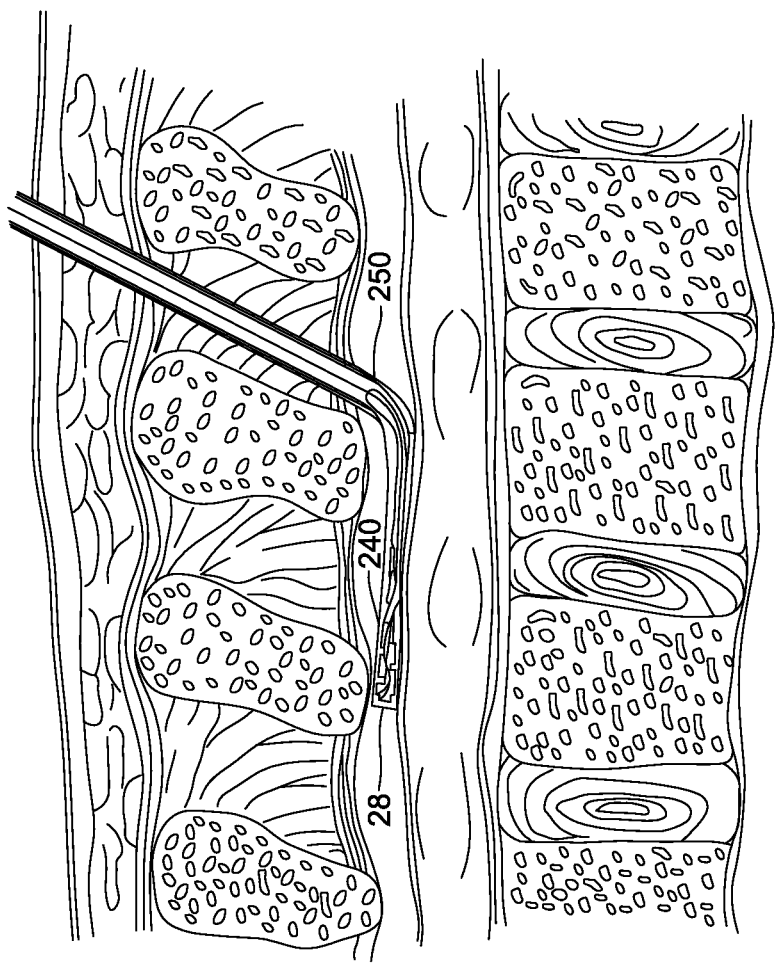
FIG. 31 is a side view illustrating the longitudinal advancement of the inner cannula and electrode array assembly out of the outer cannula.

Inner cannula 240, with the electrode array assembly 28 contained therein, is then pushed forward out of outer cannula opening 252 as seen in FIG. 31. To be so discharged, the electrode array assembly 28-and-cannula 240 assembly moves along a path of travel that curves in the transition from the axis of the body outer cannula 250 to the axis of outer cannula opening 252. Owing to the relatively thin profile of the electrodes, the conductive traces and the conductive fans and the relatively large radius of the curve along which the electrodes travel, these components are not subjected to significant bending as they travel this curved path. Since no component is so bent, the possibility that such bending would cause fracture of the components forming the electrode array assembly is substantially eliminated.

With respect to the described electrode array assembly 28, it is believed that the radius of the curve around which it travels should be at least 1 mm.

Figure 32:
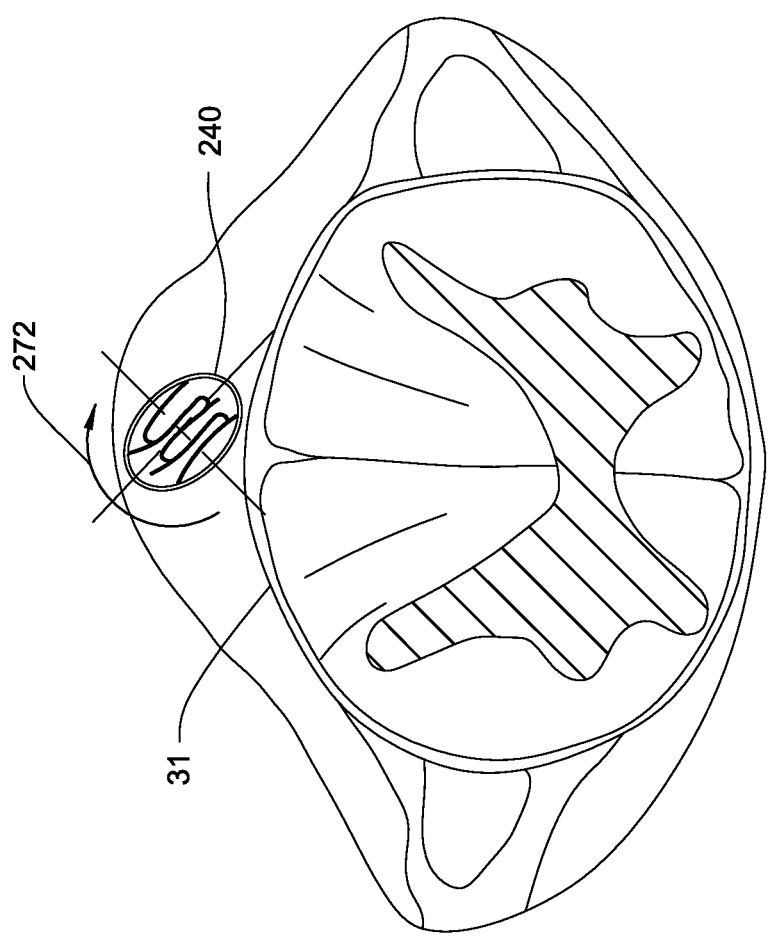
FIG. 32 is a cross sectional view illustrating the rotation of the inner cannula and electrode array assembly contained therein toward the deployed orientation.
Figure 33:
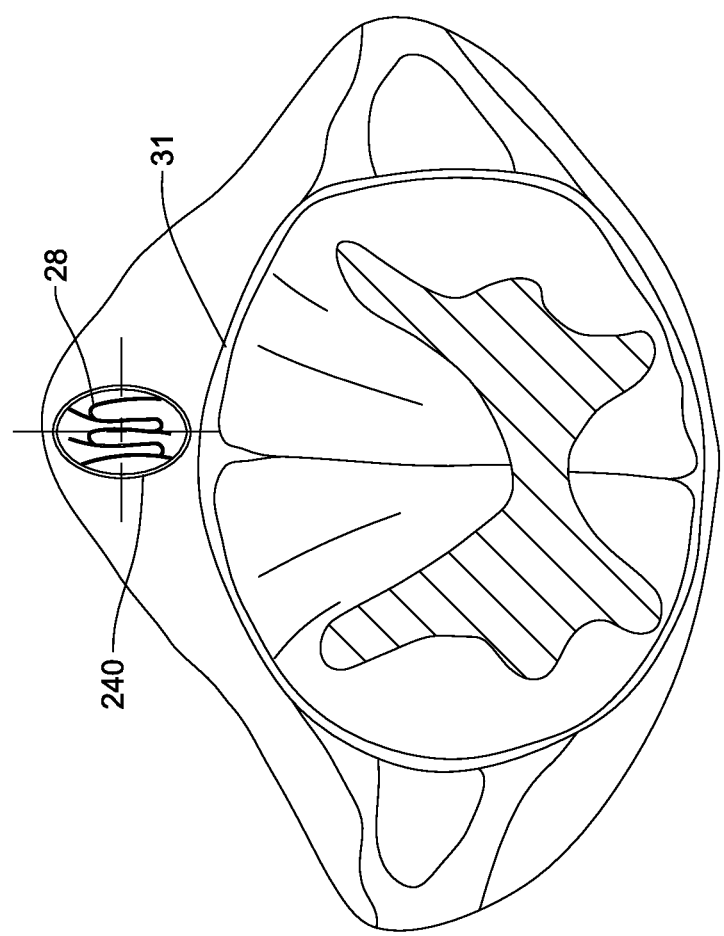
FIG. 33 is a cross sectional view illustrating the inner cannula and electrode array assembly contained therein fully rotated to the deployed orientation relative to the surface of the dura against which the electrode array assembly is to be deployed.

Once the inner cannula 240, with the electrode array assembly 28 contained therein starts to be pushed out of the outer cannula 250, the continued ejection of the inner cannula is accompanied by the simultaneous rotation of the cannula 250. As represented by curved arrow 272 of FIG. 32, the inner cannula 240 with the electrode array assembly 28 contained therein, is rotated 90°. As a consequence of this rotation, sequentially depicted by FIGS. 30, 32 and 33, it can be seen that folds of the electrode array assembly 28 are in planes that are generally perpendicular to the surface of the tissue against which the assembly is to be placed.

To facilitate the proper orientation of the inner cannula 240 during the deployment process, the cannula may be initially formed in a twisted shape. Specifically, inner cannula 240 may be shaped so that the major axis 246 of the cannula lumen 242 rotates around the proximal end-to-distal end longitudinal axis through the lumen. When inner cannula 240, with assembly 28 disposed therein is initially fitted in the outer cannula 250, the inner cannula is constrained in an untwisted shape. Thus, upon advancement of the inner cannula 240 out of the outer cannula 250, the inner cannula is free to rotate to the twisted shape. As a consequence of both this twisting of the cannula 240 to its formed shape and the twisting of the cannula 240 by the practitioner, the inner cannula 240 assumes the orientation relative to the dura 31 of FIG. 33. Inner cannula 240 and therefore the electrode array assembly 28 are thus properly aligned for assembly deployment over the dura 31.

Figure 34:
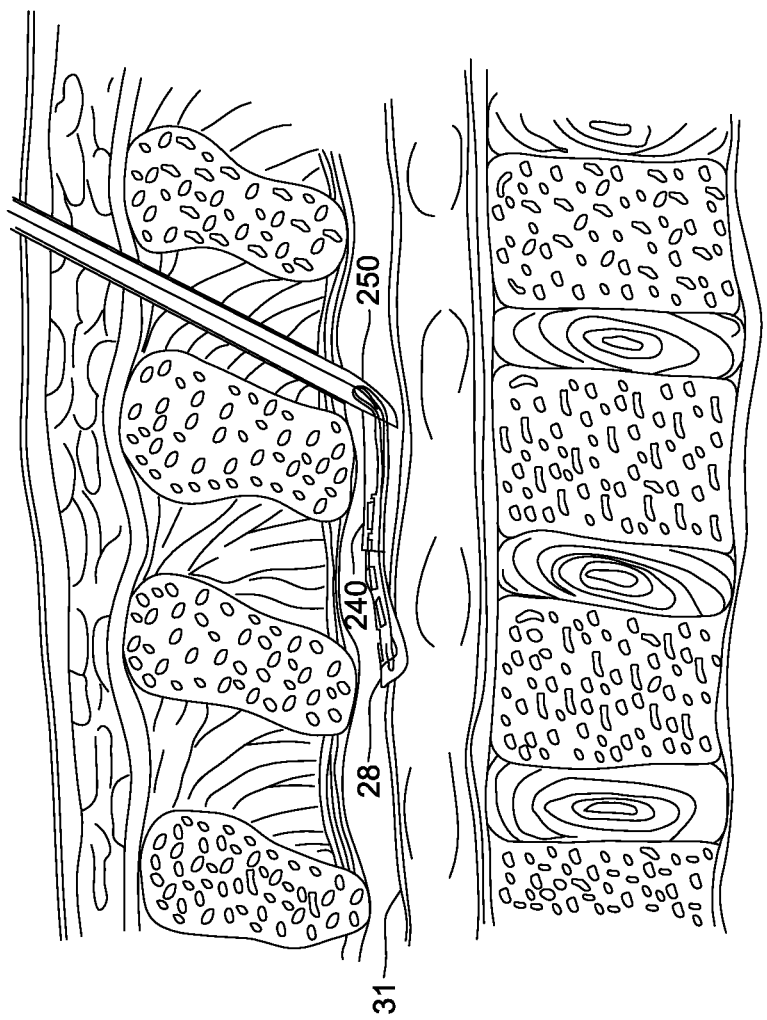
FIG. 34 is a side view illustrating the retraction of the inner cannula back into the outer cannula so as to result in the deployment of the electrode array assembly over the dura.

Once the electrode array assembly-and-inner cannula assembly is in the position, the inner cannula is at least partially retracted back into the outer cannula 250, represented by FIG. 34. While the inner cannula is so retracted, the electrode array assembly 28 is held in its position relative to the outer cannula 250. In one version of practicing this invention, electrode array assembly is held in place by inserting a rod down the inner cannula lumen 242. The inner cannula 242 is retracted over the rod. The abutment of the foot 43 of the electrode array assembly against the rod prevents the retraction of the electrode array assembly 28.

Alternatively, guide wires attached to the electrode assembly head 40 restrain the assembly 28 from retracting with the inner cannula 240. As long as the guide wires are constrained in the inner cannula 240, the guide wires are have some resistance to buckling. This resistance to buckling allows the wires to serves as members for restraining the electrode array assembly 28 as the inner cannula 240 is retracted. Once the electrode array assembly is deployed, the guide wires can be used to make adjustments in the position of the assembly 28. During these position adjustments, the curved shape of the assembly head 35 allows the assembly to be advanced forward. After the assembly 28 is positioned, the wires are worked free from the assembly and retracted out through the inner and outer cannulae 240 and 250, respectively.

As a consequence of the inner cannula 240 retracting away from the electrode array assembly 28, the assembly 28 is free from the physical constraint of the cannula 240. Owing to the superelasticity of the frame 30, the electrode array assembly unfolds, deploys, to its preformed curved shape. Again, prior to deployment, the assembly is oriented so that its folds are generally perpendicular to the surface of the dura 31 against which it is to be deployed. The frame 32, and therefore the whole of the assembly 28 unfolds along an axis perpendicular to the planes of the folds. Owing to the orientation of the assembly 28, the assembly's unfolding axis is parallel to the surface against which the assembly is to be positioned. Due to the pre-formed curved shape of the electrode array assembly 28, the assembly, when unfolded, thus conforms to the surface of the dura 31.

In some deployments of the assembly 28, the assembly is laterally supported by the tissue against which it is disposed. This support holds the assembly 28 to the tissue.

Electrode array assembly 28 is then available to apply current to selected sections of tissue below the assembly. Once the assembly is positioned, the practitioner can, by experimentation, determine through which electrodes 36 the current should flow in order to have the desired therapeutic effect. Since the electrodes are in a row by column arrangement over the tissue, the practitioner has a wide range of options of the sections of tissue through which the current can be applied. Thus, the current can be applied through the tissue that: located under a single column of electrodes; located under a single row of electrodes; located under plural rows and/or columns of electrodes; or located between wide spaced apart electrodes. The ability to establish a current flow path from multiple available current flow paths increases the likelihood that the practitioner will be able to establish current flow through the tissue that has both desired therapeutic effects and minimal side effects.

Electrode array assembly 28 of this invention is designed so that the individual electrodes 36 are spaced apart a distance that maximizes the likelihood that adjacent electrodes, though closely packed together, will, when implanted against tissue, be substantially electrically isolated from each other. This electrical isolation of the electrodes minimizes the likelihood that a significant current will flow between two adjacent electrodes. These unintended current flows, if allowed to develop, could result in the inefficient delivery of current pulses to the nerves.

Electrodes 36 are relatively densely packed on the frame 32. As mentioned above, in some preferred versions of the invention, the electrodes in some of the columns are laterally offset from the electrodes in other columns. These features increase the spatial resolution of the current flow paths through the dorsal column nerve tissue the practitioner has available to establish. The increase in this spatial resolution improves the ability of the assembly to pulse current through the nerve tissue that will result in an optimal therapeutic effect. Further, this increased spatial resolution minimizes the extent to which the current is pulsed through nerves in which such current flow has either minimal or potentially adverse clinical effect. The reduction in this current flow improves the electrical efficiency of the implanted assembly 28.

While electrodes 36 are closely packed together, the individual electrodes 36 are spaced apart a distance that maximizes the likelihood that adjacent electrodes, when implanted against tissue, will be electrically isolated. This electrical isolation of the electrodes 36 minimizes the likelihood that a significant current will flow between two adjacent electrodes. These unintended current flows, if allowed to develop, reduce the spatial resolution of the current flow paths.

Another feature of the electrode array assembly 28 of this invention is that the signal applied to each electrode 36 is applied through the associated conductive fan 39. The conductive fan 39 provides a low impedance path to the electrode 36 along one of the longitudinal edges of the electrode 36. This low impedance path minimizes variations in charge delivery distribution over the surface of the electrode 36.

Electrode array assembly 28 of this invention is further constructed so that the gold of the electrodes 28 is not the actual material that forms the surfaces from which the current is applied to the tissue. Instead, the iridium heads 90 of the conductive buttons 86 define the surfaces through which the current is applied. A benefit of this feature of the invention is that iridium heads form a low impedance interface with the tissue in comparison to the path through a gold interface. This low impedance path minimizes the power loss. Further, iridium has a relatively high charge carrying capacity, in comparison to other noble metals. This high charge carrying capacity serves to minimize the likelihood that at some current levels the conductive capabilities of the electrode will start to decay.

In this version of the invention, the iridium is fabricated as part of the electrodes 36 as layers of the conductive buttons 86. By segmenting the iridium into the small heads, the likelihood that the iridium, when subjected to the mechanical stresses of folding, rolling, being deployed, or post-implantation flexure, will separate from the rest of the electrode is appreciably reduced.

Further, the segmenting of the iridium into the conductive buttons allows the outer shell 72 to hold the iridium to the rest of the assembly.

It also should be appreciated that the material in the epidural space in which assembly 28 is deployed has widely varying impedances. In some regions, this material can have a relatively high impedance. Current driven through this material can result in a loss of power. In a nearby region, the material above the tissue to which the current is to be applied can have a relatively low impedance. Current driven through this material can cause the current to spread beyond the target tissue. This current spreading reduces the spatial resolution of the current pulses. Collectively, the relative proximity of this high impedance and low impedance material to each other can make it difficult to establish current flow paths that will result in the desired clinical effect.

Assembly 28 of this invention when deployed unfolds to a curved shape. This curvature causes the assembly to conform to the surface of the underlying dura 31. This conformance reduces the distance between the conductive buttons 85 and the dura 31. The extent to which the current is driven through this layer of material with varying impedances is therefore likewise reduced. Accordingly, the adverse effects of the variable impedance of this material are similarly abated.

Further, the conformance of the electrode array assembly 28 to the underlying tissue provides the assembly with a relatively high degree of stability on the tissue. This stability reduces the likelihood that once implanted, the assembly will slip or otherwise become dislodged from its intended deployed position.

IV. Alternative Electrode Array

FIGS. 35 and 36 illustrate an electrode array assembly 290 constructed in accordance with this invention. Electrode array assembly 290 is designed to be disposed against a section of tissue. For example, assembly 290 may be curved so as to be disposed over a section of the spinal cord dura 31 (FIG. 1). Assembly 290 includes a number of individual electrodes 292. Electrodes 292 are selectively tied to the current sources and current sinks. When the current sources and sinks are actuated, current flows from one or more electrodes 292 tied to the current source or sources through regions of the tissue that underlies the assembly 290 to the one or more electrodes 292 tied to the current sink or sinks. A drive module 294 selectively ties the electrodes 292 to the current sources and current sinks. Drive module 294 is located at the proximal end of the assembly. (Here, "proximal" means towards the end of the assembly at the bottom of FIG. 35; "distal" means towards the end of the assembly at the top of FIG. 35).

In FIG. 35, assembly 290 is shown active side up so the electrodes 292 and drive module 294 can be seen. The "active" side of the assembly 290 is the side of the assembly on which the electrodes 292 are located. Opposite the active side, assembly 290 has a "passive" side.

In FIG. 36, drive module 294 is removed from the assembly 290 so the terminal pad 296 at the proximal end of the assembly can be seen. Terminal pad 296 is the substrate of the assembly 290 to which drive module 294 is attached. In many versions of the invention, the components forming assembly 290 are dimensioned so that drive module 294 extends rearwardly beyond the proximal end of terminal pad 296.

Three parallel, spaced apart bridges 302, 304 and 306 extend distally forward from terminal pad 296. The outer two bridges, bridges 302 and 306, are each formed with a leg, legs 308 and 310, respectively. Legs 308 and 310, which are coaxial, extend outwardly from opposed side edges of terminal pad 296. Bridges 302 and 306 extend perpendicularly forward, distally forward, from legs 308 and 310, respectively. Feet 312 and 314, respectively, connect legs 308 and 310 to terminal pad 296. Each foot 312 and 314 has a proximal end edge that tapers distally forward as the foot extends away from the adjacent side edge of terminal pad 296. Bridge 304, the center located bridge, extends forward from the distal end of terminal pad 296. Bridges 302, 304 and 306 thus have longitudinal axes (not identified) that extend from the opposed proximal and distal ends of the array 290.

Plural tabs 318 extend outwardly from the longitudinal axis of each bridge 302, 304 and 306. More particularly, at a number of spaced apart locations along the length of each bridge 302, 304 and 306, two tabs 318 extend outwardly from the opposed sides of the bridge. At least in the version of the invention depicted in FIG. 35, the tabs 318 are arranged in diametrically opposed pairs relative to the bridge 302, 304 or 306, from which the individual tabs extend. Electrode array assembly 290 is further constructed so that at each longitudinal section on bridge 302 tabs 318 extend, tabs 318 also extend from the laterally adjacent longitudinal sections of bridges 304 and 306. Thus, in the illustrated version of the invention, tabs 318 are arranged in rows wherein two tabs extend outwardly from each bridge 302, 304 and 306. The rows of tabs 318 are longitudinally spaced apart from each other. In some versions of the invention, the separation between the distal end of one row of tabs and the proximal end of the distally adjacent row of tabs is between 1 to 10 mm. In many versions of the invention, this separation is between 2 and 6 mm.

Each tab 318 is generally in the form of a rectangle with rounded corners. Each tab 318 has a length (measurement in the axis parallel to the longitudinal axis of the assembly of between 0.5 to 5 mm. Often this length is between 2 and 4 mm. Each tab 318 has a width, (measurement along the axis perpendicular to the longitudinal axis of the assembly) of 0.25 to 2 mm. In many versions of the invention, this width is between 0.5 to 1 mm. An advantage of providing electrodes with these dimensions is that it both provides a relatively dense package of electrodes while eliminating the need to provide conductors so numerous they must be located on multiple substrates. It should further be understood that each tab 318 attached to one bridge 302 or 304 is separate from the adjacent tab 318 attached to the adjacent bridge 304 or 306. The spacing between the adjacent tabs extending from adjacent bridges is typically no more than 500 microns and preferably 100 microns or less. This small separation between adjacent tabs reduces the amount of tissue that can grow between the tabs 318. If appreciable tissue were allowed to grow between the tabs 318, this tissue could inhibit later removal of the assembly 290.

Bridges 302, 304 and 306 are each shaped so that the width of the bridge between two adjacent pairs of tabs 318 is greater than the width of the same bridge between the distally adjacent next pair of tabs. Thus, the width of bridges between the first pair of tabs, the pair closest to drive module 294, and the adjacent pair of tabs is approximately 0.88 mm. The width of the bridges between the second and third pairs of tabs, (the pairs second and third closest to drive module 124) is approximately 0.80 mm. The width of each bridge between the eighth pair of tabs 318 and the adjacent ninth pair of tabs, the distal pair of tabs 318, is approximately 0.32 mm.

Beams 320 extend between the bridges 302, 304, and 306. More particularly, each beam 320 extends between adjacent bridges 302 and 304 or between adjacent bridges 304 and 306. In the illustrated version of the invention, assembly 290 is further constructed so that each beam 320 connecting bridges 302 and 304 is collinear with an adjacent beam connecting bridges 304 and 306. Each beam 320 has a width, (measurement along the axis parallel to the longitudinal axis of the assembly 290) of approximately 0.25 mm.

The electrode array assembly 290 of FIG. 35 is further constructed so that there is a pair of collinear beams 320 adjacent the proximal and distal ends of each of the tabs 318 in each row of tabs. Thus, in the illustrated version of the invention there are 18 pair of beams that connected the spaced apart bridges 302, 304, and 306 together. While the beams 320 are adjacent tabs 318, it should be understood that the beams are spaced apart from the tabs.

Given the spacing between the tabs 318, it should be appreciated that the longitudinally adjacent pairs of beams 320 are spaced apart from each other along the longitudinal axis of electrode array assembly 290. As discussed below, a flexible membrane 322 is disposed between these adjacent spaced apart beams 320. In FIG. 36 membranes 322 are shown by surface shading. Similarly, there are also membranes 324 located on the outer sides of bridges 302 and 306. Each of the membranes 324 extends between each a pair of longitudinally adjacent tabs 318 that extend from the outer sides of bridges 302 and 306. It should be appreciated though there are no membranes between the beam the tabs 318 and the adjacent beams. Instead, around the outside of each tab 318 that extends inwardly from bridges 302 and 306 and from both sides of bridge 314 there is a three-sided slot (not identified).

Electrode array assembly 290 is also formed to have a head 326 and two shoulders 340. Head 326 is located forward from a small neck 328 that forms the distal end of center-located bridge 304. Thus, neck 328 is located forward of the two distal most tabs 318 that extend outwardly from bridge 304. Each of the two distal most beams 320 extend from neck 328. Head 326 is located forward of the two distal most beams 320. Head 326 has a proximal edge that extends laterally beyond neck 328 on either side of the neck. The head 326 has two parallel side edges. At the most distal end, head 326 has an outwardly curved distally-directed front edge.

Each shoulder 340 extends forward from a small land 342 located forward of the associated outer bridge 302 or 306. Each land 342 is integral with and extends distally forward from the outer tab 318 integral with the bridge 302 or 306 with which the land is attached. Lands 342 serve as the terminuses for the beams 320 that extend from neck 328. Each shoulder 340 is spaced forward and away from the adjacent beam 320. Shoulders 340 are also spaced laterally away from the adjacent side edges of the head 326. Specifically, the shoulder 340 on the left side of FIG. 35 is spaced from the adjacent head side edge along a line that is collinear with the line along which the tabs 318 associated with bridge 302 are spaced from the adjacent tabs 318 associated with bridge 304. Similarly, the shoulder 340 on the right side of FIG. 35 is spaced from the adjacent head side edge along a line collinear with the line along which the tabs associated with bridge 304 are spaced from the adjacent tabs 318 associated with bridge 306.

Each shoulder 340 is approximately in the shape of a right angle triangle wherein the 90° corner is located adjacent the bottom of the adjacent side of edge of the head 326. The hypotenuse edge of the shoulder 340 is the outer edge of the shoulder. Each shoulder 340 is, however, further shaped to have a rounded distal end 344.

A beam 346 connects the hypotenuse of each shoulder 340 to the top of head 326. Each beam 346 extends from an outer extension of the associated shoulder forward and inwardly. Thus, each beam 346 is spaced forward from the distal end 344 of the associated shoulder 340 and curves inwardly over the adjacent side of the front edge of head 326. The inner end of each beam 346 is connected to a small nose 347 that extends forward from the most forward edge of head 326. Thus, between each shoulder 340 and associated beam 346 there is a small void space (not identified) that generally has the shape of an arrow head. Immediately to the side of nose 347 there is a small curved slot (not identified) between each beam 346 and the adjacent distal end edge of the head 326. This slot is contiguous with the void space between the beam 346 and the adjacent shoulder 340.

An electrode 292 is disposed on each one of the tabs 318. Plural conductors 348 are disposed on bridges 302, 304 and 306. Each conductor 348 extends to a separate one of the electrodes 292 integral with the associated bridge 302, 304 or 306. In FIG. 35, due to scale, the set of conductors on each bridge is seen as a single black line. The thickness of this line decreases distally along the length of each bridge. This decrease in line thickness represents that, moving distally along each bridge 302, 304 or 306, the number of conductors present on the bridge decrease. Conductors 348 are the conductors over which current is sourced to or sunk from the electrodes 292. If an electrode 292 does not function as a current source or sink, the electrode may function as a voltage probe. When an electrode 292 performs this function, the associated conductor 348 serves as the conductor over which the sensed voltage is connected to the monitoring circuit.

Each conductor 348 only extends as distally forward as the electrode 292 to which the conductor is connected. Adjacent the associated electrode, each conductor fans out to have a width (the dimension along the line parallel to the longitudinal axis of the array 290) that is substantially equal to the length of the electrode 292. Each bridge 302, 304 and 306 therefore supports more conductors adjacent its proximal end than its distal end. This need to support the largest number of conductors adjacent the proximal ends of the bridges 302, 304 and 306 is why these ends of the bridges are wider than their complementary distal ends.

Figure 37:
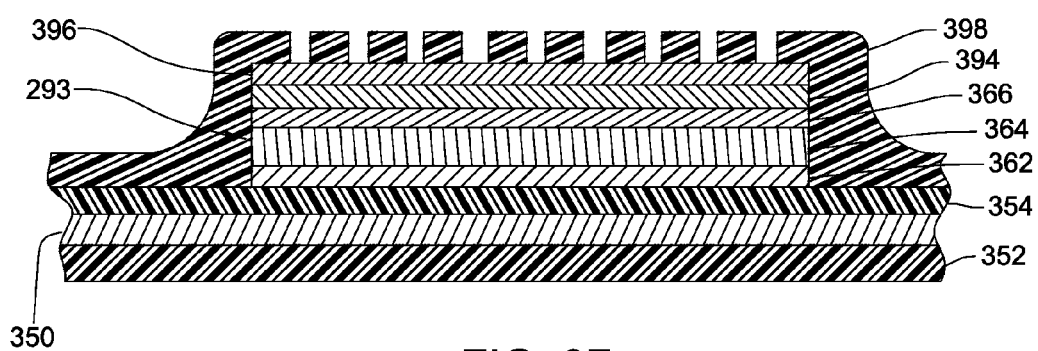
FIG. 37 is a cross sectional view across the width of a single electrode of the assembly of this invention.
Figure 38:
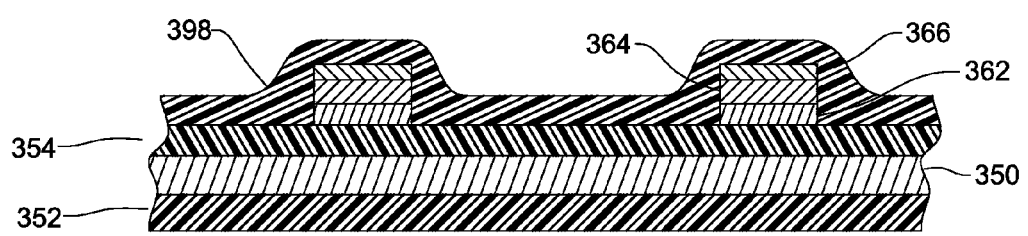
FIG. 38 is a cross sectional view across two conductors of the assembly of this invention.

Electrode array assembly 290, as seen in FIGS. 37 and 38 has a frame 350 formed from the same superelastic material from which frame 30 of the first described electrode array assembly of this invention is formed. In some versions of the invention, frame 350 has a thickness between approximately 25 and 100 microns. Frame 350 is shaped to form the basic geometric features of the assembly including bridges 302-306, legs 308 and 310, feet 312 and 314, tabs 318, beams 320 and 346, head 326, neck 328, shoulders 340 and lands 342. However, as discussed below, frame 350 does not serve as a substrate for terminal pad 296. Similarly, membranes 322 and 324 are formed from material different from which the frame 350 is formed.

Figure 39:
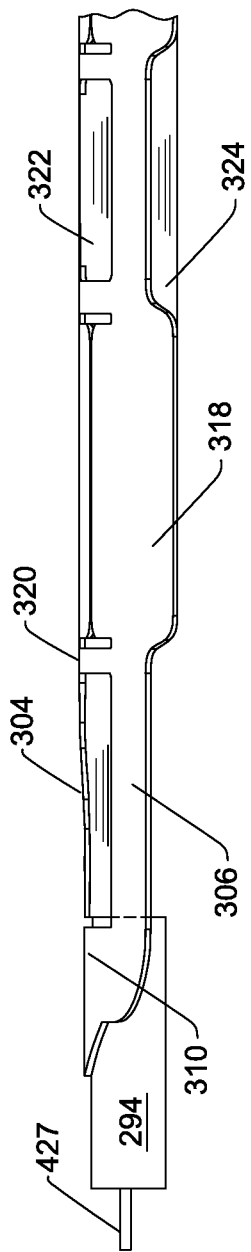
FIG. 39 is a side view of the proximal end of the electrode array assembly showing how the assembly has a curved profile.

Frame 350, like frame 30, may be curved early in the processes of manufacturing assembly 290. Often the arc of curvature is perpendicular to the longitudinal axis of the assembly 290. In these versions of the invention, this means that when a manufactured assembly 290 is placed on a flat surface, with the electrodes 292 facing downwardly, center bridge 304 is elevated relative to side bridges 302 and 306 as seen in FIG. 39. More particularly, FIG. 39 illustrates the elevation of center bridge 304 relative to bridge 306.

It can further be seen from FIG. 39 that when the frame 350 is so shaped, legs 308 and 310 and feet 312 and 314 may not be curved to the extent the rest of the frame is curved. Also, the proximal end of bridge 304, the end proximal to the proximal most beams 320 may be bent downwardly. This further shaping of the frame 350 is to ensure that the terminal pad 296, which extends from the proximal end of bridge 304 and feet 312 and 314 is a planar structure.

Insulating material, parylene-C, is disposed on the top, bottom and side surfaces of the frame 350 (side-located insulating material not shown). This insulating material is disposed over the surfaces of the frame 350. In FIGS. 37 and 38, the insulating material disposed over the surface of the frame 350 away from the tissue against which the assembly 290 is employed, is identified as passive side insulating layer 352. Insulating layer 352 has a thickness of approximately 1 to 20 microns. In many versions of the invention, the insulating material of layer 352 has a thickness of approximately 5 to 15 microns. Passive side insulating layer 352, in addition to being disposed over the "passive" side of frame 350 is also disposed over the side edges of the frame 350. The coating forming the passive side insulating layer 352 also extends beyond the side edges of the frame 350.

The insulating layer disposed over the surface of the frame 350 on which electrodes 292 and conductors 348 is located is identified as the intermediate insulating layer 354. Intermediate insulating layer 354 has a thickness in the range of the thickness of passive side insulating layer 352. The material forming intermediate insulating layer 354 also is located in the area bordered by the proximal end of bridge 304 and feet 312 and 314. In this area, the material forms a passive side layer 356 of terminal pad 296, seen in FIG. 40. This passive side insulating layer 356 is formed with a number of openings 358, one opening 358 seen in FIG. 40.

During some methods of manufacturing, the material forming the passive side insulating layer 352 and the intermediate insulating layer 354 are applied in a single step. These insulating layers 352 and 354 form a continuous coating around frame 350.

Conductive traces that form base pads 293 for the electrodes 292, and the whole of the conductors 348 are disposed on the exposed surface of intermediate insulating layer 354. Typically, each conductive trace includes a thin layer of titanium 362 applied directly to intermediate insulating layer 354. Layer 362 typically has a thickness of 100 to 1000 Angstroms. A thicker layer of gold 364 is disposed over titanium layer 362. The gold layers 364 that form the electrode base pads have a thickness of 1 to 15 microns, typically 8 to 12 microns. The gold layers 364 that form parts of the conductors 348 have a thickness of 1 to 3 microns. A thin outer layer of titanium 366 is disposed over the surface of the exposed surface of gold layer 364. Titanium layer 366 has a thickness approximately equal to that of titanium layer 362. Titanium layers 362 and 366 and gold layer 364 function as the low resistance conductive assembly of the conductive traces. However, titanium is relatively brittle. Gold is more ductile. Therefore, to reduce the likelihood of conductor breakage due to bending, the layers of the titanium are kept relatively thin. Titanium layer 362 is provided to strengthen the bond between the gold to the intermediate insulating layer 354. Outer titanium layer 366 is provided to strengthen the bond of the below-discussed active side insulating layer 398 to the gold layer 364. The outer titanium layer 366 is also provided to facilitate the bonding of the outer metal layers that form the individual electrodes 292.

Where this titanium/gold/titanium laminate is formed to function as a conductor 348, the laminate has a trace width of approximately 1 to 100 microns. Often this trace has a width between 20 to 50 microns. It has been found that a trace having this width offers a low-impedance conductive path without occupying a significant surface area. It has been found that these traces can be spaced apart as closely as 1 micron. For reasons of manufacture, these traces are often spaced apart at least 5 microns.

It should further be appreciated that the titanium/gold/titanium laminates that form conductors should have a thickness of less than 5 microns. This limits the strain to which the conductors 348 are exposed when folded or bent to that which this laminate can withstand without breakage.

The titanium/gold/titanium laminates that form the electrode base pads 293 have a thickness of at least 5 microns and typically at least 10 microns. The relatively thick nature of these laminates is to make the base pads 293 radio opaque. It is desirable to have the base pads 293 radio opaque so the position of the assembly can be tracked using a fluoroscope. Thus, while not illustrated it should be appreciated that the thickness of the gold layers 364 that are part of the electrode base pads 293 are often thicker than the gold layers 364 that are part of the conductors 348. The portion of this laminate that defines the base pad 293 of an electrode 292, occupies a surface area of at least 1 $mm^2$. Typically this base pad occupies a maximum surface area of 10 $mm^2$ and typically 5 $mm^2$ or less. It has been found that electrodes with smaller sized base pads are difficult to detect with fluoroscopic instruments and with the eye that monitors the images produced by these instruments.

Figure 40:
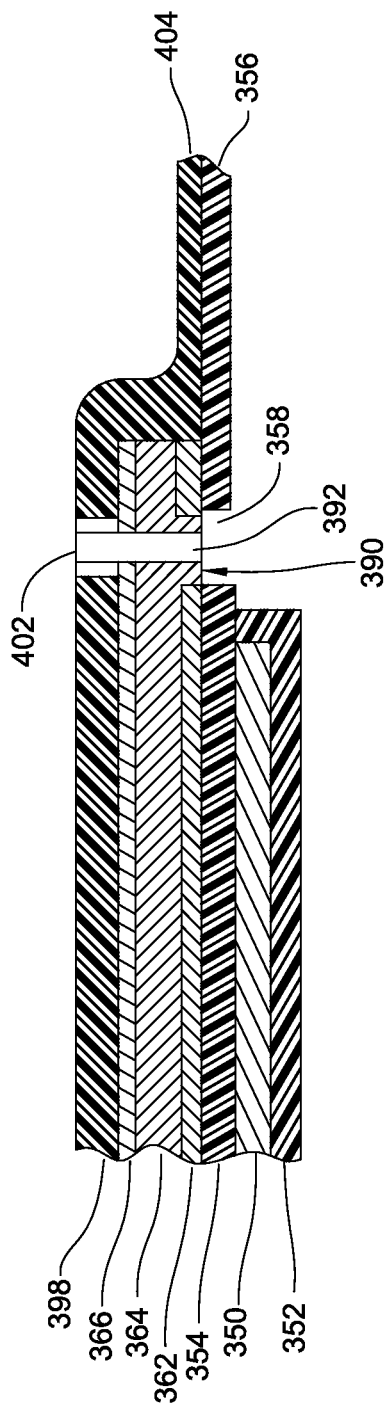
FIG. 40 is a cross sectional view of the terminal pad of the assembly with drive module removed to allow identification of the features of the terminal pad.

In FIGS. 36 and 40 it can be seen that each conductor 348 is further formed to extend a short distance over the adjacent terminal pad passive side insulating layer 356. Each conductor 348 terminates at a ring-shaped terminal 390 also formed over the terminal pad passive side insulating layer 356. Terminals 390 are formed during the same process steps in which conductors 348 and electrode bond pads 293 are formed. Specifically, in this part of the process, each titanium layer 362 is formed to define a circle (not identified) having a diameter equal to that diameter of the associated terminal 390. This circle, seen in cross section in FIG. 40, is centered over the opening 358 in the underlying passive side insulating layer. This titanium circle has a diameter greater than that of the underlying opening 358. A center opening is formed in this titanium circle (opening not identified). Gold, that is contiguous with the gold of layer 364, fills the opening in the terminal-forming portion of the titanium layer 362. When the titanium is applied to define titanium layer 366, this titanium is not applied to the face of the gold that functions as the face of terminal 390.

An opening 392 exists in the portions of the gold layer 364 and titanium layer 362 that define each terminal 390. This opening 392 is concentric with opening 358 in terminal pad passive side layer 356. Opening 392 is smaller in diameter than the coaxial opening internal to the underlying titanium layer 362. Opening 392 has an approximate diameter of 45 microns. The gold that defines the outer perimeter of the terminal around opening 392 has an approximate diameter of 90 microns.

An electrode 292 of assembly 290 of this invention, in addition to having the titanium/gold/titanium base pad 293, has two additional layers deposited above the outermost titanium layer 366 of the base pad. As seen in FIG. 37, a second outer layer of titanium 394 is disposed over the outer surface of titanium layer 366. A layer of iridium 396 is disposed over the outer surface of the titanium layer 394. The exposed surface of the iridium functions as the tissue-contact face of the electrode 292.

An insulating layer, again possibly a polyxylene polymer coating, is disposed over at least a portion of each electrode 292 and over the whole of the conductors 348. The insulating layer applied over conductors 348 prevents the conductors from functioning as electrodes. This insulating layer is applied over both the electrodes 292 and conductors 348 as a laminate that adds structural strength to assembly 290. In the Figures, this insulating layer is identified as active side insulating layer 398. An opening 402 is formed in layer 398 that is concentric with terminal opening 392. Opening 402 is larger in diameter than terminal opening 392.

Figure 41:
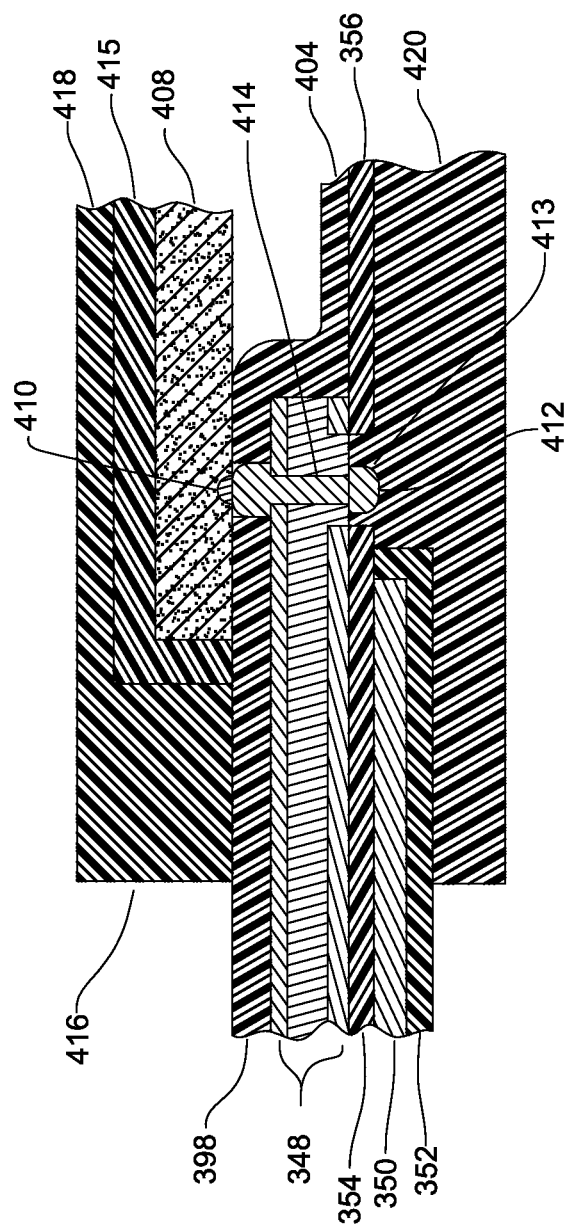
FIG. 41 is a cross sectional view of the terminal pad showing how the drive module is fitted to the pad.

The coating forming the active side insulating layer 398 is also disposed over the adjacent surface of the terminal pad passive/side layer 356. In this section of the assembly, this coating is called out as the terminal pad active side layer 404. This active side layer 404 is disposed over the titanium layers 366 of the terminals 390. In FIGS. 40 and 41 the terminal pad active side layer 404 is shown to curve downwardly from the active side insulating layer 398. This is because the material from which the active side insulating layer 398 and the terminal pad active side layer 404 are formed is a conformal coating. Over most of the terminal pad 296 neither conductors 348 nor terminals 390 are present. Accordingly, in these sections of terminal pad 296 free from conductive metal, terminal pad active side layer 404 dips below the adjacent active side insulating layer 398.

In some methods of manufacturing the electrode array assembly of this invention, the material forming the active side insulating layer 398 and the terminal pad active side layer 404 is applied to cover the whole of the electrodes 292, the conductors 348 and terminals 390. Portions of this insulating material are removed to expose small sections of each of the iridium layers 396 of the individual electrodes 292. These individual openings 399 may be circular or rectangular in shape. Thus, while the base pad 293 of an individual electrode may have a surface area of 2.25 mm$^2$ the exposed surfaces of the iridium layer 396, the surfaces through which current is sourced to or sunk from the adjacent tissue, may collectively have an area of 1.8 mm$^2$.

FIG. 41 illustrates how drive module 294 is attached to the other components of the electrode array assembly 290. Drive module 294 includes a semiconductor die 408 on which a circuit for connecting the individual electrodes 292 to current sources and current sinks is fabricated. As discussed below, in some versions of the invention, the current sources and current sinks may also be fabricated on die 408. Bond pads 410 (one illustrated) are formed on the bottom surface of die 408 directed towards the terminal pad active side layer 404. A portion of die 408 may also extend over the active side insulating layer 398.

Die 408 is positioned over the exposed face of terminal pad active side layer 404. More particularly, the die 408 is positioned over the assembly terminal pad 296 so that each bond pad 410 is in registration with its corresponding terminal opening 392. In FIG. 41, a small gap between the outer face of the terminal pad active side layer 404 and die 408 is exaggerated for purposes of illustration. A rivet 412 extends through the conductive ring 366 to the bond pad. This rivet 412, which is often formed from a small droplet of liquefied gold, has a head 413 that is formed around the face of the gold layer 364 of the terminal exposed through intermediate insulating layer opening 358. Rivet 412 has a shaft 414 that extends from the rivet head 413 to the associated die bond pad 410. Each rivet 412 thus connects the associated die bond pad 410 to the associated conductive ring 366.

Rivets 412 also hold the die 408 to the assembly terminal pad 296. In some versions of the invention, additional rivets that do not provide die-conductor electrical connections provide additional mechanical connections between the terminal pad 296 and the die 408. It should further be understood that since terminal pad 296 and feet 312 and 314 are planar, die 408 lies flat against the terminal pad. This flat surface-to-flat surface interface facilitates the bonding of the die 408 to the rest of the assembly 290.

An inner capsule 415 extends around the exposed faces of die 408. Inner capsule 415 is thus disposed over terminal pad active side layer 404. The inner capsule 415 is formed from material such as epoxy. In some versions of the invention, die 408 is encased in inner capsule 415 before the die is attached to terminal pad 296. The sides of inner capsule 415 extend to the surfaces of the terminal pad active side layer 404 that surround the die 408.

Drive module 294 also includes an outer capsule 416 formed from a mechanically robust, insulative, biocompatible material, such as epoxy or silicon oxide. Outer capsule 416 includes a shell and a cap 418 and 420, respectively. Outer capsule shell 418 covers inner capsule 415 and semiconductor die 408 encased therein. The side walls of outer capsule shell 418 abut active side insulating layer 398. More particularly, outer capsule shell 418 is dimensioned to abut the portion of active side insulating layer 398 that extends over the portion of frame 350 that define the proximal end of bridge 304 and feet 312 and 314.

Outer capsule cap 420 is disposed over the terminal pad passive side layer 356. Cap 420 also extends beyond the perimeter of passive side insulating layer 356. Cap 420 thus extends at least partially over the portions of outer capsule shell 418 that likewise extend beyond the perimeters of the terminal pad passive and active side layers 356 and 404, respectively. The adjacent abutting portions of shell 418 and cap 420 are sealed or otherwise bonded together to form the outer capsule 416.

In some versions of the invention, the proximal end of bridge 304 and assembly feet 312 and 314 are formed with through openings, not illustrated. These through openings extend through insulating layers 352, 354 and 404 and frame 350. The material forming either outer capsule shell 418 and/or cap 420 is molded in place. A portion of the material forming this molded structure extends through these openings in the bridge 304 and feet 312 and 314. Upon hardening, this material forms posts that extend through bridge 304 and feet 312 and 314 that further secure the outer capsule 416 to the rest of assembly 290.

The sub-circuits that may be formed on the die 408 integral with drive module 294 may be similar to the sub-circuits contained within circuits 45 of electrode array assembly 40. Electrode array assembly 290 as illustrated does not include an antenna. Power that forms the current sourced and sunk between the electrodes 292 as well as power to energize the components internal to the drive module comes from an implantable device controller (IDC) 428 (FIG. 35). The IDC 428 is connected to and separate from the electrode array assembly 290. This connection is made by a cable 427. In versions of the invention wherein this cable 427 is present, wires internal to the cable are connected to bond pads integral with die 408. These bond pads are separate from and spaced away from the bond pads 410 to which rivets 412 are bonded. In some versions of the invention, bond wires, not shown are connected from the die bond pads to terminal pads on the adjacent surface of inner capsule 415. The wires integral with cable 427 are also connected to the bond pads on the inner capsule 415. The adjacent end of the cable 427 is held to assembly 290 by potting between outer capsule shell and cap 418 and 420, respectively.

Figure 42:
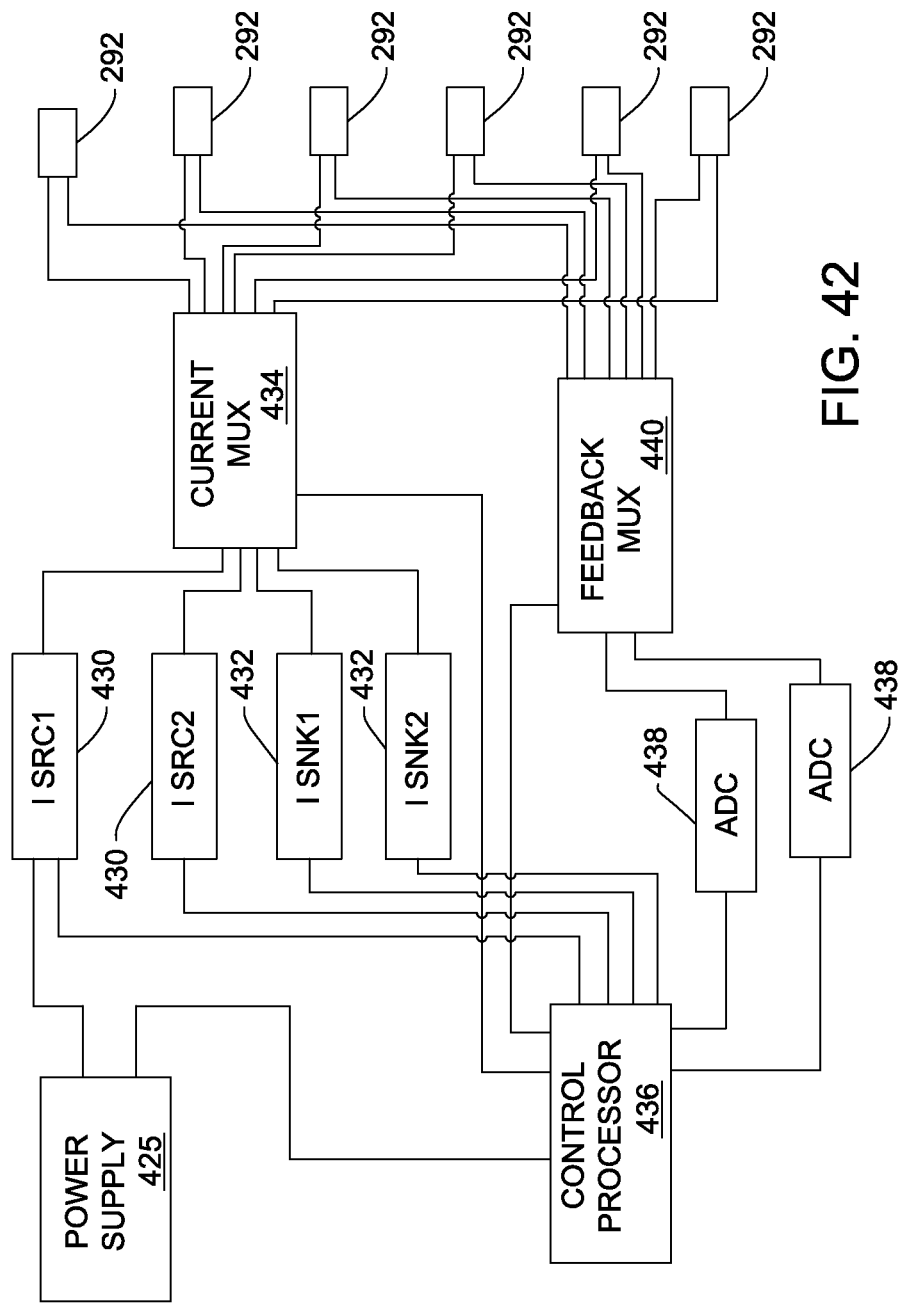
FIG. 42 is a block diagram of a number of the sub circuits that may be internal to the drive module.

As seen with respect to FIG. 42, in some versions of the, drive module 294 includes a power supply 425. The power supply module may include a power harvesting circuit (not illustrated). The power harvesting circuit stores the power contained in the instruction signals forwards to the electrode array assembly 290 by the IDC 428. This power is stored in a capacitor or a rechargeable cell, part of the power supply 425 and not illustrated. A constant voltage circuit, also part of the power supply 425, outputs one or more constant voltage signals to the other components of drive module 294.

Drive module 294 also includes a number of variable-output current sources 430 and variable output current sinks 432. (For ease of illustration, power supply 425 is shown connected to only a single current source 430. It is understood that the power supply 425 is connected to each source 430 and sink 432.) In FIG. 42, only two current sources 430 and two current sinks 432 are illustrated. In practice, power supply module 294 may have three or more current sources 430 and current sinks 432. In some versions of the invention, the number of current sources 430 and current sinks 432 may each equal the number of electrodes 292.

In versions of the invention wherein the number of current sources 430 and current sinks 432 is each less than the total number of electrodes, the sources and sinks are connected to the array electrodes 292 through a current multiplexer 434, also fabricated as part of die 408. Current multiplexer 434 connects the current sources and sinks 430 and 432, respectively, to the electrodes 292. For ease of illustration in FIG. 42 only six (6) electrodes 292, the number of electrodes in a single row of the assembly 290 of FIG. 35, are illustrated.

Drive module 294 also includes a control processor 436. Processor 436 regulates the magnitude of the current sourced and sunk by, respectively, each source 430 and sink 432. The processor 436 also asserts control signals to current multiplexer 434. Based on the signals asserted by processor 436, multiplexer 434 connects each source 430 and sink 432 to the appropriate electrode/electrodes 292.

It should be understood that, at any given moment, multiplexer 434 is able to connect each electrode to a current source 430 or to a current sink 432. Nevertheless, it should be appreciated that the switches forming multiplexer 434 each have at least one failsafe sub switch (not illustrated). Each multiplexer sub switch prevents a single electrode 292 from simultaneously being tied to both a current source 430 and a current sink 432. This arrangement substantially eliminates the possibility that a short circuit can develop between a source 430 and a sink 432.

In FIG. 42, power supply 425 is shown connected to control processor 436. This represents that power supply 425 sources the current that energizes the components internal to module 294.

Control processor 436 controls the magnitude of the current sourced and sunk by sources 430 and sinks 432 and to which the electrodes the sources and sinks are attached based in part, on the instructions loaded in the processor. While not shown as a separate component, internal to the processor 436 is a memory. This memory stores the operating instructions for the processor 436. This memory also stores the instructions that are executed by the processor 436 regarding which electrodes 292 are to be tied to a current source 430 or sink 432 and the magnitude of the current that is to be sourced or sunk by the current source 430 or sink 432. These instructions may be received from the modulator/demodulator circuit or from the conductors that connect assembly 290 to the IDC 428.

The control processor 436 also asserts output signals based on the measured voltages across the electrodes 292. To facilitate this feedback control, module 294 also includes one or more analog to digital voltage converters (ADCs) 438, (two shown). The ADCs 438 are connected to the electrodes 292 over a feedback matrix 162, also part of drive module 294. In the illustrated version of the invention, feedback multiplexer 440 is able to simultaneously connect any of the two electrodes 292 to a separate one of the two ADCs 438.

Once electrode array assembly 290 is assembled, the assembly 290 is folded. Specifically, the assembly 290 is bent around two fold lines 446 and 448 that are parallel to and laterally spaced from the longitudinal axis of the assembly. In FIG. 35, the distal ends of fold lines 446 and 448 are depicted as dashed lines. One of the fold lines, line 446, is the line along which the tabs 318 associated with bridge 302 are spaced from the adjacent tabs 318 associated with bridge 304. Fold line 448 is the line along which the tabs 318 that extend from bridge 304 are separated from the adjacent tabs 318 that extend from bridge 306. Each fold line 446 and 448 is likewise the line along which one of side edges of assembly head 326 is separated from the adjacent shoulder 340.

Figure 43:
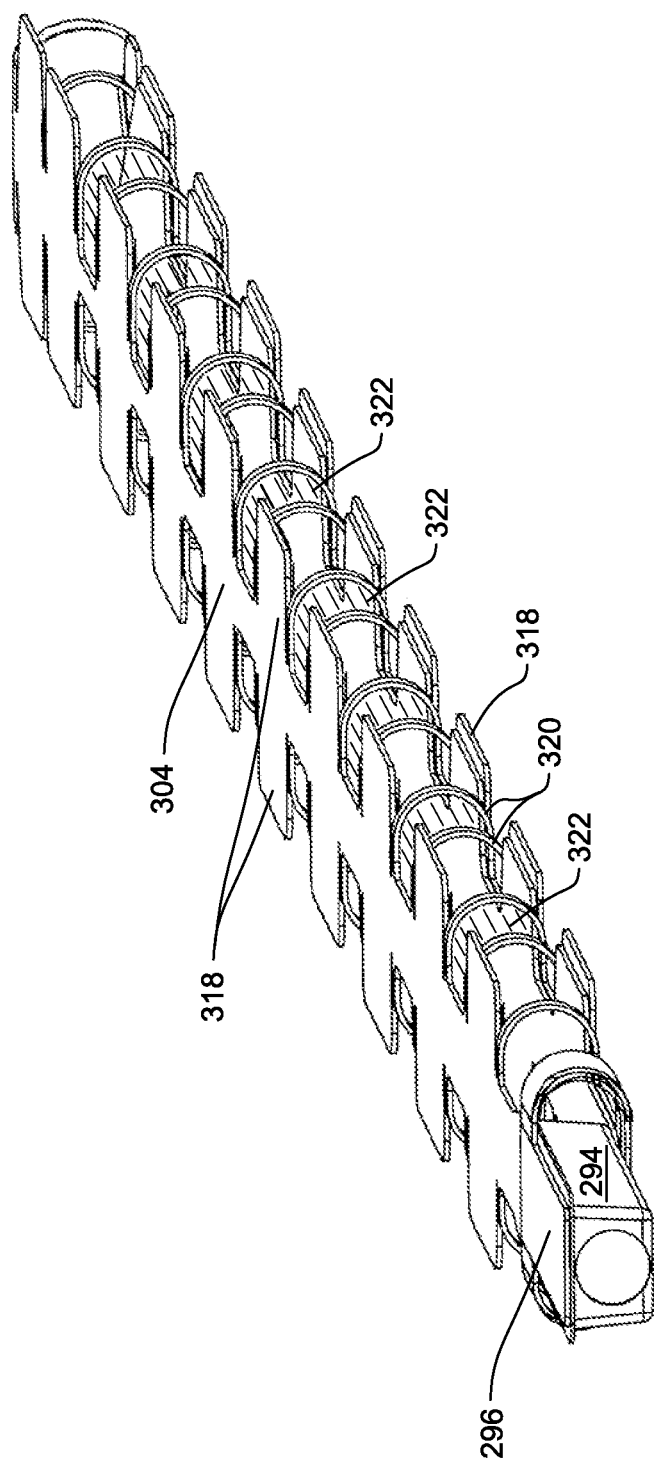
FIG. 43 is a perspective view of the electrode array of FIG. 35 in the folded state.
Figure 44:
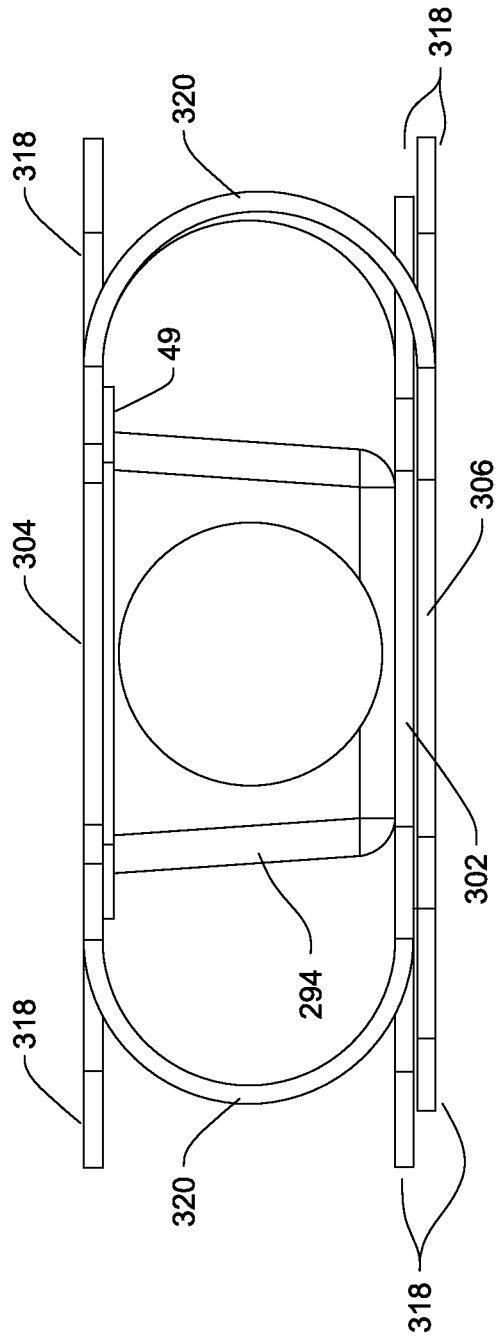
FIG. 44 is view located forward from the proximal end of the electrode array assembly when the assembly is in the folded state.

As a consequence of the folding process, bridges 302 and 306 are each folded inwardly towards center located bridge 304 as seen in FIGS. 43 and 44. During the folding process, the legs 308 and 310 and the beams 320 that extend between the bridges 302, 304 and 306 are subjected to folding. Also folded are the membranes 322 between the bridges 302, 304 and 306. The bridges 302, 304, 306, the tabs 318 and the electrodes 292 carried on the tabs are not subjected to folding.

Typically one bridge, in FIG. 44 arbitrarily bridge 302, is initially folded inwardly towards bridge 304 304. More particularly, bridge 302 is folded inwardly to rest on the surface of drive module 294 spaced from bridge 304. The second outlying bridge, bridge 306, is then folded inwardly so that bridge 306 overlies first bridge 304, the drive module 294 and then bridge 302.

Figure 45:
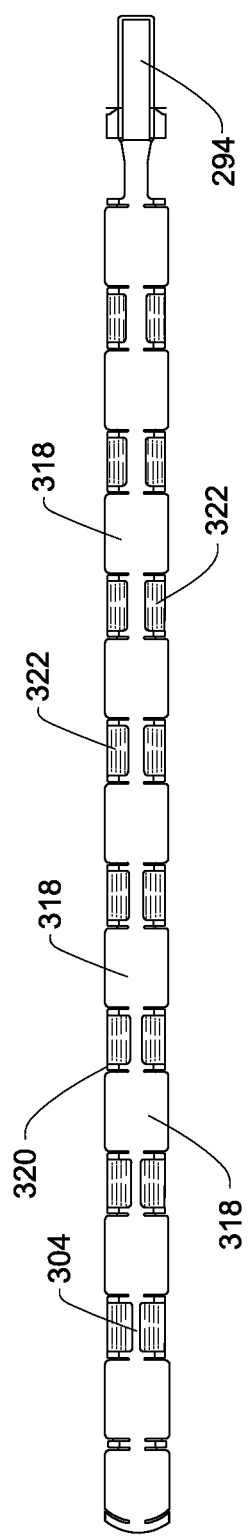
FIG. 45 is a top plan view of the electrode array when in the folded state.

Once the assembly 290 is so folded, the tabs 318 that extend from bridges 302 and 306 are both substantially in registration with the tabs 318 that extend from bridge 304. This is seen best in FIG. 45 wherein only the top most of the bridges, bridge 304 is seen when assembly 290 is in the folded state.

It should be appreciated that, during this folding process, neither drive module 294 nor terminal pad 296 is subjected to appreciable folding.

Once electrode array assembly 290 is so folded, the assembly 290 is fitted in the lumen of the deployment (inner) cannula 240 (FIG. 26). Since the assembly is folded, the assembly can be fitted into a deployment cannula with a lumen 242 that has a major diameter less than the unfolded width of the assembly. The deployment cannula with the folded assembly 290 therein, is fitted in an access cannula 250 (FIG. 27). Access cannula 250, like deployment cannula 240, has a lumen 251 with a major axis that is smaller in width than the unfolded width of electrode array assembly 290. In versions of the invention that include a cable 427 attached to module 294, the cable 427 is understood to extend through cannulae 240 and 250. through delivery cannula.

Figure 46:
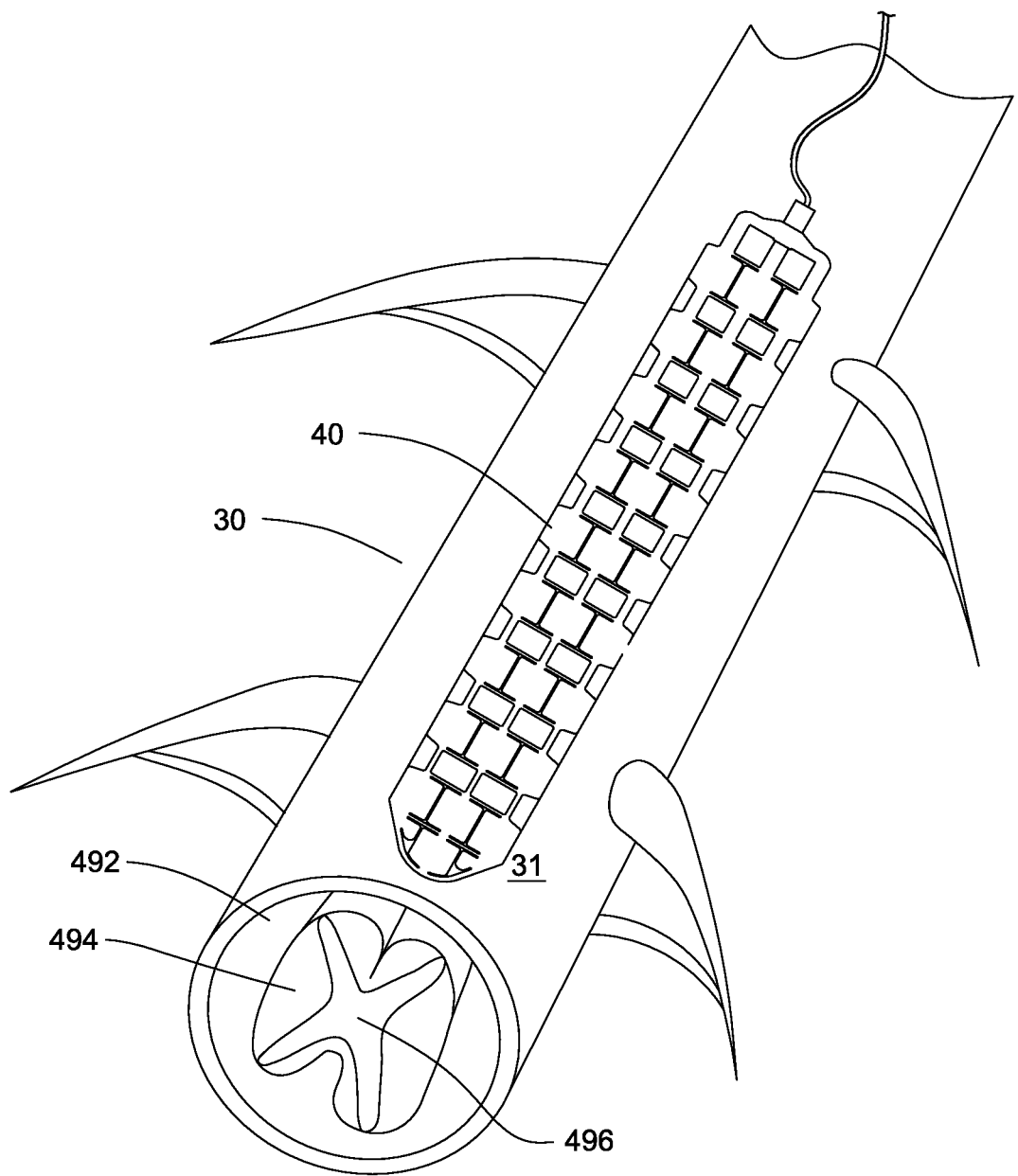
FIG. 46 is a perspective view of the electrode array of FIG. 35 deployed over a section of spinal cord dura.

Then, using the above described deployment method, the electrode array assembly and deployment cannula 240 are positioned over the target tissue. The deployment cannula 240 and folded electrode array assembly are advanced from the insertion cannula over the tissue. Once the folded assembly 290 is properly positioned, the deployment cannula is then retracted back into the access cannula while the electrode array assembly is blocked from similar movement. As the deployment cannula retracts away from the electrode array assembly, the super elastic properties of the assembly frame 350 cause the assembly to unfold. More particularly, the potential energy stored in the folded over beams 320 is released. The release of this energy is what unfolds bridges 302 and 306 away from bridge 304. Electrode array assembly 290 thus unfolds towards the tissue through which the therapeutic current is to be applied. Owing to frame 350 having a curvature that at least generally corresponds to the curvature of the underlying tissue, when the assembly is unfolded, the individual electrodes 292 are in close proximity to the underlying tissue. FIG. 46 illustrates electrode array assembly 290 would appear when deployed over a portion of the dura 31 of a spinal cord 30.

As long as bridges 302, 304, and 306 of array 290 are in registration with each other, the array is flexible, it can bend along its longitudinal axis. In other words, assembly 290 when in the folded state of FIG. 45, can bend both in and out of the page or to the right or left. The deployment assembly used to position array 290 may include a steering assembly, not illustrated and not part of the present invention, to direct the folded array 290 in position over the target tissue. This particular deployment assembly may include features other than the disclosed access and deployment cannulae 240 and 250, respectively.

During this deployment process, the rounded shape of the distal ends of shoulders 344 minimizes the likelihood that these shoulders will catch on the adjacent tissue. Also during the deployment process, membranes 324 reduce the incidence of tissue adjacent the sides of the assembly from being scraped by the outermost tabs 318 of the assembly 290. This reduces the potential of the tissue becoming damaged by these tabs 318.

After the electrode array assembly 290 is deployed, unfolded, the practitioner can make minor adjustments to the position of the array. The rounded shape of the array head 326 reduces the resistance of the array 290 to this movement.

In some versions of the invention, at the time electrode array assembly 290 is implanted into the patient, the IDC 428 is also implanted in the patient. Typically the IDC 428 occupies a space of 20 cc and is located below the skin in a pocket of subcutaneous fat. The IDC 428 includes an antenna for receiving power and instructions from a programmer external to the patient. Cable 427 over which signals are exchanged with the electrode array assembly 290 is connected to the implantable device controller 428.

Once the assembly 290 is in the unfolded, deployed, state, membranes 322 minimize the likelihood of tissue growth between beams 320. Membranes 324 similarly minimize tissue growth between the outermost tabs 318. Similarly, the insulating material extends outwardly from the inner tabs, the tabs integral with bridge 304 and the inner directed tabs associated with bridges 302 and 306. This insulating material reduces the open space around these tabs so as to likewise reduce the tissue growth adjacent these tabs. The minimization of the tissue growth between these features of the assembly 290 when deployed reduces the extent to which the tissue growth could inhibit the removal of the assembly 290 if such action is needed.

V. Activation of Assembly

Electrode array assemblies 28 and 290 of this invention are designed so that current can be simultaneously sourced and sunk between different combinations of electrodes 36 and 292, respectively. FIGS. 47B through 47E are representations of the magnitudes of the currents sourced and sunk through a set of eight linearly spaced apart electrodes 292a through 292h in different modes of operating the array 290. FIG. 47A is a reference key for FIGS. 47B through 47E that indicates which one of the electrodes 292a through 292h is, at a given instant serving as a current source or a current sink. In FIGS. 47B through 47E, the "+" symbol indicates the electrode is serving as a current source; the "−" symbol indicates the electrode is serving as a current sink. The scalar numbers in FIGS. 47B through 47E indicate the relative magnitude of the sourced or sunk current.

In practice, each active electrode will instantaneously source or sink current in the range of 0.1 to 20 mA in magnitude. Since electrodes 36 and 292 of this invention have base pads with a surface area of at least 1 mm$^2$, the current density at the surface electrodes is below the levels at which the materials forming the electrodes could breakdown. Provided proper pulse-by-pulse charge balancing, the current density is also below the levels at which the current flow through the tissue could cause damage to the tissue.

FIGS. 48 through 51 represent the density of the currents through the tissue of the spinal cord 30 as a consequence of the current being sourced and sunk according to the patterns of FIGS. 47B through 47E, respectively. More particularly, these Figures represent the current density during the leading phase of a current pulse. In FIGS. 48 through 51, the spinal cord is depicted as number of planar layers. In FIGS. 48-51, electrodes 292a through 292h are drawn as if they represent a single column consisting of electrodes 292. This is one electrode less than the number of electrodes in each column of electrodes that extend from bridges 302,304 and 306.

In FIGS. 48-51, eight electrodes 292 in a column of electrode array assembly 290 are shown on the spinal cord dura 31. Dura 31 is represented as a solid thick line. Below the dura the spinal cord 30 has a region 492. Region 492 contains the cerebral spinal fluid (CSF). Below the CSF, the spinal cord 30 includes a region 494 with white matter. Below the white matter 494, in the center of the spinal cord, is the gray matter 496. Both the white matter 494 and gray matter 496 are formed from the actual nerves of the spinal cord. In one application of assembly 290, the current is flowed through specific regions of white matter 494. The current is flowed through the white matter to cause the nerves forming the white matter to react in such a way that the white matter nerves affect the function of the nerves forming the gray matter 496.

In FIGS. 48-51, the lines represent lines of constant current density (Amps/meter$^2$). For ease of illustration, in each of FIGS. 48-51 the current density of only a few of these lines is identified with specificity. The actual direction of current flow is independent of the these lines of constant current density. The CSF in region 492 has a relatively low impedance. In comparison, the white matter of region 494 is of relatively high impedance. Accordingly, given both the proximity of the CSF region 492 to the electrodes 292 and the relatively low impedance of the CSF, current density is greatest in this region. This means that the majority of the current flow is through CSF region 492. Nevertheless, if the current flow is of sufficient amplitude, there will be sufficient current flow through the white matter region 494 to cause the desired reaction of the nerves forming this region.

The lines of constant current density of FIGS. 48-51 indicate that there is some current flow above the electrode array assembly 290 and by extension above the spinal cord 30. This section of the body typically contains fat, a high impedance tissue. Accordingly, while there is some current flow through this tissue, the amount of this current is relatively small. Given both the magnitude of this current and the nature of the tissue, this current flow through the tissue typically has no appreciable effect on the patient.

Figure 48:
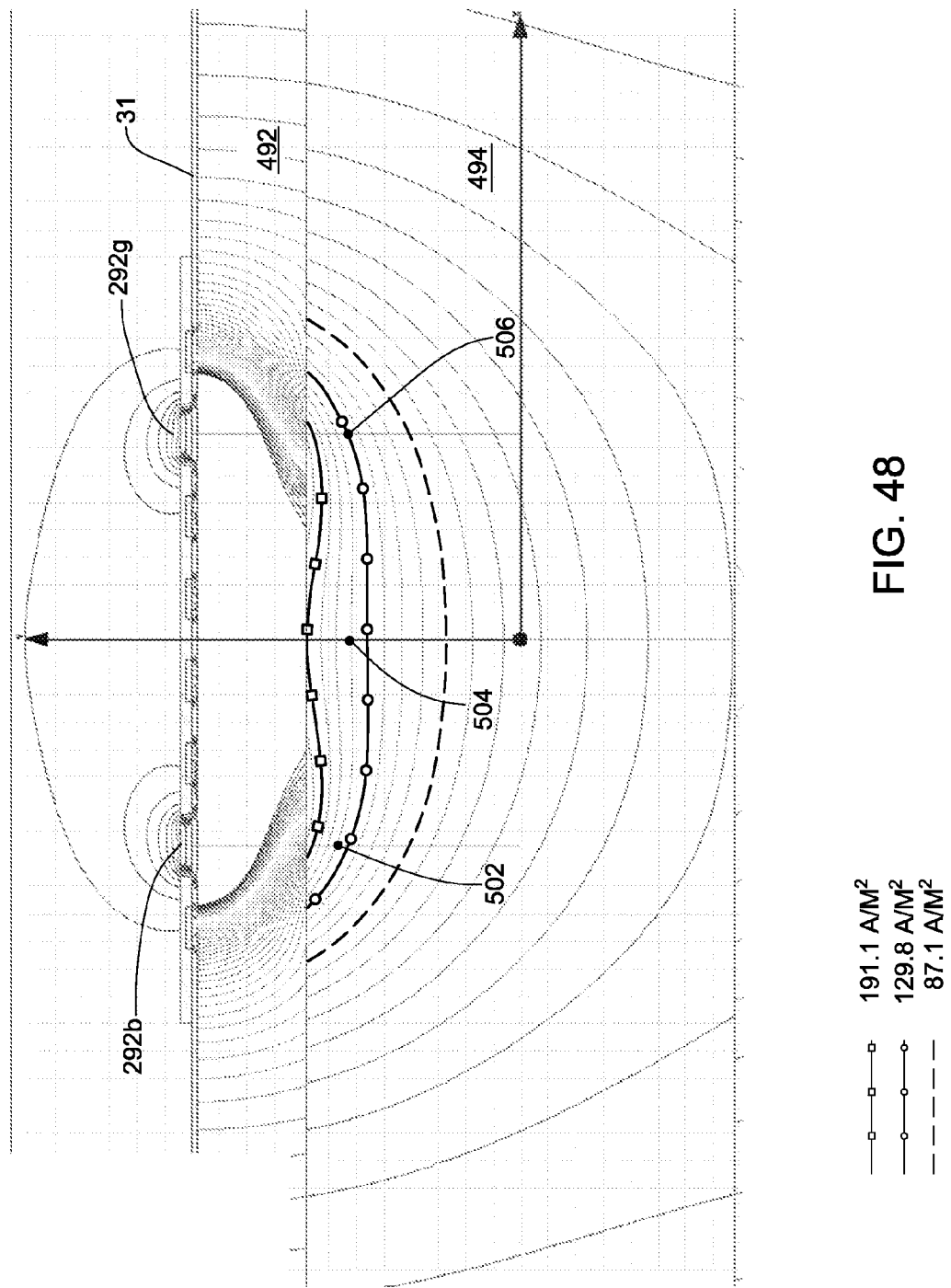
FIG. 48 represents the current density in the tissue when the electrodes are actuated according to the pattern of FIG. 47B.

FIG. 48 illustrates the intensity of the current that develops as a consequence of current being flowed between only a single pair of electrodes, the arrangement of FIG. 47B. Thus, it should be appreciated that to achieve the below-described current flow patterns, electrode 292b is tied to one of the current sources 430, electrode 292g is tied to one of the current sinks 432. Control processor 436 sets the active source 430 and active sink 432 to, respectively, source and sink the same magnitude of current. The current therefore flows from below electrode 292b to below electrode 292g.

Consequently, as a result of this current source/sink arrangement, it can be seen that along a line of constant depth from the surface of the white matter region, between the driven electrodes, the current flow is of a constant density. Specifically the current flows through point 502, below electrode 292b, point 504, between electrodes 292b and 292g and below point 506, are relatively close to each other. Points 502, 504 and 506 are understood to be a constant depth below the outer surface of the white matter region. Such a current flow may be desirable if the therapy requires that the current influence a relative large section of tissue.

FIG. 47C represents how current is sourced and sunk between the electrodes to minimize current flow in the white matter region between the electrodes. Here, one electrode, electrode 292b serves as the primary source electrode and electrode 292g functions as the primary sink electrode. Thus, electrode 292b is, through multiplexer 434, connected to one of the current sources 430. Electrode 292g, also through multiplexer 434, is connected to one of the current sinks 432. The electrodes on either side of primary source electrode 292b, electrodes 292a and 292c, are, through the multiplexer 434, tied to a second one of the current sinks 432. These electrodes function as secondary current sinks. Simultaneously, the electrodes on the opposed sides of electrode 292g, electrodes 292f and 292h, are tied to a second one of the current sources 430.

When current is driven during this process, control processor 436 sets the current source to which electrodes 292h and 292g are connected to source one-half the current that is supplied by the source 430 to which electrode 292b is connected. The current sink 432 to which electrodes 292a and 292c are connected are set to sink one-half the current that is to be sunk by the sink 432 to which electrode 292g is connected. When current is sourced/sunk in this mode of operation a first primary current flow path is from electrode 292b to electrodes 292a and 292c. A second primary current flow path is from electrodes 292f and 292h to electrode 292g. There is also some current flow at least in the CSF region in the space below and between electrode 292c and electrode 292f.

Figure 49:
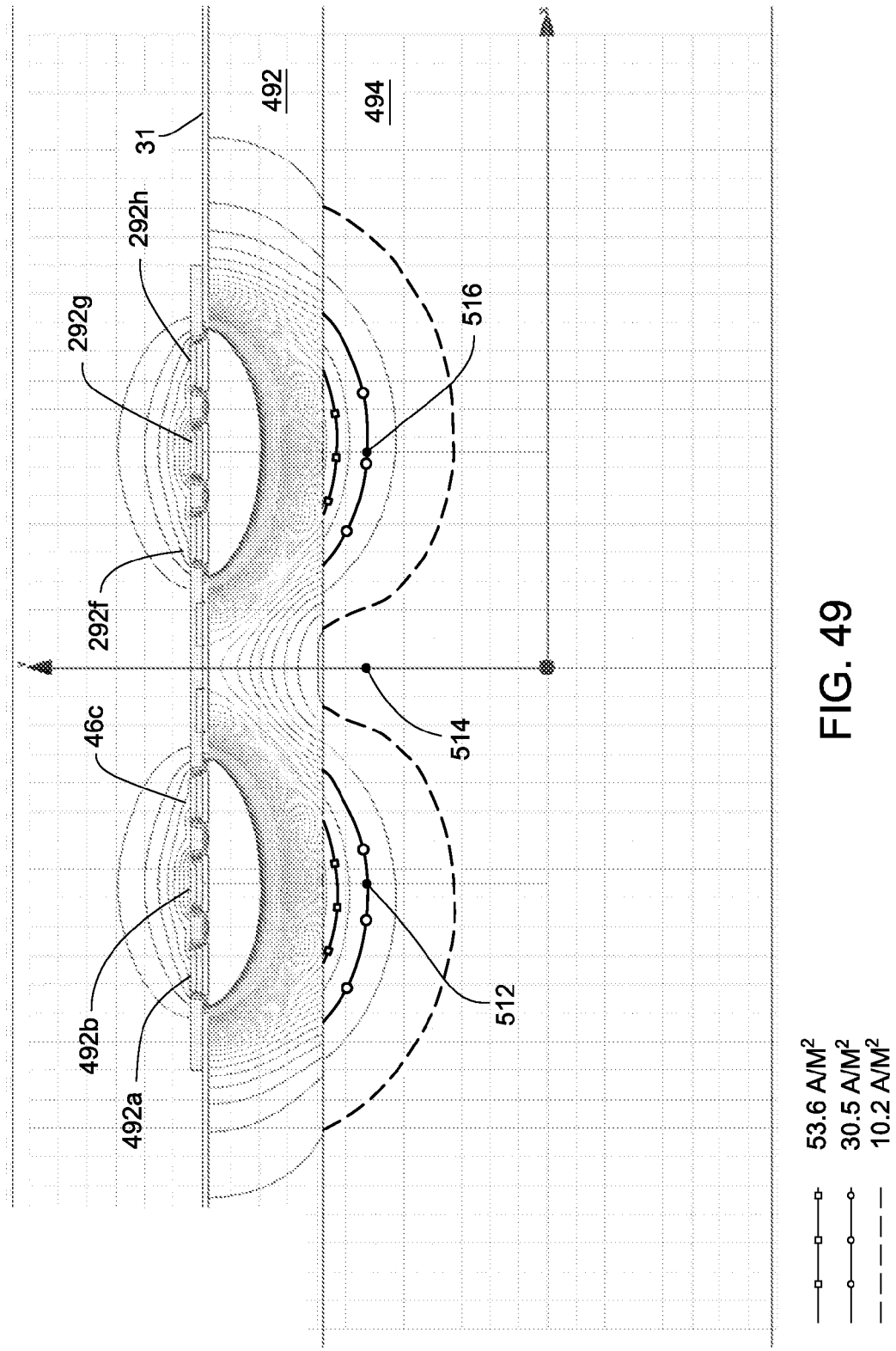
FIG. 49 represents the current density of the tissue when the electrodes are actuated according to the pattern of FIG. 47C.

FIG. 49 illustrates the densities of the current flows that develop as a consequence of the current being sourced and sunk according to the pattern of FIG. 47C. Here it can be seen that within the white matter, the regions below electrodes 292b and 292g, points 512 and 516, identical to points 502 and 506, respectively, there is less current flow than when the current flow was in the above-described pattern associated with FIG. 47B. Further, at point 514, identical in location to point 504 representative of the region between the electrodes, there is essentially no current flow.

FIG. 47D represents the source/sink configuration of the electrodes of assembly 290 of this invention when it is desirable to flow current through two regions of the spinal white matter while minimizing current flow between these regions. Here electrodes 292c and 292e are set to serve as, respectively, the primary source and sink electrodes. Thus, electrode 292c is connected to the current source 430 set to source the largest magnitude current while, simultaneously electrode 292e is connected to the current sink 432 set to sink the largest magnitude current. Electrodes 292a and 292b, the electrodes located to one side of electrode 292c, are connected to a second current source 430. This second current source is set so electrodes 292a and 292b each source one-half the current sourced by electrode 292c. Thus, in this configuration of array 290, electrodes 292a and 292b function as the secondary current source electrodes. In this configuration of the invention, electrodes 292g and 292h are simultaneously tied to a second current sink 432. Processor 436 sets this second sink 432 so it sinks from each electrode 292g and 292h one-half the current that is sunk by electrode 292f.

Figure 50:
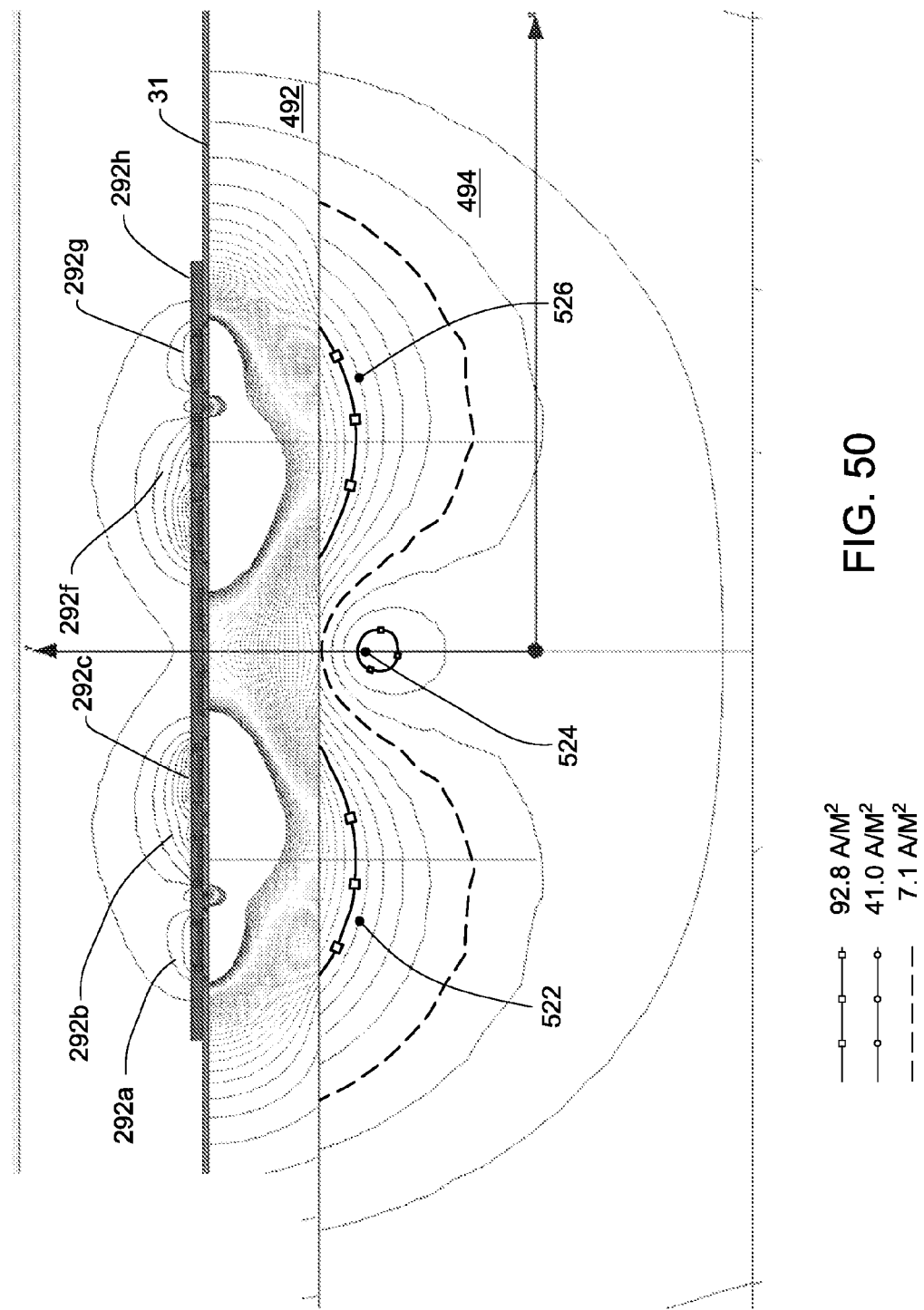
FIG. 50 represents the current density of the tissue when the electrodes are actuated according to the pattern of FIG. 47D.

When assembly 290 is operated in this configuration current flow through the white matter region is primarily through two spaced apart regions. One region is the region through which the current flows from electrodes 292c to electrodes 292a and 292b. The second region is the region through which the current flows from electrodes 292g and 292h to electrode 292f. Points 522 and 526 on FIG. 50 are, respectively, representative of these first and second regions. Points 522 and 526 are analogues to points 512 and 516 of FIG. 49. It can be seen that the current flow through points 522 and 526 is greater than the current flow through points 512 and 516.

The above discussed current through the primary regions of the white matter causes small currents to flow in opposed directions on opposed sides of point 522. Given the magnitude and opposed directions of this current flow, the current flow through point 524, analogues to point 514, can be considered zero.

FIG. 47E represents how the electrode array assembly 290 of this invention can be configured to induce appreciable current flow in the tissue adjacent one of the primary source sink electrodes but not the complementary electrodes. In this configuration of the invention, two electrodes, electrodes 292a and 292b simultaneously function as the primary source electrodes. Thus both electrodes are connected to a current source that sources the same current to both electrodes. Also in this configuration of the invention, a single electrode, electrode 292g, functions as the sink electrode. Processor 436 therefore connects this electrode to one of the current sinks 432. Further in this configuration of the invention the electrodes on either side of electrode 292g, electrodes 292f and 292h, function as secondary source electrodes. Electrodes 292f and 292h are thus connected to a different source than the source to which electrodes 292a and 292b are connected. The source to which electrodes 292f and 292h are connected causes each of these electrodes to source one-half of current sourced by each of electrodes 292a and 292b.

From each of FIGS. 47B through 47E it should further be understood that in preferred versions of this invention the current sunk by the sink electrodes is identical to the current sourced by the source electrodes. This is to prevent stray currents flowing through tissue.

Figure 51:
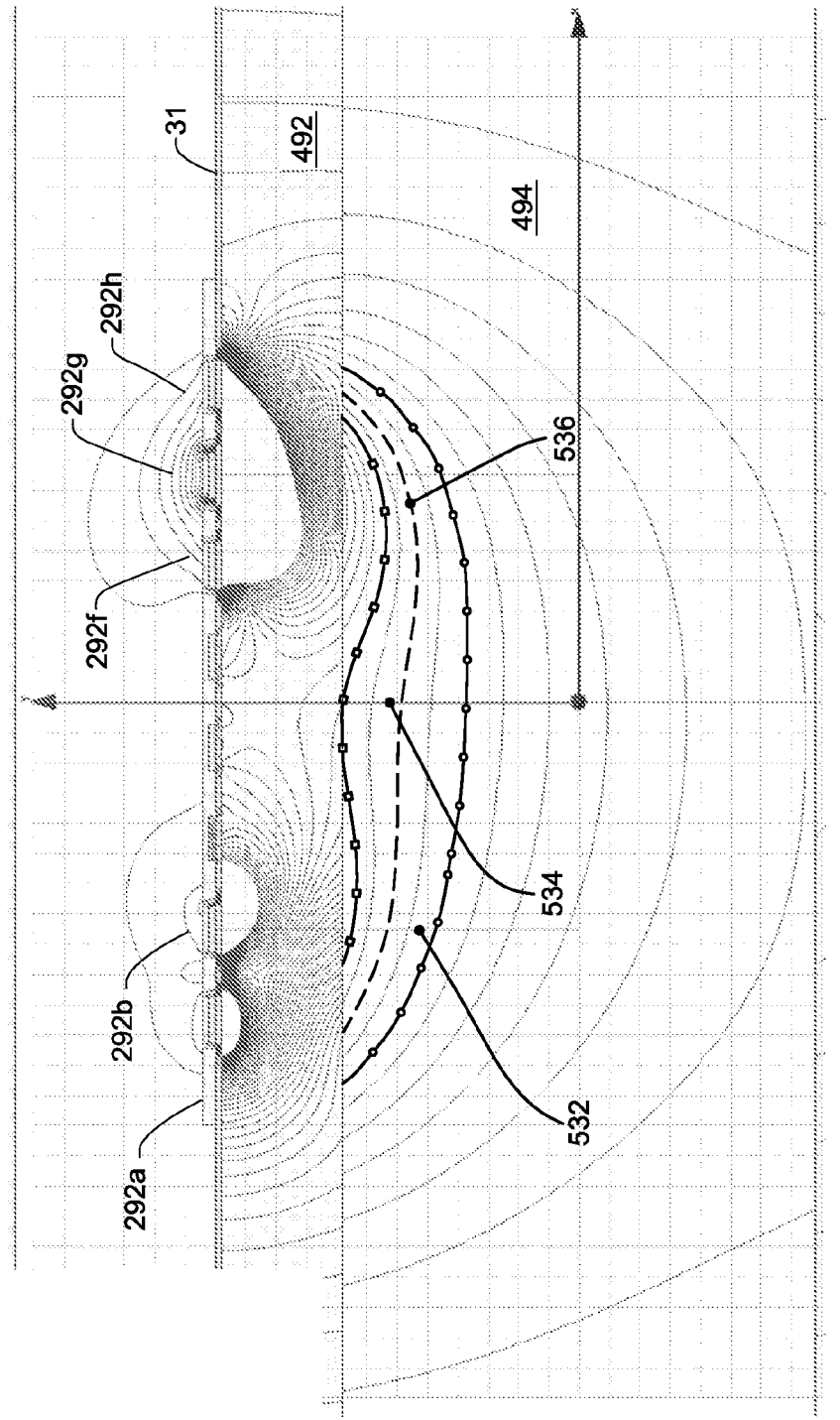
FIG. 51 represents the current density of the tissue when the electrodes are actuated according to the pattern of FIG. 47E.

As a consequence of the assembly 290 being operated as described in FIG. 47E, the current can be considered sourced over a wide area but sunk over a narrower area. FIG. 51 depicts the density of these current flows. Here it can be seen that in the white matter region in the vicinity below electrode and 292b, around point 532 analogous to point 502, there is some current flow. There is also current flow in the white matter region between electrodes 292d and 292e, point 534, analogues to point 502. The current flow through points 532 and 534 is substantially equal. From FIG. 17 it can further be seen that when current is flowed in accordance with the pattern of FIG. 47E, the current density is more intense in the white matter region between electrodes 292f and 292g, point 536, analogous to point 506. In other words, the current flow through point 536 is appreciably greater than the current flow through both points 532 and 534.

Thus, it should be appreciated that a feature of this invention is that by selectively causing more than three of the electrodes of assembly 290 to simultaneously serve as source or sink electrodes that both the region in the spinal through which the current flowed can be targeted and the intensity of the current flow adjusted. This targeting and focusing/diffusing of current flow is what results in the current causing the desired reaction of the nerves forming the white matter region 494. Still another feature of this invention is that by establishing the source and sink electrodes so that they are asymmetric relative to each other, assembly of this invention can be configured so that only a specific defined region of spinal white matter is subjected to appreciable current flow. It should likewise be appreciated that the operating mode of the which electrodes function as sources or sinks can be reset throughout the time the array is disposed against the tissue. This allows the location of where in the tissue the current is flowing and the focusing/diffusing of the current to be changed if modification is warranted by changes in the condition of the patient.

Further, upon initial implanting of the assembly 290 one can drive current flow through a number of different regions of the underlying tissue. This allows the practitioner and patient to determine through which region of tissue the current flow offers the most satisfactory benefits and/or tolerable side effects. Once this region is identified, the IDC 428 can be set to cause the array to drive current through this region of tissue.

Figure 52:
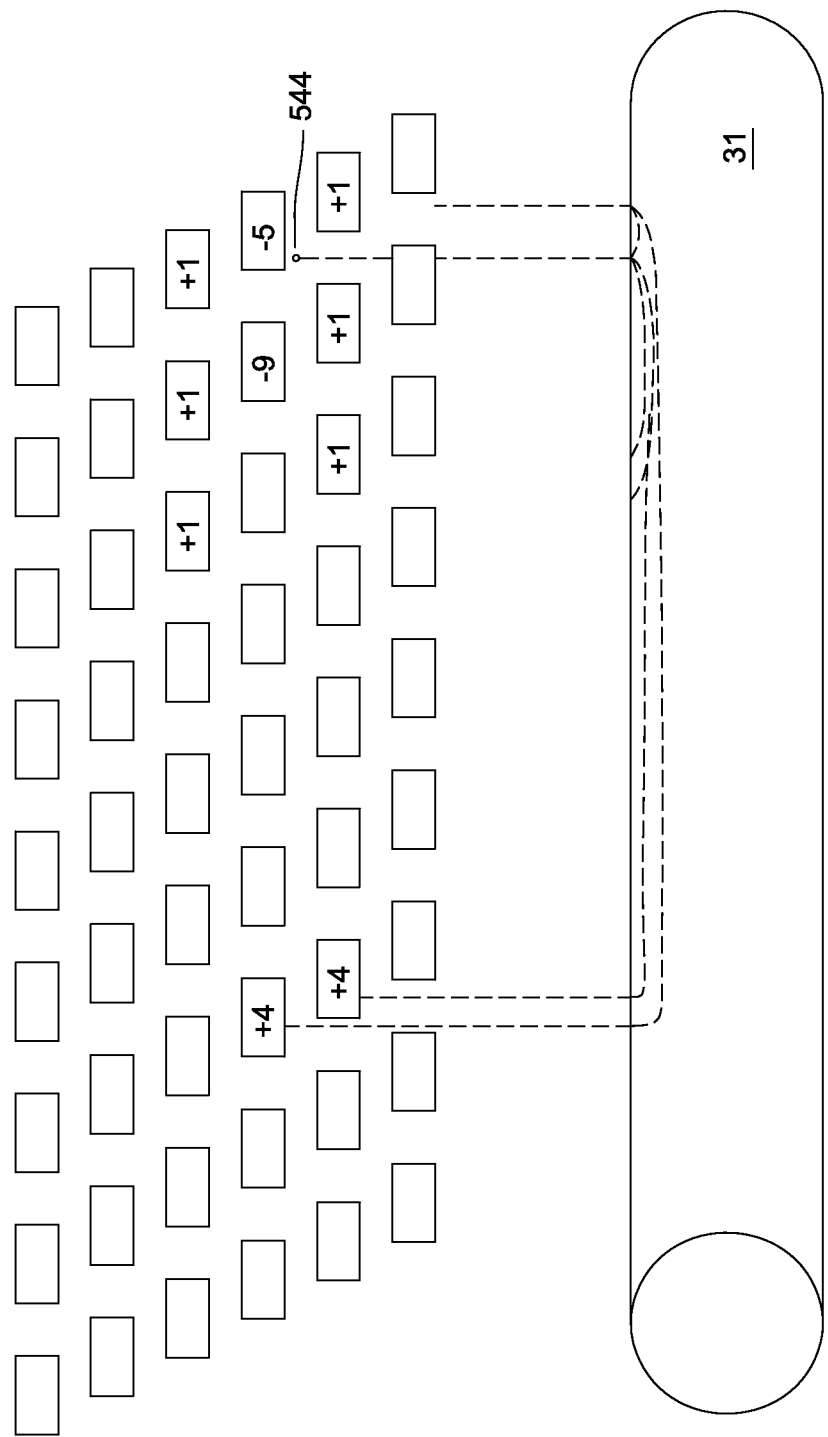
FIG. 52 is a diagrammatic illustration of how, by sourcing and sinking current between different electrodes of the two dimensional version of the assembly of this invention, current can be focused through tissue that is off line from a particular column of electrodes.

Given that the electrode array assembly of this invention includes both plural rows and plural columns of electrodes 292, it should be understood that this invention also makes it possible to focus the current flow through tissue that is laterally offset from the source or sinking electrodes. This is illustrated in FIG. 52. Here, the individual electrodes 292 of the assembly of FIG. 35 are illustrated as rectangular blocks. To be consistent with FIG. 1, each horizontal line of electrodes 292 is analogous with one of the columns of electrodes of FIG. 35. Each diagonal line of electrodes 292, extending from the top most column is analogous to a row of electrodes of FIG. 1. Current is sourced from or sunk to the blocks (electrodes) containing whole numbers. The numbers indicate the relative strengths of the currents sourced or sunk be each electrode 292. As before the "+" symbol indicates that the electrode functions as a source; the "−" symbol indicates that the electrode functions as a sink.

In the illustrated configuration, two electrodes 292 in the third row from the left side of FIG. 52 function as the primary source electrodes. The electrode in the fourth column, (from the top) and eighth row from left is the primary sink electrode. The electrode in the fourth column, ninth row is connected to a current sink to serve as a secondary sink electrode. The seventh through ninth electrodes in the third and fifth columns serve as field focusing electrodes. These electrodes are located on the opposed sides of the primary and secondary sink electrodes. These field focusing electrodes source current, as opposed to the sinking of current by the primary and secondary sink electrodes.

As a consequence of current being sourced and sunk through the array according to the pattern of FIG. 52, the region in spinal cord white matter section in which current flow is focused is located slightly below and slightly to the right of the electrode that functions as the primary sink electrode, represented by point 544 in FIG. 52. In this Figure, the dashed lines represent current flow through the tissue. This illustrates that since the current can be sourced or sunk over a two dimensional area (discounting for curvature of the tissue) the regions in which the current flow is focused can be both longitudinally and laterally offset relative a given primary source or sink electrode.

Figure 53:
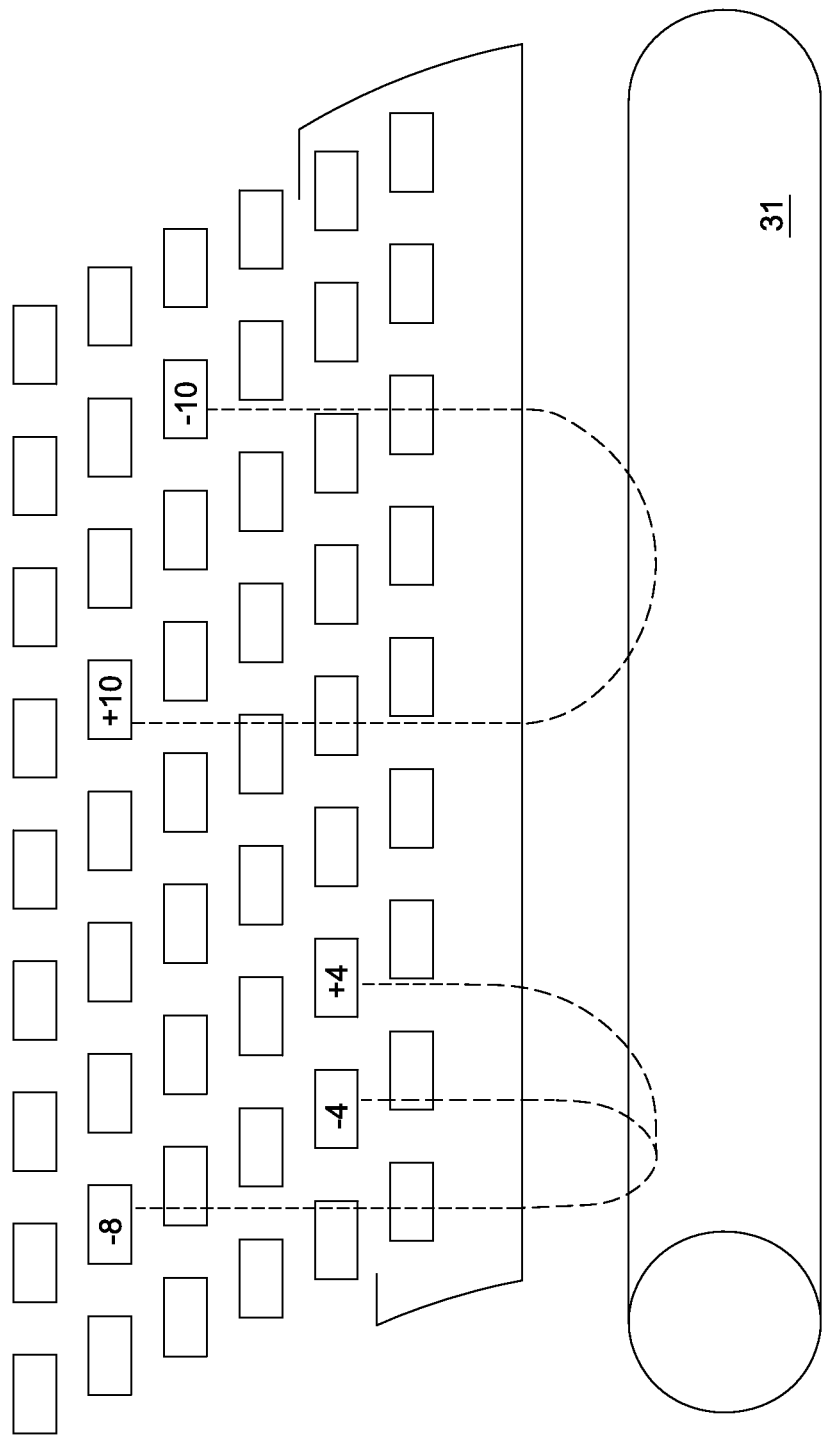
FIG. 53 is a diagrammatic illustration of how, by sourcing and sinking current between the electrodes of separate sets of electrodes, current can be simultaneously flowed through three, four or more sections of tissue with the assembly of this invention.

FIG. 53 illustrates another feature of assembly 28 or 290. Here, by selectively sourcing and sinking current through two sets of spaced apart electrodes, current flow is simultaneously focused through two or more spaced apart regions of the tissue against which the array is applied. In FIG. 53, the electrodes are arranged in the same pattern as the electrodes of FIG. 52.

In FIG. 53, the second column down/second row from the left electrode functions as the primary sink electrode for a first current flow path. The fifth column down/second and third row from the left electrodes function as the complementary electrodes that source the current sunk to this first primary sink electrode. Simultaneously with the current being flowed between the electrodes of this first set of electrodes, current is flowed through a second set of electrodes. This second set of electrodes includes the second column down/sixth row from the left electrode functioning as the primary source electrode. Also part of this second set of electrodes is the third column down/eighth row from the right electrode functioning as the primary sink electrode.

Spaced apart bridges 302, 304 and 306 of assembly 290 of this invention allow the assembly to be fitted in a deployment cannula that is smaller in width the width of the unfolded assembly. This allows the assembly to be positioned percutaneously, through the access cannula, or using other minimally invasive surgical techniques. In addition to allowing the assembly to be folded, bridge 302, 304 and 306, when in registration with each other, allow the assembly to flex. This facilitates the precise positioning of the assembly 290. Moreover, in versions of the invention constructed as described above, the bridges are narrower adjacent the distal end of the assembly in comparison to the proximal end. This feature of the invention provides the assembly with more flexibility adjacent the distal end, this being the end of the assembly in which flexibility is most useful for positioning the assembly.

While bridges 302, 304 and 306 are, as a result of the folding process, positioned to overlap, neither the bridges themselves nor the associated electrode carrying tabs 318 are subjected to folding. This makes it possible to construct the electrodes 292 of the assembly 290 of this invention with the iridium layers having the necessary thickness without running the risk that appreciable folding of these layers will result in their breakage.

Further, the sealing of drive module die 408 in the outer capsule mechanically isolates both the die and the underlying terminal pad 296. This prevents the rivets that connect the die to the terminal pad from being exposed to excessive strain during the array folding/bending process. This strain, if excessive, could fracture the rivets. Post-deployment, the outer capsule prevents biological or chemical attack on components fabricated on the die 408.

Membranes 322 and 324 prevent damage to the tissue surrounding the assembly 290. The membranes 322 and 324 also inhibit tissue growth adjacent and between the features of the assembly. The minimization of this tissue growth reduces the likelihood such tissue growth could interfere with the removal of the assembly 290.

VI. Alternative Embodiments

It should be understood that the foregoing is directed to specific versions of this invention. Other versions of this invention may have features different from what has been described. For examples, the features of electrode array assemblies 28 and 290 can be selectively combined with each other.

It should be appreciated that assemblies 28 and 290 of this invention may have applications other than for implantation adjacent the spinal cord dura. For example, the assemblies can be implanted against the brain, the vagus nerve, sacral nerves, phrenic nerves, thalamus or other nervous system structure. In these versions of the invention, the structural features of the assembly may have dimensions different from what has been described. For example, by increasing the width of beams 320 one could increase the potential energy the beams release during the unfolding process. Providing an array assembly of this invention with wide-width beams may be useful if the assembly is intended for deployment adjacent tissue that is highly resistant to such deployment. Likewise, the thicknesses of the components may be different from what has been described.

In some versions of this invention, it may not be necessary to provide the frame. Similarly, there is no requirement that in versions of the invention with a frame, that the whole of the frame be formed from superelastic material. Thus, in some versions of the invention, it may be necessary to only form the beams 320 of the superelastic material.

For example, there is no requirement that all versions of electrode array assembly have three bridges. Some versions of the invention may just have one or two bridges while other versions of the invention have four or more bridges. In versions of the invention with two bridges, one bridge may extend from the assembly terminal pad. The second bridge is parallel to and laterally spaced from the first bridge. To fit the assembly 290 in the deployment cannula, the second bridge is folded over the first bridge.

In versions of the invention with an even number of four or more bridges, equal number of bridges may extend from opposed sides of the terminal pad. The bridges are folded together so that one face of one bridge is folded toward the adjacent face of the opposed bridge. Thus, a fold of four bridges may appear as the letter "W". In versions of the invention with an odd number of five or more bridges, there may be a center bridge that extends from the terminal pad. The other bridges are folded over or under the center bridge. Alternatively, the bridges on one side of the center bridge are folded first so as to be close to the center bridge. The bridges on the other side of the center bridge are then folded so as to be disposed over the bridges closer to the center bridge.

Likewise, there is no requirement that in all versions of the invention, the widths of the bridges decrease from the location at which the drive module is attached to the assembly. Furthermore, in some versions of the invention, the widths of the bridges may change along their lengths for reasons other than the number of conductors present on the bridges. Thus, some bridges may have relatively wide sections where it is desired to minimize array flexibility and other sections of narrow width where it is desirable to increase flexibility. In some embodiments of the invention bridge sections of narrow width and wide width may be interleaved with each other.

Regardless of the number of bridges or rows and columns of electrodes, it should be understood that in most versions of the invention, the assembly includes at least 16 individual electrodes and in many versions of the invention at least 30 electrodes.

Other variations in the geometry of the array are also possible. For example, in the described version of the invention there are two beams 320 between each row of electrodes 292 (tabs 318). In some versions of the invention there may only be a single inter-bridge beam or three or more inter-bridge beams between each row of electrode-carrying tabs 318. Similarly, there is no requirement that the number of inter-bridge beams be symmetrical across the array or identical along the length of the array. In some versions of the invention, these beams may even extend diagonally between the bridges. Such variations may be desirable to regulate the extent the potential energy released by the beams forces the unfolding of the array.

Similarly, there is no requirement that in all versions of the invention, the electrodes only be located on one side of the assembly. In some versions of the invention, electrodes may be disposed on all sides of the substrate. In these versions of the invention, the assembly could be considered to have opposed active sides.

The materials from which assemblies 28 and 290 is formed may also vary from what has been described. For example, the actual material of each electrode that serves as the interface material with the adjacent material may not always be iridium. In some versions of the invention, this material may be iridium oxide, platinum, an alloy of platinum, a platinum oxide or other conductive biocompatible material.

In some versions of the invention, adhesives as opposed to mechanical connecting members hold the die 408 to the terminal pad 296.

Similarly in some versions of the invention, manufacturing methods may dictate that the outer capsule shell 418 and cap 420 be formed as a single molded-in-place structure.

Further, there is no requirement that in all versions of the invention electrode-carrying tabs extend from both sides of each bridge. In some versions of the invention, it may be desirable that only a single column of electrode-carrying tabs extend from a single side of one or more bridges. Typically, it is one or both of the outermost bridges, the bridges located furthest from the terminal pad, that include only a single column of electrode-carrying tabs.

Similarly, alternative methods may be used to manufacture the assemblies 28 and 290 of this invention may be different from what has been described. For example, the method of manufacture disclosed in U.S. Pat. App. No. 61/057,684, filed 30 May 2008, published as U.S. Pat. Pub. No. US 2009/0293270 A1 and PCT Pub. No. WO 2009/155084 A1, the contents of which are incorporated herein by reference discloses one such alternative method of manufacture.

Likewise, the number of rows of electrodes 292 may be fewer or greater than in the described embodiment.

Likewise, the structure of the drive module is understood to be exemplary, not limiting. In alternative versions of the invention, the drive module may include less or more sub-circuits than in the described version of the invention. For example, in some versions of the invention, the only circuit in the drive module 294 may be a multiplexer. In these versions of the invention, the implantable device controller 428 does more than supply the current that is flowed through the tissue. The IDC 428 also outputs the instructions that cause the multiplexer to route the current to/from the specific electrodes 292.

In some methods of implanting the electrode array assembly of this invention, a stylet may be used to puncture the skin so as to form a portal into which the access cannula is inserted.

It should likewise be understood that there is no requirement that the electrode array assembly of this invention always be implanted percutaneously. Other procedures may be used to deploy this electrode array assembly near the target tissue through which the current is be flowed. Thus, in some cardiac application where the array is applied near the heart or neurological applications where the array is to be applied adjacent the brain other procedures such as minimally invasive surgical procedures may be used to implant the array.

Similarly, in some versions of the invention the IDC 428 may include a battery that is not rechargeable. In these versions of the invention a minor surgical procedure may be needed to replace the battery if not the whole of the IDC.

Also, while in the disclosed version of the invention, the electrode array assembly is bent, folded to be fitted in the insertion tool, that may not always be the case. In some constructions of the invention, to reduce the width of the electrode assembly, the assembly may be rolled. Thus the folding or bending of the electrode array should be interpreted include the rolling of the array. Again, the electrodes may be located on tabs that are not subjected to the degree of rolling to which the surrounding portions of the assembly are rolled.

It should similarly be appreciated that deployment assembly of this invention including deployment cannula 240 within access cannula 250 may be used to deploy electrode arrays other than the disclosed electrode arrays. Thus, cannulae 240 and 250 may be used to deploy and properly orient an electrode array that, upon retraction of the deployment cannula 240 does not unfold or unbend.

Likewise the deployment cannulae 240 and 250 may have different shapes than what has been described. These cannulae can have lumens that have circular or non-circular cross sections that may or may not vary in profile along the length of the cannulae. Further, there is no requirement that the inner and outer delivery cannulae of this invention all be constructed so that the cannulae lumens in which the electrode assemblies are seated are open at both ends.

Accordingly, it is the object of the appended claims to cover all such variations and modifications that come with the scope of the below claims.

What is claimed is:

1. An electrode array, said electrode array including:
   a frame formed from flexible material, said frame shaped to define:
      a plurality of bridges, each said bridge having a longitudinal axis that extends from a proximal end of said bridge to a distal end of said bridge, said bridges being located side by side and being laterally spaced apart from each other;
      a plurality of tabs that extend from said bridges, wherein: plural said tabs extend away from the longitudinal axis of a first said bridge towards an adjacent second said bridge, said tabs extending away from the first said bridge being spaced apart from each other along the first said bridge; plural said tabs that extend away from the longitudinal axis of the second said bridge towards the first said bridge, said tabs extending away from the second said bridge being spaced apart from each other along the second said bridge; and wherein said tabs that extend outwardly from the first said bridge are separate from said tabs that extend outwardly from the second said bridge; and
      a plurality of beams that are separate from said tabs, said beams extending between the first said bridge and the second said bridge so as to connect the first and second said bridges together, wherein said frame is configured to bend around said beams so that, as a result of the bending, the said first bridge at least partially overlaps the second said bridge; and
   a plurality of electrodes, each said electrode being formed from biocompatable material through which a current can be sourced to or sunk from tissue against which the electrodes are disposed, said electrodes being disposed on said frame tabs.

2. The electrode array of claim 1, wherein at least one said beam extends between two spaced apart tabs that extend from the first said bridge to a location on the second said bridge that is between two spaced apart tabs that extend from the second said bridge.

3. The electrode array of claim 1, wherein a plurality of said beams extend between two spaced apart tabs that extend from the first said bridge to locations on the second said bridge that are between two spaced apart tabs that extend from the second said bridge.

4. The electrode array of claim 1, wherein:
   a plurality of said beams extend between two spaced apart tabs that extend from the first said bridge to locations on the second said bridge that are between two spaced apart tabs that extend from the second said bridge, and said beams are, along said frame, spaced apart from each other so as to define a void space between said beams; and
   a flexible membrane extends between said beams across the void space between said beams.

5. The electrode array of claim 1, wherein at least one said beam is formed from material capable of storing potential energy, so that after the bending of said beams, the potential energy in the at least one said beam will release so as to cause said beams to unfold.

6. The electrode array of claim 1 wherein:
   said frame is further formed so that the first said bridge is further formed to have tabs that extend outwardly away from the longitudinal axis of the said first bridge and away from the second said bridge; and
   said electrodes are disposed on the tabs of the first said bridge that extend away from the second said bridge.

7. The electrode array of claim 1, wherein said electrodes are disposed over surfaces of said tabs on which said electrodes are disposed.

8. The electrode array of claim 1, wherein at least one said electrode is disposed on a said tab so as to at least partially be positioned outwardly of the said bridge from which said tab extends.

9. The electrode array of claim 1, wherein:
   said frame is formed from metal; and
   a layer of electrically insulating material disposed on said frame so as to be located between said frame and said electrodes.

10. An electrode array for implantation into living tissue, said electrode array including:
    a frame formed from flexible material, said frame shaped to have:
       at least one foot;
       a head spaced away from said foot;
       a plurality of bridges that extend between said at least one foot and said head, said bridges having longitudinal axes that extend between said foot and said head and being spaced apart from each other;
       at least one beam, said beam extending laterally between said bridges and is configured to flex when said frame is folded so as to cause at least two said bridges to at least partially overlap; and
       a plurality of tabs that extend outwardly from said bridges so as to extend away from the longitudinal axis of the said bridge with which said tabs are associated wherein: plural said tabs extend outwardly from a first said bridge at spaced apart locations along the first said bridge towards a second said bridge; plural said tabs extend outwardly from the second said bridge at spaced apart locations along the second said bridge towards the first said bridge wherein said tabs that extend from said first said bridge are separate from said tabs forming the second said bridge; and said frame is further formed so that at least one said beam extends from the first said bridge at a location between the said tabs that extend outwardly from the first said bridge to a location on said second said bridge between the said tabs that extend outwardly from the second said bridge; and
    a plurality of electrodes, each said electrode being formed from biocompatable material through which a current can be sourced to or sunk from tissue against which the electrodes are disposed, said electrodes being disposed on said frame tabs.

11. The electrode array of claim 10, wherein:
said frame is further formed so that:
    at least three said bridges extend between said at least one foot and said head, wherein the second said bridge is located between the first said bridge and a third said bridge;
    at least one said beam extends between the first said bridge and the second said bridge and at least one said beam extends between the second said bridge and the third said bridge, said beams being able to flex when said frame is folded so as to cause said bridges to at least partially overlap with each other;
    a plurality of said tabs extend outwardly from the second said bridge at spaced apart locations on the second said bridge towards the third said bridge and a plurality of said tabs extend outwardly from the third said bridge at spaced apart locations on the third said beam towards the second said bridge; and
    at least one said beam extends from a location on the second said bridge between two said spaced apart tabs that extend outwardly from the second said bridge to a location on the third said bridge between two said spaced apart tabs that extend outwardly from the third said bridge, said beam being able to flex when said frame is folded so as that the first, second and third said bridges at least partially overlap; and
    electrodes are disposed on said tabs that extend outwardly from the second said bridge towards the third said bridge and on said tabs that extend outwardly from the third said bridge.

12. The electrode array of claim 10, wherein a plurality of said beams extend between two spaced apart tabs that extend outwardly from the first said bridge to locations on the second said bridge that are between two spaced apart tabs that extend outwardly from the second said bridge.

13. The electrode array of claim 10, wherein:
    a plurality of said beams extend between two spaced apart tabs that extend from the first said bridge to locations on the second said bridge that are between two spaced apart tabs that extend from the second said bridge, and said beams are, along said frame, spaced apart from each other so as to define a void space between said beams; and
    a flexible membrane extends between said beams across the void space between said beams.

14. The electrode array of claim 10, wherein said electrodes are disposed over surfaces of said tabs on which said electrodes are disposed.

15. The electrode array of claim 10, wherein at least one said electrode is disposed on a said tab so as to at least partially be positioned outwardly of the said bridge from which said tab extends.

16. The electrode array of claim 10, wherein said frame is further formed so that, when said frame is folded, at least one tab with electrode that extends from the first said bridge at least partially overlaps a said tab with electrode that extends from the second said bridge.

17. The electrode array of claim 10, wherein:
    tabs extend outwardly relative to the longitudinal axis of at least one said bridge from opposed sides of the said bridge; and
    an electrode is disposed on each of the said tabs that extends outwardly from the opposed sides of the said bridge.

18. An electrode array for implantation into living tissue, said array including:
    a frame, said frame shaped to have:
        at least two bridges that are parallel and spaced apart from each other, said brides having longitudinal axes that extend from proximal ends of said bridges to distal ends of said bridges;
        a plurality of beams that extend between and connect the at least two said bridges, at least two said beams being spaced apart from each other along the longitudinal axes of said bridges, said beams configured to be flexible so that said frame can be folded around said beams so that a first one of said bridges at least partially overlaps a second one of said bridges; and
        at least one tab integral with the first said bridge and that extends away from the longitudinal axis of the first said bridge toward the second said bridge, said tab extending away from the first said bridge at a location between the two spaced apart beams and at least one tab integral with the second said bridge and that extends away from the longitudinal axis of the second said bridge toward the first said bridge, said tab extending away from the second said bridge at a location between the two spaced apart beams, wherein said tab integral with the first bridge and said tab integral with the second said bridge are separate from said beams and are spaced apart from each other so that, when said frame is folded around said beams, said tabs extend beyond the folded said beams; and
    a plurality of electrodes, each said electrode being formed from biocompatable material through which a current can be sourced to or sunk from tissue against which the electrodes are disposed, said electrodes being disposed on said frame tabs so as to be located at least partially outwardly of the bridges of from which said tabs outwardly extend.

19. The electrode array of claim 18, wherein said frame is formed to include at least one foot and the proximal ends of said bridges are connected to said foot and said bridges extend distally from said foot.

20. The electrode array of claim 18, wherein:
    tabs extend outwardly relative to the longitudinal axis of at least one said bridge from opposed sides of the said bridge; and
    an electrode is disposed on each of the said tabs that extends outwardly from the opposed sides of the said bridge.

21. The electrode array of claim 18, wherein:
said frame is further shaped to have:
    a third said bridge that is parallel with the first and second said bridges, and said bridges are arranged so that the second said bridge is between the first said bridge and the second said bridge;
    a plurality of said beams that are longitudinally spaced from each other along the longitudinal axes of said bridges and that extend between the second said bridge and the third said bridge, said beams, said beams being sufficiently flexible so that said frame can be folded so that the second said bridges at least partially overlaps the third said bridge; and
    at least one said tab integral with the second said bridge and that extends away from the longitudinal axis of the second said bridge toward the third said bridge, said tab extending away from the second said bridge at a location between the two spaced apart beams that extend to the third said bridge and at least one tab integral with the third said bridge and that extends away from the longitudinal axis of the third said bridge toward the second said bridge, said tab extending away from the third said bridge at a location between the two spaced apart beams that extend to the third said bridge wherein, said tab integral with the second said bridge and said tab integral with the third said bridge are spaced apart from each other so that, when said frame is folded around said beams, said tabs do not fold and extend beyond the folded said beams; and an electrode is located on the said tab associated with the second said bridge that extends towards the third said bridge and an electrode is located on the said tab associated with the third said bridge that extends towards the second said bridge.

22. The electrode array of claim 18, wherein said frame is further shaped so that, when said frame is folded, at least one said tab with electrode that extends from the first said bridge at least partially overlaps at least one tab with electrode that extends from the second said bridge.

23. The electrode array of claim 18, wherein said electrodes are disposed over surfaces of said tabs on which said electrodes are disposed.

* * * * *